(12) United States Patent
McFarland

(10) Patent No.: US 8,999,696 B2
(45) Date of Patent: Apr. 7, 2015

(54) COMPOSITIONS AND METHODS FOR ENHANCING THE DEGRADATION OR CONVERSION OF CELLULOSE-CONTAINING MATERIAL

(75) Inventor: Keith McFarland, Davis, CA (US)

(73) Assignee: Novozymes, Inc., Davis, CA (US)

( * ) Notice: Subject to any disclaimer, the term of this patent is extended or adjusted under 35 U.S.C. 154(b) by 857 days.

(21) Appl. No.: 12/598,574

(22) PCT Filed: May 9, 2008

(86) PCT No.: PCT/US2008/005927
§ 371 (c)(1),
(2), (4) Date: Nov. 2, 2009

(87) PCT Pub. No.: WO2008/140749
PCT Pub. Date: Nov. 20, 2008

(65) Prior Publication Data
US 2010/0143967 A1   Jun. 10, 2010

Related U.S. Application Data

(60) Provisional application No. 60/917,208, filed on May 10, 2007.

(51) Int. Cl.
C12N 9/42 (2006.01)
C12P 7/06 (2006.01)

(52) U.S. Cl.
CPC ............... *C12N 9/2437* (2013.01); *C12P 7/06* (2013.01); *C12Y 302/01004* (2013.01); *C12Y 302/01021* (2013.01); *C12Y 302/01091* (2013.01); *C12N 9/2445* (2013.01); *Y02E 50/17* (2013.01)

(58) Field of Classification Search
None
See application file for complete search history.

(56) References Cited

U.S. PATENT DOCUMENTS

| 6,573,086 | B1 | 6/2003 | Emalfrab et al. |
| 7,883,872 | B2 * | 2/2011 | Gusakov et al. ................ 435/96 |
| 2007/0077630 | A1 | 4/2007 | Harris et al. |

FOREIGN PATENT DOCUMENTS

| WO | WO 95/24471 | 9/1995 |
| WO | WO 00/20555 | 4/2000 |
| WO | WO 01/25468 | 4/2001 |
| WO | WO 01/79507 | 10/2001 |
| WO | WO 03/000941 | 1/2003 |
| WO | WO 2005/074647 | 8/2005 |
| WO | WO 2005/074656 | 8/2005 |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*

* cited by examiner

*Primary Examiner* — Richard Hutson
(74) *Attorney, Agent, or Firm* — Robert L. Starnes

(57) ABSTRACT

The present invention relates to methods for degrading or converting a cellulose-containing material, comprising: treating the cellulose-containing material with an effective amount of a cellulolytic enzyme composition comprising a polypeptide having cellulolytic enhancing activity, and one or more (several) components selected from the group consisting of a CEL7 polypeptide having endoglucanase activity, a CEL12 polypeptide having endoglucanase activity, a CEL45 polypeptide having endoglucanase activity, a CEL7 polypeptide having cellobiohydrolase activity with a cellulose binding domain, and a CEL7 polypeptide having cellobiohydrolase activity without a cellulose binding domain. The present invention also relates to such cellulolytic enzyme compositions.

19 Claims, 1 Drawing Sheet

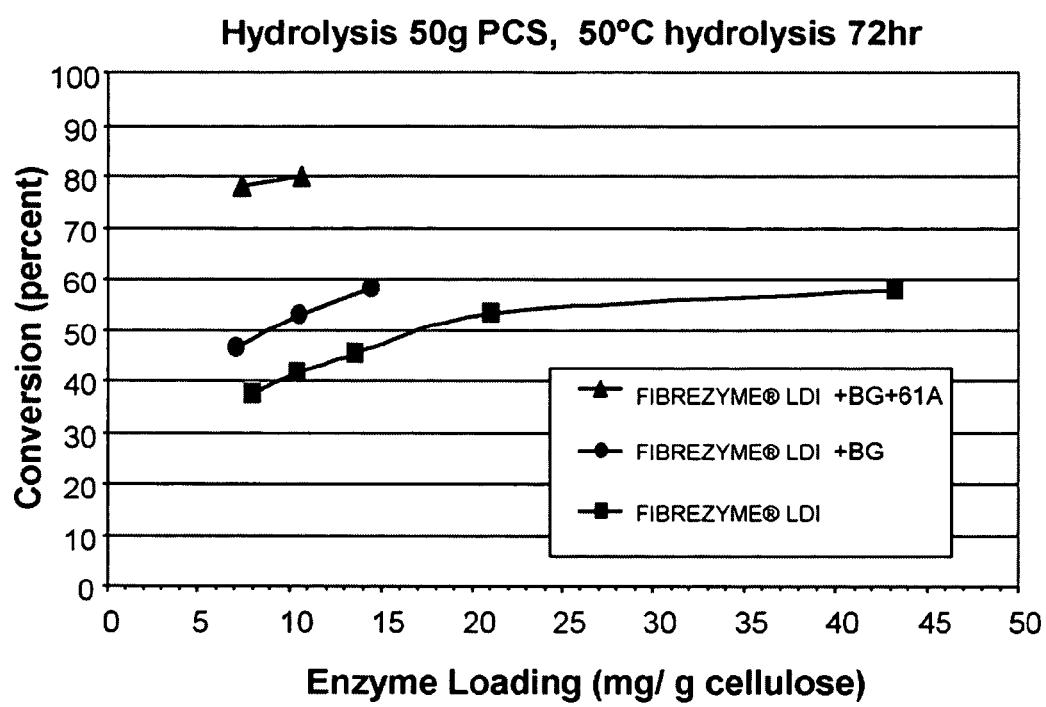

COMPOSITIONS AND METHODS FOR ENHANCING THE DEGRADATION OR CONVERSION OF CELLULOSE-CONTAINING MATERIAL

CROSS-REFERENCE TO RELATED APPLICATIONS

This application is a 35 U.S.C. 371 national application of PCT/US2008/005927 filed on May 9, 2008 and claims priority from U.S. provisional application Ser. No. 60/917,208 filed on May 10, 2007, which applications are fully incorporated herein by reference.

REFERENCE TO A SEQUENCE LISTING

This application contains a Sequence Listing in computer readable form. The computer readable form is incorporated herein by reference.

REFERENCE TO A DEPOSIT OF BIOLOGICAL MATERIAL

This application contains a reference to deposits of biological material, which deposits are incorporated herein by reference.

BACKGROUND OF THE INVENTION

1. Field of the Invention

The present invention relates to compositions and methods for degrading or converting a cellulose-containing material and for producing a substance from a cellulose-containing material.

2. Description of the Related Art

Cellulose is a polymer of the simple sugar glucose covalently bonded by beta-1,4-linkages. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of cellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the cellulose is converted to glucose, the glucose is easily fermented by yeast into ethanol.

Many commercial cellulolytic enzyme preparations are available but have limited utility in the degradation and conversion of cellulose-containing material. It would be advantageous in the art to improve the ability of these commercial enzyme preparations to degrade and convert cellulosic feedstocks.

WO 2005/074647 discloses isolated polypeptides having cellulolytic enhancing activity and polynucleotides thereof from *Thielavia terrestris*.

WO 2005/074656 discloses an isolated polypeptide having cellulolytic enhancing activity and the polynucleotide thereof from *Thermoascus aurantiacus*.

U.S. Published Application Serial No. 2007/0077630 discloses an isolated polypeptide having cellulolytic enhancing activity and the polynucleotide thereof from *Trichoderma reesei*.

WO 1995/024471 discloses a CEL7 polypeptide having endoglucanase activity and the polynucleotide thereof.

WO 2001/79507 discloses a CEL7 polypeptide having cellobiohydrolase activity with a cellulose binding domain and the polynucleotide thereof.

WO 2003/000941 discloses a CEL7 polypeptide having cellobiohydrolase activity without a cellulose binding domain and the polynucleotide thereof.

WO 2001/25468 discloses a CEL12 polypeptide having endoglucanase activity and the polynucleotide thereof.

WO 2000/20555 discloses a CEL45 polypeptide having endoglucanase activity and the polynucleotide thereof.

The present invention relates to methods for improving the ability of cellulolytic enzyme compositions to degrade and convert cellulosic feedstocks.

SUMMARY OF THE INVENTION

The present invention relates to methods for degrading or converting a cellulose-containing material, comprising: treating the cellulose-containing material with an effective amount of a cellulolytic enzyme composition comprising a polypeptide having cellulolytic enhancing activity, and one or more (several) components selected from the group consisting of a CEL7 polypeptide having endoglucanase activity, a CEL12 polypeptide having endoglucanase activity, a CEL45 polypeptide having endoglucanase activity, a CEL7 polypeptide having cellobiohydrolase activity with a cellulose binding domain, and a CEL7 polypeptide having cellobiohydrolase activity without a cellulose binding domain;

wherein the CEL7 polypeptide having endoglucanase activity is selected from the group consisting of: (a) a polypeptide comprising an amino acid sequence having at least 70% sequence identity to the mature polypeptide of SEQ ID NO: 2; (b) a polypeptide encoded by a polynucleotide that hybridizes under at least medium stringency conditions with (i) the mature polypeptide coding sequence of SEQ ID NO: 1, (ii) the genomic DNA sequence comprising the mature polypeptide coding sequence of SEQ ID NO: 1, or (iii) a full-length complementary strand of (i) or (ii); (c) a polypeptide encoded by a polynucleotide comprising a nucleotide sequence having at least 70% sequence identity to the mature polypeptide coding sequence of SEQ ID NO: 1; and (d) a variant comprising a substitution, deletion, and/or insertion of one or more (several) amino acids of the mature polypeptide of SEQ ID NO: 2;

wherein the CEL12 polypeptide having endoglucanase activity is selected from the group consisting of: (a) a polypeptide comprising an amino acid sequence having at least 70% sequence identity to the mature polypeptide of SEQ ID NO: 4; (b) a polypeptide encoded by a polynucleotide that hybridizes under at least medium stringency conditions with (i) the mature polypeptide coding sequence of SEQ ID NO: 3, (ii) the genomic DNA sequence comprising the mature polypeptide coding sequence of SEQ ID NO: 3, or (iii) a full-length complementary strand of (i) or (ii); (c) a polypeptide encoded by a polynucleotide comprising a nucleotide sequence having at least 70% sequence identity to the mature polypeptide coding sequence of SEQ ID NO: 3; and (d) a variant comprising a substitution, deletion, and/or insertion of one or more (several) amino acids of the mature polypeptide of SEQ ID NO: 4;

wherein the CEL45 polypeptide having endoglucanase activity is selected from the group consisting of: (a) a polypeptide comprising an amino acid sequence having at least 70% sequence identity to the mature polypeptide of SEQ ID NO: 6; (b) a polypeptide encoded by a polynucleotide that hybridizes under at least medium stringency conditions with (i) the mature polypeptide coding sequence of SEQ ID NO: 5, (ii) the cDNA sequence contained in the mature polypeptide coding sequence of SEQ ID NO: 5, or (iii) a full-length complementary strand of (i) or (ii); (c) a polypeptide encoded by a polynucleotide comprising a nucleotide sequence having at least 70% sequence identity to the mature polypeptide coding sequence of SEQ ID NO: 5; and (d) a variant comprising a substitution, deletion, and/or insertion of one or more (several) amino acids of the mature polypeptide of SEQ ID NO: 6;

wherein the CEL7 polypeptide having cellobiohydrolase activity with a cellulose binding domain is selected from the group consisting of: (a) a polypeptide comprising an amino acid sequence having at least 70% sequence identity to the mature polypeptide of SEQ ID NO: 8; (b) a polypeptide encoded by a polynucleotide that hybridizes under at least medium stringency conditions with (i) the mature polypeptide coding sequence of SEQ ID NO: 7, (ii) the cDNA sequence contained in the mature polypeptide coding sequence of SEQ ID NO: 7, or (iii) a full-length complementary strand of (i) or (ii); (c) a polypeptide encoded by a polynucleotide comprising a nucleotide sequence having at least 70% sequence identity to the mature polypeptide coding sequence of SEQ ID NO: 7; and (d) a variant comprising a substitution, deletion, and/or insertion of one or more (several) amino acids of the mature polypeptide of SEQ ID NO: 8;

wherein the CEL7 polypeptide having cellobiohydrolase activity without a cellulose binding domain is selected from the group consisting of: (a) a polypeptide comprising an amino acid sequence having at least 70% sequence identity to the mature polypeptide of SEQ ID NO: 10; (b) a polypeptide encoded by a polynucleotide that hybridizes under at least medium stringency conditions with (i) the mature polypeptide coding sequence of SEQ ID NO: 9, (ii) the genomic DNA sequence comprising the mature polypeptide coding sequence of SEQ ID NO: 9, or (iii) a full-length complementary strand of (i) or (ii); (c) a polypeptide encoded by a polynucleotide comprising a nucleotide sequence having at least 70% sequence identity to the mature polypeptide coding sequence of SEQ ID NO: 9; and (d) a variant comprising a substitution, deletion, and/or insertion of one or more (several) amino acids of the mature polypeptide of SEQ ID NO: 10; and wherein the presence of the polypeptide having cellulolytic enhancing activity increases the degradation of the cellulose-containing material by the cellulolytic enzyme composition compared to the absence of the polypeptide having cellulolytic enhancing activity.

The present invention also relates to methods for producing a substance, comprising:

(A) saccharifying a cellulose-containing material with an effective amount of a cellulolytic enzyme composition comprising a polypeptide having cellulolytic enhancing activity; and one or more (several) components selected from the group consisting of a CEL7 polypeptide having endoglucanase activity, a CEL12 polypeptide having endoglucanase activity, a CEL45 polypeptide having endoglucanase activity, a CEL7 polypeptide having cellobiohydrolase activity with a cellulose binding domain, and a CEL7 polypeptide having cellobiohydrolase activity without a cellulose binding domain;

wherein the CEL7 polypeptide having endoglucanase activity is selected from the group consisting of: (a) a polypeptide comprising an amino acid sequence having at least 70% sequence identity to the mature polypeptide of SEQ ID NO: 2; (b) a polypeptide encoded by a polynucleotide that hybridizes under at least medium stringency conditions with (i) the mature polypeptide coding sequence of SEQ ID NO: 1, (ii) the genomic DNA sequence comprising the mature polypeptide coding sequence of SEQ ID NO: 1, or (iii) a full-length complementary strand of (i) or (ii); (c) a polypeptide encoded by a polynucleotide comprising a nucleotide sequence having at least 70% sequence identity to the mature polypeptide coding sequence of SEQ ID NO: 1; and (d) a variant comprising a substitution, deletion, and/or insertion of one or more (several) amino acids of the mature polypeptide of SEQ ID NO: 2;

wherein the CEL12 polypeptide having endoglucanase activity is selected from the group consisting of: (a) a polypeptide comprising an amino acid sequence having at least 70% sequence identity to the mature polypeptide of SEQ ID NO: 4; (b) a polypeptide encoded by a polynucleotide that hybridizes under at least medium stringency conditions with (i) the mature polypeptide coding sequence of SEQ ID NO: 3, (ii) the genomic DNA sequence comprising the mature polypeptide coding sequence of SEQ ID NO: 3, or (iii) a full-length complementary strand of (i) or (ii); (c) a polypeptide encoded by a polynucleotide comprising a nucleotide sequence having at least 70% sequence identity to the mature polypeptide coding sequence of SEQ ID NO: 3; and (d) a variant comprising a substitution, deletion, and/or insertion of one or more (several) amino acids of the mature polypeptide of SEQ ID NO: 4;

wherein the CEL45 polypeptide having endoglucanase activity is selected from the group consisting of: (a) a polypeptide comprising an amino acid sequence having at least 70% sequence identity to the mature polypeptide of SEQ ID NO: 6; (b) a polypeptide encoded by a polynucleotide that hybridizes under at least medium stringency conditions with (i) the mature polypeptide coding sequence of SEQ ID NO: 5, (ii) the cDNA sequence contained in the mature polypeptide coding sequence of SEQ ID NO: 5, or (iii) a full-length complementary strand of (i) or (ii); (c) a polypeptide encoded by a polynucleotide comprising a nucleotide sequence having at least 70% sequence identity to the mature polypeptide coding sequence of SEQ ID NO: 5; and (d) a variant comprising a substitution, deletion, and/or insertion of one or more (several) amino acids of the mature polypeptide of SEQ ID NO: 6;

wherein the CEL7 polypeptide having cellobiohydrolase activity with a cellulose binding domain is selected from the group consisting of: (a) a polypeptide comprising an amino acid sequence having at least 70% sequence identity to the mature polypeptide of SEQ ID NO: 8; (b) a polypeptide encoded by a polynucleotide that hybridizes under at least medium stringency conditions with (i) the mature polypeptide coding sequence of SEQ ID NO: 7, (ii) the cDNA sequence contained in the mature polypeptide coding sequence of SEQ ID NO: 7, or (iii) a full-length complementary strand of (i) or (ii); (c) a polypeptide encoded by a polynucleotide comprising a nucleotide sequence having at least 70% sequence identity to the mature polypeptide coding sequence of SEQ ID NO: 7; and (d) a variant comprising a substitution, deletion, and/or insertion of one or more (several) amino acids of the mature polypeptide of SEQ ID NO: 8;

wherein the CEL7 polypeptide having cellobiohydrolase activity without a cellulose binding domain is selected from the group consisting of: (a) a polypeptide comprising an amino acid sequence having at least 70% sequence identity to the mature polypeptide of SEQ ID NO: 10; (b) a polypeptide encoded by a polynucleotide that hybridizes under at least medium stringency conditions with (i) the mature polypeptide coding sequence of SEQ ID NO: 9, (ii) the cDNA sequence contained in or the genomic DNA sequence comprising the mature polypeptide coding sequence of SEQ ID NO: 9, or (iii) a full-length complementary strand of (i) or (ii); (c) a polypeptide encoded by a polynucleotide comprising a nucleotide sequence having at least 70% sequence identity to the mature polypeptide coding sequence of SEQ ID NO: 9; and (d) a variant comprising a substitution, deletion, and/or insertion of one or more (several) amino acids of the mature polypeptide of SEQ ID NO: 10; and wherein the presence of the polypeptide having cellulolytic enhancing activity increases the degradation of the cellulose-containing material by the cellulolytic enzyme composition compared to the absence of the polypeptide having cellulolytic enhancing activity;

(B) fermenting the saccharified cellulose-containing material of step (a) with one or more (several) fermenting microorganisms to produce a fermentation product; and (C) recovering the fermentation product.

The present invention also relates to such cellulolytic enzyme compositions comprising an effective amount of a polypeptide having cellulolytic enhancing activity.

BRIEF DESCRIPTION OF THE FIGURE

FIG. 1 shows digestions of 50 g of PCS with FIBREZYME® LDI alone; FIBREZYME® LDI and *Aspergillus oryzae* beta-glucosidase; and FIBREZYME® LDI, *Aspergillus oryzae* beta-glucosidase, and *Thermoascus auranticus* GH61A protein for 72 hours at 50° C. and pH 5.0. Curved line connecting the datapoints is for clarity of illustration only.

DEFINITIONS

Cellulolytic enhancing activity: The term "cellulolytic enhancing activity" is defined herein as a biological activity that enhances the hydrolysis of a cellulose-containing material by proteins having cellulolytic activity. For purposes of the present invention, cellulolytic enhancing activity is determined by measuring the increase in reducing sugars or the increase of the total of cellobiose and glucose from the hydrolysis of a cellulose-containing material by cellulolytic protein under the following conditions: 1-50 mg of total protein containing 80-99.5% w/w cellulolytic protein/g of cellulose in PCS and 0.5-20% w/w protein of cellulolytic enhancing activity for 1-7 day at 50° C. compared to a control hydrolysis with equal total protein loading without cellulolytic enhancing activity (1-50 mg of cellulolytic protein/g of cellulose in PCS). In a preferred aspect, a mixture of CELLUCLAST® 1.5 L (Novozymes A/S, Bagsværd, Denmark) in the presence of 3% *Aspergillus oryzae* beta-glucosidase (recombinantly produced in *Aspergillus oryzae* according to WO 02/095014) or 3% *Aspergillus fumigatus* beta-glucosidase (recombinantly produced in *Aspergillus oryzae* according to Example 22 of WO 02/095014) of cellulase protein loading is used as a standard of the cellulolytic activity.

The polypeptides having cellulolytic enhancing activity have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the cellulolytic enhancing activity of the mature polypeptide of SEQ ID NO: 12, 14, 16, 18, 20, 22, or 24.

The polypeptides having cellulolytic enhancing activity enhance the hydrolysis of a cellulose-containing material by proteins having cellulolytic activity by reducing the amount of cellulolytic enzyme required to reach the same degree of hydrolysis preferably at least 0.1-fold, more at least 0.2-fold, more preferably at least 0.3-fold, more preferably at least 0.4-fold, more preferably at least 0.5-fold, more preferably at least 1-fold, more preferably at least 3-fold, more preferably at least 4-fold, more preferably at least 5-fold, more preferably at least 10-fold, more preferably at least 20-fold, even more preferably at least 30-fold, most preferably at least 50-fold, and even most preferably at least 100-fold.

Cellulolytic activity: The term "cellulolytic activity" is defined herein as cellulase activity (e.g., endoglucanase(s), cellobiohydrolase(s), beta-glucosidase(s), or combinations thereof) that hydrolyzes a cellulose-containing material. Cellulolytic protein may hydrolyze or hydrolyzes carboxymethyl cellulose (CMC), thereby decreasing the viscosity of the incubation mixture. The resulting reduction in viscosity may be determined by a vibration viscosimeter (e.g., MIVI 3000 from Sofraser, France). Determination of cellulase activity, measured in terms of Cellulase Viscosity Unit (CEVU), quantifies the amount of catalytic activity present in a sample by measuring the ability of the sample to reduce the viscosity of a solution of carboxymethyl cellulose (CMC). The assay is performed at the temperature and pH suitable for the cellulolytic protein and substrate.

For purposes of the present invention, cellulolytic activity is determined by measuring the increase in hydrolysis of a cellulose-containing material by a cellulolytic composition under the following conditions: 1-50 mg of cellulolytic protein/g of cellulose in PCS for 1-7 day at 50° C. compared to a control hydrolysis without addition of cellulolytic protein.

Endoglucanase: The term "endoglucanase" is defined herein as an endo-1,4-(1,3;1,4)-beta-D-glucan 4-glucanohydrolase (E.C. No. 3.2.1.4), which catalyses endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. For purposes of the present invention, endoglucanase activity is determined using carboxymethyl cellulose (CMC) hydrolysis according to the procedure of Ghose, 1987, *Pure and Appl. Chem.* 59: 257-268.

The polypeptides having endoglucanase activity have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the endoglucanase activity of the mature polypeptide of SEQ ID NO: 2, 4, or 6.

Cellobiohydrolase: The term "cellobiohydrolase" is defined herein as a 1,4-beta-D-glucan cellobiohydrolase (E.C. 3.2.1.91), which catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain. For purposes of the present invention, cellobiohydrolase activity is determined according to the procedures described by Lever et al., 1972, *Anal. Biochem.* 47: 273-279 and by van Tilbeurgh et al., 1982, *FEBS Letters* 149: 152-156; van Tilbeurgh and Claeyssens, 1985, *FEBS Letters* 187: 283-288. In the present invention, the Lever et al. method was employed to assess hydrolysis of cellulose in corn stover, while the method of van Tilbeurgh et al. was used to determine the cellobiohydrolase activity on a fluorescent disaccharide derivative.

The polypeptides having cellobiohydrolase activity have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the cellobiohydrolase activity of the mature polypeptide of SEQ ID NO: 8 or 10.

Beta-glucosidase: The term "beta-glucosidase" is defined herein as a beta-D-glucoside glucohydrolase (E.C. 3.2.1.21), which catalyzes the hydrolysis of terminal non-reducing beta-D-glucose residues with the release of beta-D-glucose. For purposes of the present invention, beta-glucosidase activity is determined according to the basic procedure described by Venturi et al., 2002, *J. Basic Microbiol.* 42: 55-66, except different conditions were employed as described herein. One unit of beta-glucosidase activity is defined as 1.0 μmole of p-nitrophenol produced per minute at 50° C., pH 5 from 4 mM p-nitrophenyl-beta-D-glucopyranoside as substrate in 100 mM sodium citrate, 0.01% TWEEN® 20.

The polypeptides having beta-glucosidase activity have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the beta-glucosidase activity of the mature polypeptide of SEQ ID NO: 26, 28, or 30.

Family 7, 12, 45, or 61 glycoside hydrolase: The term "Family 7 glycoside hydrolase" or "Family GH7", "Family 12 glycoside hydrolase" or "Family GH12", "Family 45 glycoside hydrolase" or "Family GH45", and "Family 61 glycoside hydrolase" or "Family GH61" is defined herein as a polypeptide falling into the glycoside hydrolase Family 7, Family 12, Family 45, and Family 61, respectively, according to Henrissat, 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696. Presently, Henrissat lists the GH61 Family as unclassified indicating that properties such as mechanism, catalytic nucleophile/base, catalytic proton donors, and 3-D structure are not known for polypeptides belonging to this family. A GH7, GH12, or GH45 protein is also referred to as a CEL7, CEL12, or CEL45 protein, respectively.

Cellulose-containing material: The predominant polysaccharide in the primary cell wall of biomass is cellulose, the second most abundant is hemi-cellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

The cellulose-containing material can be any material containing cellulose. Cellulose is generally found, for example, in the stems, leaves, hulls, husks, and cobs of plants or leaves, branches, and wood of trees. The cellulose-containing material can be, but is not limited to, herbaceous material, agricultural residues, forestry residues, municipal solid wastes, waste paper, and pulp and paper mill residues. The cellulose-containing material can be any type of biomass including, but not limited to, wood resources, municipal solid waste, wastepaper, crops, and crop residues (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose-containing material is preferably in the form of lignocellulose, e.g., a plant cell wall material containing lignin, cellulose, and hemicellulose in a mixed matrix.

In a preferred aspect, the cellulose-containing material is corn stover. In another preferred aspect, the cellulose-containing material is corn fiber. In another preferred aspect, the cellulose-containing material is switch grass. In another preferred aspect, the cellulose-containing material is rice straw. In another preferred aspect, the cellulose-containing material is paper and pulp processing waste. In another preferred aspect, the cellulose-containing material is woody or herbaceous plants. In another preferred aspect, the cellulose-containing material is bagasse.

The cellulose-containing material may be used as is or may be subjected to pretreatment, using conventional methods known in the art. For example, physical pretreatment techniques can include various types of milling, irradiation, steaming/steam explosion, and hydrothermolysis; chemical pretreatment techniques can include dilute acid, alkaline, organic solvent, ammonia, sulfur dioxide, carbon dioxide, and pH-controlled hydrothermolysis; and biological pretreatment techniques can involve applying lignin-solubilizing microorganisms (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh, P., and Singh, A., 1993, Physicochemical and biological treatments for enzymatic/microbial conversion of lignocellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson, L., and Hahn-Hagerdal, B., 1996, Fermentation of lignocellulosic hydrolysates for ethanol production, *Enz. Microb. Tech.* 18: 312-331; and Vallander, L., and Eriksson, K.-E. L., 1990, Production of ethanol from lignocellulosic materials: State of the art, *Adv. Biochem. Eng./Biotechnol.* 42: 63-95).

Pre-treated corn stover: The term "PCS" or "Pre-treated Corn Stover" is defined herein as a cellulose-containing material derived from corn stover by treatment with heat and dilute acid. For purposes of the present invention, PCS is made by the method described in Example 1, or variations thereof in time, temperature and amount of acid.

Isolated polypeptide: The term "isolated polypeptide" as used herein refers to a polypeptide that is isolated from a source. In a preferred aspect, the polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

Substantially pure polypeptide: The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The polypeptides of the present invention are preferably in a substantially pure form, i.e., that the polypeptide preparation is essentially free of other polypeptide material with which it is natively or recombinantly associated. This can be accomplished, for example, by preparing the polypeptide by well-known recombinant methods or by classical purification methods.

Mature polypeptide: The term "mature polypeptide" is defined herein as a polypeptide having biological activity, e.g., enzyme activity, which is in its final form following translation and any post-translational modifications, such as N-terminal processing, C-terminal truncation, glycosylation, phosphorylation, etc.

Mature polypeptide coding sequence: The term "mature polypeptide coding sequence" is defined herein as a nucleotide sequence that encodes a mature polypeptide having biological activity.

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

Homologous sequence: The term "homologous sequence" is defined herein as sequences with an E value (or expectancy score) of less than 0.001 using the blastp (for protein databases) or tblastn (for nucleic acid databases) algorithms with the BLOSUM62 matrix, wordsize 3, gap existence cost 11, gap extension cost 1, no low complexity filtration, and a mature GH61, GH7, GH12, or GH45 protein sequence as query. See Altschul et al., 1997, *Nucleic Acids Res.* 25: 3389-3402.

Polypeptide Fragment The term "polypeptide fragment" is defined herein as a polypeptide having one or more (several) amino acids deleted from the amino and/or carboxyl terminus of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, or SEQ ID NO: 20, SEQ ID NO: 22, SEQ ID NO: 24, SEQ ID NO: 26, SEQ ID NO: 28, or SEQ ID NO: 30, or a homologous sequence thereof, wherein the fragment has activity as the mature polypeptide thereof. Preferably, a fragment of the mature polypeptide of SEQ ID NO: 2 contains at least 340 amino acid residues, more preferably at least 370 amino acid residues, and most preferably at least 400 amino acid residues. Preferably, a fragment of the mature polypeptide of SEQ ID NO: 4 contains at least 200 amino acid residues, more preferably at least 210 amino acid residues, and most preferably at least 220 amino acid residues. Preferably, a fragment of the mature polypeptide of SEQ ID NO: 6 contains at least 175 amino acid residues, more preferably at least 185 amino acid residues, and most preferably at least 195 amino acid residues. Preferably, a fragment of the mature polypeptide of SEQ ID NO: 8 contains at least 425 amino acid residues, more preferably at least 450 amino acid residues, and most preferably at least 475 amino acid residues. Preferably, a fragment of the mature polypeptide of SEQ ID NO: 10 contains at least 370 amino acid residues, more preferably at least 390 amino acid residues, and most preferably at least 410 amino acid residues. Preferably, a fragment of the mature polypeptide of SEQ ID NO: 12 contains at least 277 amino acid residues, more preferably at least 287 amino acid residues, and most preferably at least 297 amino acid residues. Preferably, a fragment of the mature polypeptide of SEQ ID NO: 14 contains at least 185 amino acid residues, more preferably at least 195 amino acid residues, and most preferably at least 205 amino acid residues. Preferably, a fragment of the mature polypeptide of SEQ ID NO: 16 contains at least 200 amino acid residues, more preferably at least 212 amino acid residues, and most preferably at least 224 amino acid residues. Preferably, a fragment of the mature polypeptide of SEQ ID NO: 18 contains at least 175 amino acid residues, more preferably at least 185 amino acid residues, and most preferably at least 195 amino acid residues. Preferably, a fragment of the mature polypeptide of SEQ ID NO: 20 contains at least 240 amino acid residues, more preferably at least 255 amino acid residues, and most preferably at least 270 amino acid residues. Preferably, a fragment of the mature polypeptide of SEQ ID NO: 22 contains at least 175 amino acid residues, more preferably at least 190 amino acid residues, and most preferably at least 205 amino acid residues. Preferably, a fragment of the mature polypeptide of SEQ ID NO: 24 contains at least 200 amino acid residues, more preferably at least 210 amino acid residues, and most preferably at least 220 amino acid residues. Preferably, a fragment of the mature polypeptide of SEQ ID NO: 26 contains at least 720 amino acid residues, more preferably at least 760 amino acid residues, and most preferably at least 800 amino acid residues. Preferably, a fragment of the mature polypeptide of SEQ ID NO: 28 contains at least 720 amino acid residues, more preferably at least 760 amino acid residues, and most preferably at least 800 amino acid residues. Preferably, a fragment of the mature polypeptide of SEQ ID NO: 30 contains at least 720 amino acid residues, more preferably at least 760 amino acid residues, and most preferably at least 800 amino acid residues.

Subsequence: The term "subsequence" is defined herein as a nucleotide sequence having one or more (several) nucleotides deleted from the 5' and/or 3' end of the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, or SEQ ID NO: 23; or a homologous sequence thereof; wherein the subsequence encodes a polypeptide fragment having activity as the mature polypeptide thereof. Preferably, a subsequence of the mature polypeptide coding sequence of SEQ ID NO: 1 contains at least 1020 nucleotides, more preferably at least 1110 nucleotides, and most preferably at least 1200 nucleotides. Preferably, a subsequence of the mature polypeptide coding sequence of SEQ ID NO: 3 contains at least 600 nucleotides, more preferably at least 630 nucleotides, and most preferably at least 660 nucleotides. Preferably, a subsequence of the mature polypeptide coding sequence of SEQ ID NO: 5 contains at least 525 nucleotides, more preferably at least 555 nucleotides, and most preferably at least 585 nucleotides. Preferably, a subsequence of the mature polypeptide coding sequence of SEQ ID NO: 7 contains at least 1275 nucleotides, more preferably at least 1350 nucleotides, and most preferably at least 1425 nucleotides. Preferably, a subsequence of the mature polypeptide coding sequence of SEQ ID NO: 9 contains at least 1110 nucleotides, more preferably at least 1170 nucleotides, and most preferably at least 1230 nucleotides. Preferably, a subsequence of the mature polypeptide coding sequence of SEQ ID NO: 11 contains at least 831 nucleotides, more preferably at least 861 nucleotides, and most preferably at least 891 nucleotides. Preferably, a subsequence of the mature polypeptide coding sequence of SEQ ID NO: 13 contains at least 555 nucleotides, more preferably at least 585 nucleotides, and most preferably at least 615 nucleotides. Preferably, a subsequence of the mature polypeptide coding sequence of SEQ ID NO: 15 contains at least 600 nucleotides, more preferably at least 636 nucleotides, and most preferably at least 672 nucleotides. Preferably, a subsequence of the mature polypeptide coding sequence of SEQ ID NO: 17 contains at least 525 nucleotides, more preferably at least 555 nucleotides, and most preferably at least 585 nucleotides. Preferably, a subsequence of the mature polypeptide coding sequence of SEQ ID NO: 19 contains at least 720 nucleotides, more preferably at least 765 nucleotides, and most preferably at least 810 nucleotides. Preferably, a subsequence of the mature polypeptide coding sequence of nucleotides 67 to 796 of SEQ ID NO: 21 contains at least 525 nucleotides, more preferably at least 570 nucleotides, and most preferably at least 615 nucleotides. Preferably, a subsequence of the mature polypeptide coding sequence of SEQ ID NO: 23 contains at least 600 nucleotides, more preferably at least 630 nucleotides, and most preferably at least 660 nucleotides. Preferably, a subsequence of the mature polypeptide coding sequence of SEQ ID NO: 25 contains at least 2160 nucleotides, more preferably at least 2280 nucleotides, and most preferably at least 2400 nucleotides. Preferably, a subsequence of the mature polypeptide coding sequence of SEQ ID NO: 27 contains at least 2160 nucleotides, more preferably at least 2280 nucleotides, and most preferably at least 2400 nucleotides. Preferably, a subsequence of the mature polypeptide coding sequence of SEQ ID NO: 29 contains at least 2160 nucleotides, more preferably at least 2280 nucleotides, and most preferably at least 2400 nucleotides.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide that is isolated from a source. In a preferred aspect, the polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant nucleotide sequence.

cDNA: The term "cDNA" is defined herein as a DNA molecule that can be prepared by reverse transcription from a mature, spliced, mRNA molecule obtained from a eukaryotic cell. cDNA lacks intron sequences that are usually present in the corresponding genomic DNA. The initial, primary RNA transcript is a precursor to mRNA that is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequence: The term "control sequences" is defined herein to include all components necessary for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the present invention and is operably linked to additional nucleotides that provide for its expression.

Host cell: The term "host cell", as used herein, includes any cell type that is susceptible to transformation, transfection, transduction, and the like with a nucleic acid construct or expression vector comprising a polynucleotide of the present invention.

Modification: The term "modification" means herein any chemical modification of the polypeptide consisting of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, or SEQ ID NO: 20, SEQ ID NO: 22, SEQ ID NO: 24, SEQ ID NO: 26, SEQ ID NO: 28, or SEQ ID NO: 30; or a homologous sequence thereof; as well as genetic manipulation of the DNA encoding such a polypeptide. The modification can be a substitution, a deletion and/or an insertion of one or more (several) amino acids as well as replacements of one or more (several) amino acid side chains.

Artificial variant: When used herein, the term "artificial variant" means a polypeptide produced by an organism expressing a modified nucleotide sequence of the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, or SEQ ID NO: 29; or a homologous sequence thereof. The modified nucleotide sequence is obtained through human intervention by modification of the polynucleotide sequence disclosed in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, or SEQ ID NO: 29; or a homologous sequence thereof.

DETAILED DESCRIPTION OF THE INVENTION

The present invention relates to methods for degrading or converting a cellulose-containing material, comprising: treating the cellulose-containing material with an effective amount of a cellulolytic enzyme composition comprising a polypeptide having cellulolytic enhancing activity, and one or more (several) components selected from the group consisting of a CEL7 polypeptide having endoglucanase activity, a CEL12 polypeptide having endoglucanase activity, a CEL45 polypeptide having endoglucanase activity, a CEL7 polypeptide having cellobiohydrolase activity with a cellulose binding domain, and a CEL7 polypeptide having cellobiohydrolase activity without a cellulose binding domain, wherein the presence of the polypeptide having cellulolytic enhancing activity increases the degradation of the cellulose-containing material by the cellulolytic enzyme composition compared to the absence of the polypeptide having cellulolytic enhancing activity.

The present invention further comprises recovering the degraded or converted cellulose-containing material. Soluble products of degradation or conversion of the cellulose-containing material can be separated from the insoluble cellulose-containing material using technology well known in the art such as centrifugation, filtration, and gravity settling.

The present invention also relates to methods for producing a substance, comprising: (a) saccharifying a cellulose-containing material with an effective amount of a cellulolytic enzyme composition comprising a polypeptide having cellulolytic enhancing activity, and one or more (several) components selected from the group consisting of a CEL7 polypeptide having endoglucanase activity, a CEL12 polypeptide having endoglucanase activity, a CEL45 polypeptide having endoglucanase activity, a CEL7 polypeptide having cellobiohydrolase activity with a cellulose binding domain, and a CEL7 polypeptide having cellobiohydrolase activity without a cellulose binding domain, wherein the presence of the polypeptide having cellulolytic enhancing activity increases the degradation of the cellulose-containing material by the cellulolytic enzyme composition compared to the absence of the polypeptide having cellulolytic enhancing activity; (b) fermenting the saccharified cellulose-containing material of step (a) with one or more (several) fermenting microorganisms to produce a fermentation product; and (c) recovering the fermentation product.

The present invention also relates to such cellulolytic enzyme compositions comprising an effective amount of a polypeptide having cellulolytic enhancing activity.

Cellulolytic Enzyme Compositions

The present invention also relates to cellulolytic enzyme compositions comprising a polypeptide having cellulolytic enhancing activity, and one or more (several) components selected from the group consisting of a CEL7 polypeptide having endoglucanase activity, a CEL12 polypeptide having endoglucanase activity, a CEL45 polypeptide having endoglucanase activity, a CEL7 polypeptide having cellobiohydrolase activity with a cellulose binding domain, and a CEL7 polypeptide having cellobiohydrolase activity without a cellulose binding domain.

In a first aspect, the isolated CEL7 polypeptide having endoglucanase activity comprises an amino acid sequence having a degree of sequence identity to the mature polypeptide of SEQ ID NO: 2 of preferably at least 70%, more preferably at least 75%, even more preferably at least 80%, even more preferably at least 85%, even more preferably at least 90%, most preferably at least 95%, and even most preferably at least 96%, 97%, 98%, or 99%, which have endoglucanase activity (hereinafter "homologous polypeptides"). In a preferred aspect, the homologous polypeptides comprise an amino acid sequence that differs by ten amino acids, preferably by five amino acids, more preferably by four amino acids, even more preferably by three amino acids, most preferably by two amino acids, and even most preferably by one amino acid from the mature polypeptide of SEQ ID NO: 2.

A CEL7 polypeptide having endoglucanase activity preferably comprises the amino acid sequence of SEQ ID NO: 2 or an allelic variant thereof; or a fragment thereof having endoglucanase activity. In a preferred aspect, the polypeptide comprises the amino acid sequence of SEQ ID NO: 2. In another preferred aspect, the polypeptide comprises the mature polypeptide of SEQ ID NO: 2. In another preferred aspect, the polypeptide comprises amino acids 21 to 456 of SEQ ID NO: 2, or an allelic variant thereof; or a fragment thereof having endoglucanase activity. In another preferred aspect, the polypeptide comprises amino acids 21 to 456 of SEQ ID NO: 2. In another preferred aspect, the polypeptide consists of the amino acid sequence of SEQ ID NO: 2 or an allelic variant thereof; or a fragment thereof having endoglucanase activity. In another preferred aspect, the polypeptide consists of the amino acid sequence of SEQ ID NO: 2. In another preferred aspect, the polypeptide consists of the mature polypeptide of SEQ ID NO: 2. In another preferred aspect, the polypeptide consists of amino acids 21 to 456 of SEQ ID NO: 2 or an allelic variant thereof; or a fragment thereof having endoglucanase activity. In another preferred aspect, the polypeptide consists of amino acids 21 to 456 of SEQ ID NO: 2.

A CEL7 polypeptide having endoglucanase activity can be obtained according to WO 1995/024471.

In another first aspect, the isolated CEL12 polypeptide having endoglucanase activity comprises an amino acid sequence having a degree of sequence identity to the mature polypeptide of SEQ ID NO: 4 of preferably at least 70%, more preferably at least 75%, even more preferably at least 80%, even more preferably at least 85%, even more preferably at least 90%, most preferably at least 95%, and even most preferably at least 96%, 97%, 98%, or 99%, which have endoglucanase activity (hereinafter "homologous polypeptides"). In a preferred aspect, the homologous polypeptides comprise an amino acid sequence that differs by ten amino acids, preferably by five amino acids, more preferably by four amino acids, even more preferably by three amino acids, most preferably by two amino acids, and even most preferably by one amino acid from the mature polypeptide of SEQ ID NO: 4.

A CEL12 polypeptide having endoglucanase activity preferably comprises the amino acid sequence of SEQ ID NO: 4 or an allelic variant thereof; or a fragment thereof having endoglucanase activity. In a preferred aspect, the polypeptide comprises the amino acid sequence of SEQ ID NO: 4. In another preferred aspect, the polypeptide comprises the mature polypeptide of SEQ ID NO: 4. In another preferred aspect, the polypeptide comprises amino acids 16 to 247 of SEQ ID NO: 4, or an allelic variant thereof; or a fragment thereof having endoglucanase activity. In another preferred aspect, the polypeptide comprises amino acids 16 to 247 of SEQ ID NO: 4. In another preferred aspect, the polypeptide consists of the amino acid sequence of SEQ ID NO: 4 or an allelic variant thereof; or a fragment thereof having endoglucanase activity. In another preferred aspect, the polypeptide consists of the amino acid sequence of SEQ ID NO: 4. In another preferred aspect, the polypeptide consists of the mature polypeptide of SEQ ID NO: 4. In another preferred aspect, the polypeptide consists of amino acids 16 to 247 of SEQ ID NO: 4 or an allelic variant thereof; or a fragment thereof having endoglucanase activity. In another preferred aspect, the polypeptide consists of amino acids 16 to 247 of SEQ ID NO: 4.

A CEL12 polypeptide having endoglucanase activity can be obtained according to WO 2001/25468.

In another first aspect, the isolated CEL45 polypeptide having endoglucanase activity comprises an amino acid sequence having a degree of sequence identity to the mature polypeptide of SEQ ID NO: 6 of preferably at least 70%, more preferably at least 75%, even more preferably at least 80%, even more preferably at least 85%, even more preferably at least 90%, most preferably at least 95%, and even most preferably at least 96%, 97%, 98%, or 99%, which have endoglucanase activity (hereinafter "homologous polypeptides"). In a preferred aspect, the homologous polypeptides comprise an amino acid sequence that differs by ten amino acids, preferably by five amino acids, more preferably by four amino acids, even more preferably by three amino acids, most preferably by two amino acids, and even most preferably by one amino acid from the mature polypeptide of SEQ ID NO: 6.

A CEL45 polypeptide having endoglucanase activity preferably comprises the amino acid sequence of SEQ ID NO: 6 or an allelic variant thereof; or a fragment thereof having endoglucanase activity. In a preferred aspect, the polypeptide comprises the amino acid sequence of SEQ ID NO: 6. In another preferred aspect, the polypeptide comprises the mature polypeptide of SEQ ID NO: 6. In another preferred aspect, the polypeptide comprises amino acids 19 to 225 of SEQ ID NO: 6, or an allelic variant thereof; or a fragment thereof having endoglucanase activity. In another preferred aspect, the polypeptide comprises amino acids 19 to 225 of SEQ ID NO: 6. In another preferred aspect, the polypeptide consists of the amino acid sequence of SEQ ID NO: 6 or an allelic variant thereof; or a fragment thereof having endoglucanase activity. In another preferred aspect, the polypeptide consists of the amino acid sequence of SEQ ID NO: 6. In another preferred aspect, the polypeptide consists of the mature polypeptide of SEQ ID NO: 6. In another preferred aspect, the polypeptide consists of amino acids 19 to 225 of SEQ ID NO: 6 or an allelic variant thereof; or a fragment thereof having endoglucanase activity. In another preferred aspect, the polypeptide consists of amino acids 19 to 225 of SEQ ID NO: 6.

A CEL45 polypeptide having endoglucanase activity can be obtained according to WO 2000/20555.

In another first aspect, the isolated CEL7 polypeptide having cellobiohydrolase activity with a cellulose binding domain comprises an amino acid sequence having a degree of sequence identity to the mature polypeptide of SEQ ID NO: 8 of preferably at least 70%, more preferably at least 75%, even more preferably at least 80%, even more preferably at least 85%, even more preferably at least 90%, most preferably at least 95%, and even most preferably at least 96%, 97%, 98%, or 99%, which have cellobiohydrolase activity (hereinafter "homologous polypeptides"). In a preferred aspect, the homologous polypeptides comprise an amino acid sequence that differs by ten amino acids, preferably by five amino acids, more preferably by four amino acids, even more preferably by three amino acids, most preferably by two amino acids, and even most preferably by one amino acid from the mature polypeptide of SEQ ID NO: 8.

A CEL7 polypeptide having cellobiohydrolase activity with a cellulose binding domain preferably comprises the amino acid sequence of SEQ ID NO: 8 or an allelic variant thereof; or a fragment thereof having cellobiohydrolase activity. In a preferred aspect, the polypeptide comprises the amino acid sequence of SEQ ID NO: 8. In another preferred aspect, the polypeptide comprises the mature polypeptide of SEQ ID NO: 8. In another preferred aspect, the polypeptide comprises amino acids 18 to 526 of SEQ ID NO: 8, or an allelic variant thereof; or a fragment thereof having cellobiohydrolase activity. In another preferred aspect, the polypeptide comprises amino acids 18 to 526 of SEQ ID NO: 8. In another preferred aspect, the polypeptide consists of the amino acid sequence of SEQ ID NO: 8 or an allelic variant thereof; or a fragment thereof having cellobiohydrolase activity. In another preferred aspect, the polypeptide consists of the amino acid sequence of SEQ ID NO: 8. In another preferred aspect, the polypeptide consists of the mature polypeptide of SEQ ID NO: 8. In another preferred aspect, the polypeptide consists of amino acids 18 to 526 of SEQ ID NO: 8 or an allelic variant thereof; or a fragment thereof having cellobiohydrolase activity. In another preferred aspect, the polypeptide consists of amino acids 18 to 526 of SEQ ID NO: 8.

A CEL7 polypeptide having cellobiohydrolase activity with a cellulose binding domain can be obtained according to WO 2001/79507.

In another first aspect, the isolated CEL7 polypeptide having cellobiohydrolase activity without a cellulose binding domain comprises an amino acid sequence having a degree of sequence identity to the mature polypeptide of SEQ ID NO: 10 of preferably at least 70%, more preferably at least 75%, even more preferably at least 80%, even more preferably at least 85%, even more preferably at least 90%, most preferably at least 95%, and even most preferably at least 96%, 97%, 98%, or 99%, which have cellobiohydrolase activity (hereinafter "homologous polypeptides"). In a preferred aspect, the homologous polypeptides comprise an amino acid sequence that differs by ten amino acids, preferably by five amino acids, more preferably by four amino acids, even more preferably by three amino acids, most preferably by two amino acids, and even most preferably by one amino acid from the mature polypeptide of SEQ ID NO: 10.

A CEL7 polypeptide having cellobiohydrolase activity without a cellulose binding domain preferably comprises the amino acid sequence of SEQ ID NO: 10 or an allelic variant thereof; or a fragment thereof having cellobiohydrolase activity. In a preferred aspect, the polypeptide comprises the amino acid sequence of SEQ ID NO: 10. In another preferred aspect, the polypeptide comprises the mature polypeptide of SEQ ID NO: 10. In another preferred aspect, the polypeptide comprises amino acids 21 to 450 of SEQ ID NO: 10, or an allelic variant thereof; or a fragment thereof having cellobiohydrolase activity. In another preferred aspect, the polypeptide comprises amino acids 21 to 450 of SEQ ID NO: 10. In another preferred aspect, the polypeptide consists of the amino acid sequence of SEQ ID NO: 10 or an allelic variant thereof; or a fragment thereof having cellobiohydrolase activity. In another preferred aspect, the polypeptide consists of the amino acid sequence of SEQ ID NO: 10. In another preferred aspect, the polypeptide consists of the mature polypeptide of SEQ ID NO: 10. In another preferred aspect, the polypeptide consists of amino acids 21 to 450 of SEQ ID NO: 10 or an allelic variant thereof; or a fragment thereof having cellobiohydrolase activity. In another preferred aspect, the polypeptide consists of amino acids 21 to 450 of SEQ ID NO: 10.

A CEL7 polypeptide having cellobiohydrolase activity without a cellulose binding domain can be obtained according to WO 2003/000941.

In a second aspect, the isolated CEL7 polypeptides having endoglucanase activity are encoded by polynucleotides that hybridize under at least very low stringency conditions, preferably at least low stringency conditions, more preferably at least medium stringency conditions, more preferably at least medium-high stringency conditions, even more preferably at least high stringency conditions, and most preferably at least very high stringency conditions with (i) the mature polypeptide coding sequence of SEQ ID NO: 1, (ii) the genomic DNA sequence comprising the mature polypeptide coding sequence of SEQ ID NO: 1, or (iii) a full-length complementary strand of (i) or (ii) (J. Sambrook, E. F. Fritsch, and T. Maniatus, 1989, *Molecular Cloning, A Laboratory Manual*, 2d edition, Cold Spring Harbor, N.Y.). In a preferred aspect, the mature polypeptide coding sequence is nucleotides 61 to 1368 of SEQ ID NO: 1.

In another second aspect, the isolated CEL12 polypeptides having endoglucanase activity are encoded by polynucleotides that hybridize under at least very low stringency conditions, preferably at least low stringency conditions, more preferably at least medium stringency conditions, more preferably at least medium-high stringency conditions, even more preferably at least high stringency conditions, and most preferably at least very high stringency conditions with (i) the mature polypeptide coding sequence of SEQ ID NO: 3, (ii) the genomic DNA sequence comprising the mature polypeptide coding sequence of SEQ ID NO: 3, or (iii) a full-length complementary strand of (i) or (ii). In a preferred aspect, the mature polypeptide coding sequence is nucleotides 46 to 741 of SEQ ID NO: 3.

In another second aspect, the isolated CEL45 polypeptides having endoglucanase activity are encoded by polynucleotides that hybridize under at least very low stringency conditions, preferably at least low stringency conditions, more preferably at least medium stringency conditions, more preferably at least medium-high stringency conditions, even more preferably at least high stringency conditions, and most preferably at least very high stringency conditions with (i) the mature polypeptide coding sequence of SEQ ID NO: 5, (ii) the cDNA sequence contained in the mature polypeptide coding sequence of SEQ ID NO: 5, or (iii) a full-length complementary strand of (i) or (ii). In a preferred aspect, the mature polypeptide coding sequence is nucleotides 55 to 675 of SEQ ID NO: 5.

In another second aspect, the isolated CEL7 polypeptides with a cellulose binding domain having cellobiohydrolase activity are encoded by polynucleotides that hybridize under at least very low stringency conditions, preferably at least low stringency conditions, more preferably at least medium stringency conditions, more preferably at least medium-high stringency conditions, even more preferably at least high stringency conditions, and most preferably at least very high stringency conditions with (i) the mature polypeptide coding sequence of SEQ ID NO: 7, (ii) the cDNA sequence contained in the mature polypeptide coding sequence of SEQ ID NO: 7, or (iii) a full-length complementary strand of (i) or (ii). In a preferred aspect, the mature polypeptide coding sequence is nucleotides 52 to 1645 of SEQ ID NO: 7.

In another second aspect, the isolated CEL7 polypeptides having cellobiohydrolase activity without a cellulose binding domain are encoded by polynucleotides that hybridize under at least very low stringency conditions, preferably at least low stringency conditions, more preferably at least medium stringency conditions, more preferably at least medium-high stringency conditions, even more preferably at least high stringency conditions, and most preferably at least very high stringency conditions with (i) the mature polypeptide coding sequence of SEQ ID NO: 9, (ii) the cDNA sequence contained in the mature polypeptide coding sequence of SEQ ID NO: 7, or (iii) a full-length complementary strand of (i) or (ii). In a preferred aspect, the mature polypeptide coding sequence is nucleotides 61 to 1350 of SEQ ID NO: 9.

The nucleotide sequence of SEQ ID NO: 1, SEQ ID NO: 3, SEQ ID NO: 5, SEQ ID NO: 7, or SEQ ID NO: 9, or a subsequence thereof; as well as the amino acid sequence of SEQ ID NO: 2, SEQ ID NO: 4, SEQ ID NO: 6, SEQ ID NO: 8, or SEQ ID NO: 10, or a fragment thereof, may be used to design a nucleic acid probe to identify and clone DNA encoding such polypeptides from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes which are at least 600 nucleotides, at least preferably at least 700 nucleotides, more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other organisms may, therefore, be screened for DNA that hybridizes with the probes described above and that encodes such polypeptides. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1, SEQ ID NO: 3, SEQ ID NO: 5, SEQ ID NO: 7, or SEQ ID NO: 9, or a subsequence thereof, the carrier material is preferably used in a Southern blot.

For purposes of the present invention, hybridization indicates that the nucleotide sequence hybridizes to a labeled nucleic acid probe corresponding to the mature polypeptide coding sequence of SEQ ID NO: 1, SEQ ID NO: 3, SEQ ID NO: 5, SEQ ID NO: 7, or SEQ ID NO: 9, the genomic DNA sequence comprising the mature polypeptide coding sequence of SEQ ID NO: 1, SEQ ID NO: 3, or SEQ ID NO: 9 or the cDNA sequence contained in the mature polypeptide coding sequence of SEQ ID NO: 5 or SEQ ID NO: 7; its full-length complementary strand, or a subsequence thereof, under very low to very high stringency conditions. Molecules to which the nucleic acid probe hybridizes under these conditions can be detected using, for example, X-ray film.

In a preferred aspect, the nucleic acid probe is the mature polypeptide coding sequence of SEQ ID NO: 1. In another preferred aspect, the nucleic acid probe is nucleotides 61 to 1368 of SEQ ID NO: 1. In another preferred aspect, the nucleic acid probe is a polynucleotide sequence that encodes the polypeptide of SEQ ID NO: 2, or a subsequence thereof. In another preferred aspect, the nucleic acid probe is SEQ ID NO: 1.

In another preferred aspect, the nucleic acid probe is the mature polypeptide coding sequence of SEQ ID NO: 3. In another preferred aspect, the nucleic acid probe is nucleotides 46 to 741 of SEQ ID NO: 3. In another preferred aspect, the nucleic acid probe is a polynucleotide sequence that encodes the polypeptide of SEQ ID NO: 4, or a subsequence thereof. In another preferred aspect, the nucleic acid probe is SEQ ID NO: 3.

In another preferred aspect, the nucleic acid probe is the mature polypeptide coding sequence of SEQ ID NO: 5. In another preferred aspect, the nucleic acid probe is nucleotides 55 to 675 of SEQ ID NO: 5. In another preferred aspect, the nucleic acid probe is a polynucleotide sequence that encodes the polypeptide of SEQ ID NO: 6, or a subsequence thereof. In another preferred aspect, the nucleic acid probe is SEQ ID NO: 5.

In another preferred aspect, the nucleic acid probe is the mature polypeptide coding sequence of SEQ ID NO: 7. In another preferred aspect, the nucleic acid probe is nucleotides 52 to 1645 of SEQ ID NO: 7. In another preferred aspect, the nucleic acid probe is a polynucleotide sequence that encodes the polypeptide of SEQ ID NO: 8, or a subsequence thereof. In another preferred aspect, the nucleic acid probe is SEQ ID NO: 7.

In another preferred aspect, the nucleic acid probe is the mature polypeptide coding sequence of SEQ ID NO: 9. In another preferred aspect, the nucleic acid probe is nucleotides 61 to 1350 of SEQ ID NO: 9. In another preferred aspect, the nucleic acid probe is a polynucleotide sequence that encodes the polypeptide of SEQ ID NO: 10, or a subsequence thereof. In another preferred aspect, the nucleic acid probe is SEQ ID NO: 9.

For long probes of at least 100 nucleotides in length, very low to very high stringency conditions are defined as prehybridization and hybridization at 42° C. in 5×SSPE, 0.3% SDS, 200 μg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes of about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes of about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third aspect, the isolated CEL7 polypeptides having endoglucanase activity are encoded by polynucleotides comprising or consisting of nucleotide sequences that have a degree of sequence identity to the mature polypeptide coding sequence of SEQ ID NO: 1 of preferably at least 70%, more preferably at least 75%, even more preferably at least 80%, even more preferably at least 85%, even more preferably at least 90%, most preferably at least 95%, and even most preferably at least 96%, 97%, 98%, or 99%, which encode an active polypeptide, which encode an active polypeptide.

In another third aspect, the isolated CEL12 polypeptides having endoglucanase activity are encoded by polynucleotides comprising or consisting of nucleotide sequences that have a degree of sequence identity to the mature polypeptide coding sequence of SEQ ID NO: 3 of preferably at least 70%, more preferably at least 75%, even more preferably at least 80%, even more preferably at least 85%, even more preferably at least 90%, most preferably at least 95%, and even most preferably at least 96%, 97%, 98%, or 99%, which encode an active polypeptide, which encode an active polypeptide.

In another third aspect, the isolated CEL45 polypeptides having endoglucanase activity are encoded by polynucleotides comprising or consisting of nucleotide sequences that have a degree of sequence identity to the mature polypeptide coding sequence of SEQ ID NO: 5 of preferably at least 70%, more preferably at least 75%, even more preferably at least 80%, even more preferably at least 85%, even more preferably at least 90%, most preferably at least 95%, and even most preferably at least 96%, 97%, 98%, or 99%, which encode an active polypeptide, which encode an active polypeptide.

In another third aspect, the isolated CEL7 polypeptides with a cellulose binding domain having cellobiohydrolase activity are encoded by polynucleotides comprising or consisting of nucleotide sequences that have a degree of sequence identity to the mature polypeptide coding sequence of SEQ ID NO: 7 of preferably at least 70%, more preferably at least 75%, even more preferably at least 80%, even more preferably at least 85%, even more preferably at least 90%, most preferably at least 95%, and even most preferably at least 96%, 97%, 98%, or 99%, which encode an active polypeptide, which encode an active polypeptide.

In another third aspect, the isolated CEL7 polypeptides having cellobiohydrolase activity without a cellulose binding domain are encoded by polynucleotides comprising or consisting of nucleotide sequences that have a degree of sequence identity to the mature polypeptide coding sequence of SEQ ID NO: 9 of preferably at least 70%, more preferably at least 75%, even more preferably at least 80%, even more preferably at least 85%, even more preferably at least 90%, most preferably at least 95%, and even most preferably at least 96%, 97%, 98%, or 99%, which encode an active polypeptide.

In a preferred aspect, the mature polypeptide coding sequence is nucleotides 61 to 1368 of SEQ ID NO: 1, nucleotides 46 to 741 of SEQ ID NO: 3, nucleotides 55 to 675 of SEQ ID NO: 5, nucleotides 52 to 1645 of SEQ ID NO: 7, or nucleotides 61 to 1350 of SEQ ID NO: 9. See polynucleotide section herein.

In a fourth aspect, the isolated CEL7 polypeptides having endoglucanase activity are artificial variants comprising a substitution, deletion, and/or insertion of one or more (or several) amino acids of the mature polypeptide of SEQ ID NO: 2; or a homologous sequence thereof.

In another fourth aspect, the CEL12 polypeptides having endoglucanase activity are artificial variants comprising a substitution, deletion, and/or insertion of one or more (or several) amino acids of the mature polypeptide of SEQ ID NO: 4; or a homologous sequence thereof.

In another fourth aspect, the isolated CEL45 polypeptides having endoglucanase activity are artificial variants comprising a substitution, deletion, and/or insertion of one or more (or several) amino acids of the mature polypeptide of SEQ ID NO: 6; or a homologous sequence thereof.

In another fourth aspect, the isolated CEL7 polypeptides with a cellulose binding domain having cellobiohydrolase activity are artificial variants comprising a substitution, deletion, and/or insertion of one or more (or several) amino acids of the mature polypeptide of SEQ ID NO: 8; or a homologous sequence thereof.

In another fourth aspect, the isolated CEL7 polypeptides having cellobiohydrolase activity without a cellulose binding domain are artificial variants comprising a substitution, deletion, and/or insertion of one or more (or several) amino acids of the mature polypeptide of SEQ ID NO: 10; or a homologous sequence thereof.

Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., endoglucanase or cellobiohydrolase activity) to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to a polypeptide according to the invention.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30: 10832-10837; U.S. Pat. No. 5,223,409; WO 92/06204), and region-directed mutagenesis (Derbyshire et al., 1986, *Gene* 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of the mature polypeptide of SEQ ID NO: 2, SEQ ID NO: 4, SEQ ID NO: 6, SEQ ID NO: 8, or SEQ ID NO: 10, is 10, preferably 9, more preferably 8, more preferably 7, more preferably at most 6, more preferably 5, more preferably 4, even more preferably 3, most preferably 2, and even most preferably 1.

The cellulolytic enzyme composition is added in amounts effective preferably from about 0.001% to about 10.0% wt. of solids, more preferably from about 0.01% to about 5.0% wt. of solids, even more preferably from about 0.025% to about 4.0% wt. of solids, and most preferably from about 0.005% to about 2.0% wt. of solids.

The cellulolytic enzyme composition of the present invention may be produced by fermentation of a microbial strain (wild-type or recombinant host cell) or by fermentation of several individual microbial strains (wild-type and/or recombinant host cells) and recovered as described herein.

The cellulolytic enzyme composition can also comprise other enzyme components involved in the degradation of cellulose-containing material, as described herein.

In a preferred aspect, the composition further comprises one or more (several) polypeptides having beta-glucosidase activity.

In a preferred aspect, the polypeptide having beta-glucosidase activity is obtained from *Aspergillus oryzae*. See WO 2002/095014. In another preferred aspect, the polypeptide having beta-glucosidase activity is obtained from *Aspergillus fumigatus*. See WO 2005/047499. In another preferred aspect, the polypeptide having beta-glucosidase activity is obtained from *Penicillium brasilianum*, e.g., *Penicillium brasilianum* strain IBT 20888. See WO 2007/019442.

The *Aspergillus oryzae* polypeptide having beta-glucosidase activity can be obtained according to WO 2002/095014. The *Aspergillus fumigatus* polypeptide having beta-glucosidase activity can be obtained according to WO 2005/047499. The *Penicillium brasilianum* polypeptide having beta-glucosidase activity can be obtained according to WO 2007/019442.

In a first aspect, the isolated polypeptides having beta-glucosidase activity comprise an amino acid sequence having a degree of sequence identity to the mature polypeptide of SEQ ID NO: 26, SEQ ID NO: 28, or SEQ ID NO: 30 of preferably at least 70%, more preferably at least 75%, more preferably at least 80%, even more preferably at least 85%, even more preferably at least 90%, most preferably at least 95%, and even most preferably at least 96%, 97%, 98%, or 99%, which have beta-glucosidase activity (hereinafter "homologous polypeptides"). In a preferred aspect, the homologous polypeptides comprise an amino acid sequence that differs by ten amino acids, preferably by five amino acids, more preferably by four amino acids, even more preferably by three amino acids, most preferably by two amino acids, and even most preferably by one amino acid from the mature polypeptide of SEQ ID NO: 26, SEQ ID NO: 28, or SEQ ID NO: 30.

A polypeptide having beta-glucosidase activity preferably comprises or consists of the amino acid sequence of SEQ ID NO: 26, SEQ ID NO: 28, or SEQ ID NO: 30 or an allelic variant thereof; or a fragment thereof having beta-glucosidase activity. In a preferred aspect, the polypeptide comprises or consists of the amino acid sequence of SEQ ID NO: 26, SEQ ID NO: 28, or SEQ ID NO: 30. In another preferred aspect, the polypeptide comprises or consists of the mature polypeptide of SEQ ID NO: 26, SEQ ID NO: 28, or SEQ ID NO: 30. In another preferred aspect, the polypeptide comprises or consists of amino acids 20 to 861 of SEQ ID NO: 26, or an allelic variant thereof; or a fragment thereof having beta-glucosidase activity. In another preferred aspect, the polypeptide comprises or consists of amino acids 20 to 863 of SEQ ID NO: 28, or an allelic variant thereof; or a fragment thereof having beta-glucosidase activity. In another preferred aspect, the polypeptide comprises or consists of amino acids 37 to 878 of SEQ ID NO: 30, or an allelic variant thereof; or a fragment thereof having beta-glucosidase activity. In another preferred aspect, the polypeptide comprises or consists of amino acids 20 to 861 of SEQ ID NO: 26. In another preferred aspect, the polypeptide comprises or consists of amino acids 20 to 863 of SEQ ID NO: 28. In another preferred aspect, the polypeptide comprises or consists of amino acids 37 to 878 of SEQ ID NO: 30.

In a second aspect, the isolated polypeptides having beta-glucosidase activity are encoded by polynucleotides that hybridize under at least very low stringency conditions, preferably at least low stringency conditions, more preferably at least medium stringency conditions, more preferably at least medium-high stringency conditions, even more preferably at least high stringency conditions, and most preferably at least very high stringency conditions with (i) the mature polypeptide coding sequence of SEQ ID NO: 25, SEQ ID NO: 27, or SEQ ID NO: 29, (ii) the cDNA sequence contained in the mature polypeptide coding sequence of SEQ ID NO: 25, SEQ ID NO: 27, or SEQ ID NO: 29, or (iii) a full-length complementary strand of (i) or (ii). In a preferred aspect, the mature polypeptide coding sequence is nucleotides 87 to 2612 of SEQ ID NO: 25, nucleotides 58 to 2580 of SEQ ID NO: 27, or nucleotides 171 to 2753 of SEQ ID NO: 29.

The nucleotide sequence of SEQ ID NO: 25, SEQ ID NO: 27, or SEQ ID NO: 29, or a subsequence thereof; as well as the amino acid sequence of SEQ ID NO: 25, SEQ ID NO: 27, or SEQ ID NO: 29, or a fragment thereof, may be used to design a nucleic acid probe to identify and clone DNA encoding polypeptides having beta-glucosidase activity from strains of different genera or species, as described supra.

For purposes of the present invention, hybridization indicates that the nucleotide sequence hybridizes to a labeled nucleic acid probe corresponding to the mature polypeptide coding sequence of SEQ ID NO: 25, SEQ ID NO: 27, or SEQ ID NO: 29, the cDNA sequence contained in the mature polypeptide coding sequence of SEQ ID NO: 25, SEQ ID NO: 27, or SEQ ID NO: 29, its complementary strand, or a subsequence thereof, under very low to very high stringency conditions, as described supra.

In a preferred aspect, the nucleic acid probe is the mature polypeptide coding sequence of SEQ ID NO: 25, SEQ ID NO: 27, or SEQ ID NO: 29. In another preferred aspect, the nucleic acid probe is nucleotides 87 to 2612 of SEQ ID NO: 25, nucleotides 58 to 2580 of SEQ ID NO: 27, or nucleotides 171 to 2753 of SEQ ID NO: 29. In another preferred aspect, the nucleic acid probe is a polynucleotide sequence that encodes the polypeptide of SEQ ID NO: 26, SEQ ID NO: 28, or SEQ ID NO: 30, or a subsequence thereof. In another preferred aspect, the nucleic acid probe is SEQ ID NO: 25, SEQ ID NO: 27, or SEQ ID NO: 29. In another preferred aspect, the nucleic acid probe is the polynucleotide sequence contained in the plasmid which is contained in *E. coli* DSM 14240, wherein the polynucleotide sequence thereof encodes a polypeptide having beta-glucosidase activity. In another preferred aspect, the nucleic acid probe is the polynucleotide sequence contained in plasmid pEJG113 which is contained in *E. coli* NRRL B-30695, wherein the polynucleotide sequence thereof encodes a polypeptide having beta-glucosidase activity. In another preferred aspect, the nucleic acid probe is the polynucleotide sequence contained in plasmid pKKAB which is contained in *E. coli* NRRL B-30860, wherein the polynucleotide sequence thereof encodes a polypeptide having beta-glucosidase activity. In another preferred aspect, the nucleic acid probe is the mature polypeptide coding region contained in the plasmid which is contained in *E. coli* DSM 14240. In another preferred aspect, the nucleic acid probe is the mature polypeptide coding region contained in plasmid pEJG113 which is contained in *E. coli* NRRL B-30695. In another preferred aspect, the nucleic acid probe is the mature polypeptide coding region contained in plasmid pKKAB which is contained in *E. coli* NRRL B-30860.

For long probes of at least 100 nucleotides in length, very low to very high stringency conditions are as defined herein.

For long probes of at least 100 nucleotides in length, the carrier material is finally washed as defined herein.

For short probes of about 15 nucleotides to about 70 nucleotides in length, stringency conditions are as defined herein.

For short probes of about 15 nucleotides to about 70 nucleotides in length, the carrier material is washed as defined herein.

In a third aspect, the polypeptides having beta-glucosidase activity are encoded by polynucleotides comprising or consisting of nucleotide sequences that have a degree of sequence identity to the mature polypeptide coding sequence of SEQ ID NO: 25, SEQ ID NO: 27, or SEQ ID NO: 29 of preferably at least 70%, more preferably at least 75%, more preferably at least 80%, even more preferably at least 85%, even more preferably at least 90%, most preferably at least 95%, and even most preferably at least 96%, 97%, 98%, or 99%, which encode an active polypeptide.

In a preferred aspect, the mature polypeptide coding sequence is nucleotides 87 to 2612 of SEQ ID NO: 25, nucleotides 58 to 2580 of SEQ ID NO: 27, or nucleotides 171 to 2753 of SEQ ID NO: 29.

In a fourth aspect, the polypeptides having beta-glucosidase activity are artificial variants comprising a substitution, deletion, and/or insertion of one or more (or several) amino acids of the mature polypeptide of SEQ ID NO: 26, SEQ ID NO: 28, or SEQ ID NO: 30; or a homologous sequence thereof. Methods for preparing such artificial variants are described supra.

The total number of amino acid substitutions, deletions and/or insertions of the mature polypeptide of SEQ ID NO: 26, SEQ ID NO: 28, or SEQ ID NO: 30, is 10, preferably 9, more preferably 8, more preferably 7, more preferably at most 6, more preferably 5, more preferably 4, even more preferably 3, most preferably 2, and even most preferably 1.

In another preferred aspect, the cellulolytic enzyme composition further comprises one or more additional enzyme activities selected from the group consisting of hemicellulases, esterases (e.g., lipases, phospholipases, and/or cutinases), proteases, laccases, and peroxidases. In the methods of the present invention, the additional enzyme(s) can be added prior to or during fermentation, including during or after propagation of the fermenting microorganism(s).

The enzymes can be derived or obtained from any suitable origin, including, bacterial, fungal, yeast, plant, or mammalian origin, as described herein. The term "obtained" means herein that the enzyme may have been isolated from an organism that naturally produces the enzyme as a native enzyme. The term "obtained" also means herein that the enzyme may have been produced recombinantly in a host organism employing methods described herein, wherein the recombinantly produced enzyme is either native or foreign to the host organism or has a modified amino acid sequence, e.g., having one or more amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

The enzymes used in the present invention can be in any form suitable for use in the methods described herein, such as a crude fermentation broth with or without cells or substantially pure polypeptides. The enzyme(s) can be a dry powder or granulate, a non-dusting granulate, a liquid, a stabilized liquid, or a protected enzyme(s). Granulates can be produced, e.g., as disclosed in U.S. Pat. Nos. 4,106,991 and 4,661,452, and can optionally be coated by process known in the art. Liquid enzyme preparations can, for instance, be stabilized by adding stabilizers such as a sugar, a sugar alcohol or another polyol, and/or lactic acid or another organic acid according to established process. Protected enzymes can be prepared according to the process disclosed in EP 238,216.

In a preferred aspect, the cellulolytic enzyme composition comprises a polypeptide having cellulolytic enhancing activity, and one or more (several) components selected from the group consisting of a CEL7 polypeptide having endoglucanase activity, a CEL12 polypeptide having endoglucanase activity, a CEL45 polypeptide having endoglucanase activity, a CEL7 polypeptide having cellobiohydrolase activity with a cellulose binding domain, and a CEL7 polypeptide having cellobiohydrolase activity without a cellulose binding domain.

In another preferred aspect, the cellulolytic enzyme composition comprises a polypeptide having cellulolytic enhancing activity, a polypeptide having beta-glucosidase activity, and one or more (several) components selected from the group consisting of a CEL7 polypeptide having endoglucanase activity, a CEL12 polypeptide having endoglucanase activity, a CEL45 polypeptide having endoglucanase activity, a CEL7 polypeptide having cellobiohydrolase activity with a cellulose binding domain, and a CEL7 polypeptide having cellobiohydrolase activity without a cellulose binding domain.

In another preferred aspect, the cellulolytic enzyme composition comprises a polypeptide having cellulolytic enhancing activity, a CEL7 polypeptide having endoglucanase activity, a CEL12 polypeptide having endoglucanase activity, a CEL45 polypeptide having endoglucanase activity, a CEL7 polypeptide having cellobiohydrolase activity with a cellulose binding domain, and a CEL7 polypeptide having cellobiohydrolase activity without a cellulose binding domain.

In another preferred aspect, the cellulolytic enzyme composition comprises a polypeptide having cellulolytic enhancing activity, a CEL7 polypeptide having endoglucanase activity, a CEL12 polypeptide having endoglucanase activity, a CEL45 polypeptide having endoglucanase activity, a CEL7 polypeptide having cellobiohydrolase activity with a cellulose binding domain, a CEL7 polypeptide having cellobiohydrolase activity without a cellulose binding domain, and a polypeptide having beta-glucosidase activity.

In another preferred aspect, the cellulolytic enzyme composition comprises a polypeptide having cellulolytic enhancing activity and a CEL7 polypeptide having endoglucanase activity.

In another preferred aspect, the cellulolytic enzyme composition comprises a polypeptide having cellulolytic enhancing activity and a CEL12 polypeptide having endoglucanase activity.

In another preferred aspect, the cellulolytic enzyme composition comprises a polypeptide having cellulolytic enhancing activity and a CEL45 polypeptide having endoglucanase activity.

In another preferred aspect, the cellulolytic enzyme composition comprises a polypeptide having cellulolytic enhancing activity and a CEL7 polypeptide having cellobiohydrolase activity with a cellulose binding domain.

In another preferred aspect, the cellulolytic enzyme composition comprises a polypeptide having cellulolytic enhancing activity and a CEL7 polypeptide having cellobiohydrolase activity without a cellulose binding domain.

In another preferred aspect, the cellulolytic enzyme composition comprises a polypeptide having cellulolytic enhancing activity, a CEL7 polypeptide having endoglucanase activity, and a polypeptide having beta-glucosidase activity.

In another preferred aspect, the cellulolytic enzyme composition comprises a polypeptide having cellulolytic enhancing activity, a CEL12 polypeptide having endoglucanase activity, and a polypeptide having beta-glucosidase activity.

In another preferred aspect, the cellulolytic enzyme composition comprises a polypeptide having cellulolytic enhancing activity, a CEL45 polypeptide having endoglucanase activity, and a polypeptide having beta-glucosidase activity.

In another preferred aspect, the cellulolytic enzyme composition comprises a polypeptide having cellulolytic enhancing activity, a CEL7 polypeptide having cellobiohydrolase activity with a cellulose binding domain, and a polypeptide having beta-glucosidase activity.

In another preferred aspect, the cellulolytic enzyme composition comprises a polypeptide having cellulolytic enhancing activity, a CEL7 polypeptide having cellobiohydrolase activity without a cellulose binding domain, and a polypeptide having beta-glucosidase activity.

In another preferred aspect, the cellulolytic enzyme composition comprises a polypeptide having cellulolytic enhancing activity, a CEL7 polypeptide having endoglucanase activity, and a CEL12 polypeptide having endoglucanase activity.

In another preferred aspect, the cellulolytic enzyme composition comprises a polypeptide having cellulolytic enhancing activity, a CEL7 polypeptide having endoglucanase activity, and a CEL45 polypeptide having endoglucanase activity.

In another preferred aspect, the cellulolytic enzyme composition comprises a polypeptide having cellulolytic enhancing activity, a CEL7 polypeptide having endoglucanase activity, and a CEL7 polypeptide having cellobiohydrolase activity with a cellulose binding domain.

In another preferred aspect, the cellulolytic enzyme composition comprises a polypeptide having cellulolytic enhancing activity, a CEL7 polypeptide having endoglucanase activity, and a CEL7 polypeptide having cellobiohydrolase activity without a cellulose binding domain.

In another preferred aspect, the cellulolytic enzyme composition comprises a polypeptide having cellulolytic enhancing activity, a CEL12 polypeptide having endoglucanase activity, and a CEL45 polypeptide having endoglucanase activity.

In another preferred aspect, the cellulolytic enzyme composition comprises a polypeptide having cellulolytic enhancing activity, a CEL12 polypeptide having endoglucanase activity, and a CEL7 polypeptide having cellobiohydrolase activity with a cellulose binding domain.

In another preferred aspect, the cellulolytic enzyme composition comprises a polypeptide having cellulolytic enhancing activity, a CEL12 polypeptide having endoglucanase activity, and a CEL7 polypeptide having cellobiohydrolase activity without a cellulose binding domain.

In another preferred aspect, the cellulolytic enzyme composition comprises a polypeptide having cellulolytic enhancing activity, a CEL7 polypeptide having cellobiohydrolase activity with a cellulose binding domain, and a CEL7 polypeptide having cellobiohydrolase activity without a cellulose binding domain.

In another preferred aspect, the cellulolytic enzyme composition comprises a polypeptide having cellulolytic enhancing activity, a CEL45 polypeptide having endoglucanase activity, and a CEL7 polypeptide having cellobiohydrolase activity with a cellulose binding domain.

In another preferred aspect, the cellulolytic enzyme composition comprises a polypeptide having cellulolytic enhancing activity, a CEL45 polypeptide having endoglucanase activity, and a CEL7 polypeptide having cellobiohydrolase activity without a cellulose binding domain.

In another preferred aspect, the cellulolytic enzyme composition comprises a polypeptide having cellulolytic enhancing activity, a CEL7 polypeptide having endoglucanase activity, a CEL12 polypeptide having endoglucanase activity, and a polypeptide having beta-glucosidase activity.

In another preferred aspect, the cellulolytic enzyme composition comprises a polypeptide having cellulolytic enhancing activity, a CEL7 polypeptide having endoglucanase activity, a CEL45 polypeptide having endoglucanase activity, and a polypeptide having beta-glucosidase activity.

In another preferred aspect, the cellulolytic enzyme composition comprises a polypeptide having cellulolytic enhancing activity, a CEL7 polypeptide having endoglucanase activity, a CEL7 polypeptide having cellobiohydrolase activity with a cellulose binding domain, and a polypeptide having beta-glucosidase activity.

In another preferred aspect, the cellulolytic enzyme composition comprises a polypeptide having cellulolytic enhancing activity, a CEL7 polypeptide having endoglucanase activity, a CEL7 polypeptide having cellobiohydrolase activity without a cellulose binding domain, and a polypeptide having beta-glucosidase activity.

In another preferred aspect, the cellulolytic enzyme composition comprises a polypeptide having cellulolytic enhancing activity, a CEL12 polypeptide having endoglucanase activity, a CEL45 polypeptide having endoglucanase activity, and a polypeptide having beta-glucosidase activity.

In another preferred aspect, the cellulolytic enzyme composition comprises a polypeptide having cellulolytic enhancing activity, a CEL12 polypeptide having endoglucanase activity, a CEL7 polypeptide having cellobiohydrolase activity with a cellulose binding domain, and a polypeptide having beta-glucosidase activity.

In another preferred aspect, the cellulolytic enzyme composition comprises a polypeptide having cellulolytic enhancing activity, a CEL12 polypeptide having endoglucanase activity, a CEL7 polypeptide having cellobiohydrolase activity without a cellulose binding domain, and a polypeptide having beta-glucosidase activity.

In another preferred aspect, the cellulolytic enzyme composition comprises a polypeptide having cellulolytic enhancing activity, a CEL7 polypeptide having cellobiohydrolase activity with a cellulose binding domain, a CEL7 polypeptide having cellobiohydrolase activity without a cellulose binding domain, and a polypeptide having beta-glucosidase activity.

In another preferred aspect, the cellulolytic enzyme composition comprises a polypeptide having cellulolytic enhancing activity, a CEL45 polypeptide having endoglucanase activity, a CEL7 polypeptide having cellobiohydrolase activity with a cellulose binding domain, and a polypeptide having beta-glucosidase activity.

In another preferred aspect, the cellulolytic enzyme composition comprises a polypeptide having cellulolytic enhancing activity, a CEL45 polypeptide having endoglucanase activity, a CEL7 polypeptide having cellobiohydrolase activity without a cellulose binding domain, and a polypeptide having beta-glucosidase activity.

In another preferred aspect, the cellulolytic enzyme composition comprises a polypeptide having cellulolytic enhancing activity, a CEL7 polypeptide having endoglucanase activity, a CEL12 polypeptide having endoglucanase activity, and a CEL45 polypeptide having endoglucanase activity.

In another preferred aspect, the cellulolytic enzyme composition comprises a polypeptide having cellulolytic enhancing activity, a CEL7 polypeptide having endoglucanase activity, a CEL12 polypeptide having endoglucanase activity, and a CEL7 polypeptide having cellobiohydrolase activity with a cellulose binding domain.

In another preferred aspect, the cellulolytic enzyme composition comprises a polypeptide having cellulolytic enhancing activity, a CEL7 polypeptide having endoglucanase activity, a CEL12 polypeptide having endoglucanase activity, and a CEL7 polypeptide having cellobiohydrolase activity without a cellulose binding domain.

In another preferred aspect, the cellulolytic enzyme composition comprises a polypeptide having cellulolytic enhancing activity, a CEL7 polypeptide having endoglucanase activity, a CEL12 polypeptide having endoglucanase activity, a CEL45 polypeptide having endoglucanase activity, and a CEL7 polypeptide having cellobiohydrolase activity with a cellulose binding domain.

In another preferred aspect, the cellulolytic enzyme composition comprises a polypeptide having cellulolytic enhancing activity, a CEL12 polypeptide having endoglucanase activity, a CEL45 polypeptide having endoglucanase activity, and a CEL7 polypeptide having cellobiohydrolase activity without a cellulose binding domain.

In another preferred aspect, the cellulolytic enzyme composition comprises a polypeptide having cellulolytic enhancing activity, a CEL7 polypeptide having endoglucanase activity, a CEL7 polypeptide having cellobiohydrolase activity with a cellulose binding domain, and a CEL7 polypeptide having cellobiohydrolase activity without a cellulose binding domain.

In another preferred aspect, the cellulolytic enzyme composition comprises a polypeptide having cellulolytic enhancing activity, a CEL45 polypeptide having endoglucanase activity, a CEL7 polypeptide having cellobiohydrolase activity with a cellulose binding domain, and a CEL7 polypeptide having cellobiohydrolase activity without a cellulose binding domain.

In another preferred aspect, the cellulolytic enzyme composition comprises a polypeptide having cellulolytic enhancing activity, a CEL12 polypeptide having endoglucanase activity, a CEL7 polypeptide having cellobiohydrolase activity with a cellulose binding domain, and a CEL7 polypeptide having cellobiohydrolase activity without a cellulose binding domain.

In another preferred aspect, the cellulolytic enzyme composition comprises a polypeptide having cellulolytic enhancing activity, a CEL7 polypeptide having endoglucanase activity, a CEL45 polypeptide having endoglucanase activity, and a CEL7 polypeptide having cellobiohydrolase activity with a cellulose binding domain.

In another preferred aspect, the cellulolytic enzyme composition comprises a polypeptide having cellulolytic enhancing activity, a CEL7 polypeptide having endoglucanase activity, a CEL45 polypeptide having endoglucanase activity, and a CEL7 polypeptide having cellobiohydrolase activity without a cellulose binding domain.

In another preferred aspect, the cellulolytic enzyme composition comprises a polypeptide having cellulolytic enhancing activity, a CEL7 polypeptide having endoglucanase activity, a CEL12 polypeptide having endoglucanase activity, a CEL45 polypeptide having endoglucanase activity, and a polypeptide having beta-glucosidase activity.

In another preferred aspect, the cellulolytic enzyme composition comprises a polypeptide having cellulolytic enhancing activity, a CEL7 polypeptide having endoglucanase activity, a CEL12 polypeptide having endoglucanase activity, a CEL7 polypeptide having cellobiohydrolase activity with a cellulose binding domain, and a polypeptide having beta-glucosidase activity.

In another preferred aspect, the cellulolytic enzyme composition comprises a polypeptide having cellulolytic enhancing activity, a CEL7 polypeptide having endoglucanase activity, a CEL12 polypeptide having endoglucanase activity, a CEL7 polypeptide having cellobiohydrolase activity without a cellulose binding domain, and a polypeptide having beta-glucosidase activity.

In another preferred aspect, the cellulolytic enzyme composition comprises a polypeptide having cellulolytic enhancing activity, a CEL12 polypeptide having endoglucanase activity, a CEL45 polypeptide having endoglucanase activity, a CEL7 polypeptide having cellobiohydrolase activity with a cellulose binding domain, and a polypeptide having beta-glucosidase activity.

In another preferred aspect, the cellulolytic enzyme composition comprises a polypeptide having cellulolytic enhancing activity, a CEL12 polypeptide having endoglucanase activity, a CEL45 polypeptide having endoglucanase activity, a CEL7 polypeptide having cellobiohydrolase activity without a cellulose binding domain, and a polypeptide having beta-glucosidase activity.

In another preferred aspect, the cellulolytic enzyme composition comprises a polypeptide having cellulolytic enhancing activity, a CEL7 polypeptide having endoglucanase activity, a CEL7 polypeptide having cellobiohydrolase activity with a cellulose binding domain, a CEL7 polypeptide having cellobiohydrolase activity without a cellulose binding domain, and a polypeptide having beta-glucosidase activity.

In another preferred aspect, the cellulolytic enzyme composition comprises a polypeptide having cellulolytic enhancing activity, a CEL45 polypeptide having endoglucanase activity, a CEL7 polypeptide having cellobiohydrolase activity with a cellulose binding domain, a CEL7 polypeptide having cellobiohydrolase activity without a cellulose binding domain, and a polypeptide having beta-glucosidase activity.

In another preferred aspect, the cellulolytic enzyme composition comprises a polypeptide having cellulolytic enhancing activity, a CEL12 polypeptide having endoglucanase activity, a CEL7 polypeptide having cellobiohydrolase activity with a cellulose binding domain, a CEL7 polypeptide having cellobiohydrolase activity without a cellulose binding domain, and a polypeptide having beta-glucosidase activity.

In another preferred aspect, the cellulolytic enzyme composition comprises a polypeptide having cellulolytic enhancing activity, a CEL7 polypeptide having endoglucanase activity, a CEL45 polypeptide having endoglucanase activity, a CEL7 polypeptide having cellobiohydrolase activity with a cellulose binding domain, and a polypeptide having beta-glucosidase activity.

In another preferred aspect, the cellulolytic enzyme composition comprises a polypeptide having cellulolytic enhancing activity, a CEL7 polypeptide having endoglucanase activity, a CEL45 polypeptide having endoglucanase activity, a CEL7 polypeptide having cellobiohydrolase activity without a cellulose binding domain, and a polypeptide having beta-glucosidase activity.

In another preferred aspect, the cellulolytic enzyme composition comprises a polypeptide having cellulolytic enhancing activity, a CEL7 polypeptide having endoglucanase activity, a CEL12 polypeptide having endoglucanase activity, a CEL45 polypeptide having endoglucanase activity, and a CEL7 polypeptide having cellobiohydrolase activity with a cellulose binding domain.

In another preferred aspect, the cellulolytic enzyme composition comprises a polypeptide having cellulolytic enhancing activity, a CEL7 polypeptide having endoglucanase activity, a CEL12 polypeptide having endoglucanase activity, a CEL45 polypeptide having endoglucanase activity, and a CEL7 polypeptide having cellobiohydrolase activity without a cellulose binding domain.

In another preferred aspect, the cellulolytic enzyme composition comprises a polypeptide having cellulolytic enhancing activity, a CEL7 polypeptide having endoglucanase activity, a CEL12 polypeptide having endoglucanase activity, a CEL7 polypeptide having cellobiohydrolase activity with a cellulose binding domain, and a CEL7 polypeptide having cellobiohydrolase activity without a cellulose binding domain.

In another preferred aspect, the cellulolytic enzyme composition comprises a polypeptide having cellulolytic enhancing activity, a CEL7 polypeptide having endoglucanase activity, a CEL45 polypeptide having endoglucanase activity, a CEL7 polypeptide having cellobiohydrolase activity with a cellulose binding domain, and a CEL7 polypeptide having cellobiohydrolase activity without a cellulose binding domain.

In another preferred aspect, the cellulolytic enzyme composition comprises a polypeptide having cellulolytic enhancing activity, a CEL12 polypeptide having endoglucanase activity, a CEL45 polypeptide having endoglucanase activity, a CEL7 polypeptide having cellobiohydrolase activity with a cellulose binding domain, and a CEL7 polypeptide having cellobiohydrolase activity without a cellulose binding domain.

In another preferred aspect, the cellulolytic enzyme composition comprises a polypeptide having cellulolytic enhancing activity, a CEL7 polypeptide having endoglucanase activity, a CEL12 polypeptide having endoglucanase activity, a CEL45 polypeptide having endoglucanase activity, a CEL7 polypeptide having cellobiohydrolase activity with a cellulose binding domain, and a polypeptide having beta-glucosidase activity.

In another preferred aspect, the cellulolytic enzyme composition comprises a polypeptide having cellulolytic enhancing activity, a CEL7 polypeptide having endoglucanase activity, a CEL12 polypeptide having endoglucanase activity, a CEL45 polypeptide having endoglucanase activity, a CEL7 polypeptide having cellobiohydrolase activity without a cellulose binding domain, and a polypeptide having beta-glucosidase activity.

In another preferred aspect, the cellulolytic enzyme composition comprises a polypeptide having cellulolytic enhancing activity, a CEL7 polypeptide having endoglucanase activity, a CEL12 polypeptide having endoglucanase activity, a CEL7 polypeptide having cellobiohydrolase activity with a cellulose binding domain, a CEL7 polypeptide having cellobiohydrolase activity without a cellulose binding domain, and a polypeptide having beta-glucosidase activity.

In another preferred aspect, the cellulolytic enzyme composition comprises a polypeptide having cellulolytic enhancing activity, a CEL7 polypeptide having endoglucanase activity, a CEL45 polypeptide having endoglucanase activity, a CEL7 polypeptide having cellobiohydrolase activity with a cellulose binding domain, a CEL7 polypeptide having cellobiohydrolase activity without a cellulose binding domain, and a polypeptide having beta-glucosidase activity.

In another preferred aspect, the cellulolytic enzyme composition comprises a polypeptide having cellulolytic enhancing activity, a CEL12 polypeptide having endoglucanase activity, a CEL45 polypeptide having endoglucanase activity, a CEL7 polypeptide having cellobiohydrolase activity with a cellulose binding domain, a CEL7 polypeptide having cellobiohydrolase activity without a cellulose binding domain, and a polypeptide having beta-glucosidase activity.

Sources of Polypeptides Having Endoglucanase, Cellobiohydrolase, or Beta-Glucosidase Activity A CEL7 polypeptide having endoglucanase activity, CEL12 polypeptide having endoglucanase activity, CEL45 polypeptide having endoglucanase activity, CEL7 polypeptide having cellobiohydrolase activity with a cellulose binding domain, or CEL7 polypeptide having cellobiohydrolase activity without a cellulose binding domain, as well as polypeptide having beta-glucosidase activity, may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A CEL7 polypeptide having endoglucanase activity, CEL12 polypeptide having endoglucanase activity, CEL45 polypeptide having endoglucanase activity, CEL7 polypeptide having cellobiohydrolase activity with a cellulose binding domain, and/or CEL7 polypeptide having cellobiohydrolase activity without a cellulose binding domain may be obtained from FIBREZYME® LDI, FIBREZYME® LBR, or VISCOSTAR® 150L (Dyadic International, Inc., Jupiter, Fla., USA).

A CEL7 polypeptide having endoglucanase activity, CEL12 polypeptide having endoglucanase activity, CEL45 polypeptide having endoglucanase activity, CEL7 polypeptide having cellobiohydrolase activity with a cellulose binding domain, CEL7 polypeptide having cellobiohydrolase activity without a cellulose binding domain, or polypeptide having beta-glucosidase activity may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus*, or *Oceanobacillus* polypeptide, or a Gram negative bacterial polypeptide such as an *E. coli, Pseudomonas, Salmonella, Campylobacter, Helicobacter, Flavobacterium, Fusobacterium, Ilyobacter, Neisseria*, or *Ureaplasma* polypeptide.

In a preferred aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* polypeptide.

In another preferred aspect, the polypeptide is a *Streptococcus equisimilis, Streptococcus pyogenes, Streptococcus uberis*, or *Streptococcus equi* subsp. *Zooepidemicus* polypeptide.

In another preferred aspect, the polypeptide is a *Streptomyces achromogenes, Streptomyces avermitilis, Streptomyces coelicolor, Streptomyces griseus*, or *Streptomyces lividans* polypeptide.

The CEL12 polypeptide having endoglucanase activity, CEL45 polypeptide having endoglucanase activity, CEL7 polypeptide having cellobiohydrolase activity with a cellulose binding domain, CEL7 polypeptide having cellobiohydrolase activity without a cellulose binding domain, or polypeptide having beta-glucosidase activity may also be a fungal polypeptide, and more preferably a yeast polypeptide such as a *Candida, Kluyveromyces, Pichia, Saccharomyces, Schizosaccharomyces*, or *Yarrowia* polypeptide; or more preferably a filamentous fungal polypeptide such as an *Acremonium, Aspergillus, Aureobasidium, Chrysosporium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium*, or *Trichoderma* polypeptide.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide.

In another preferred aspect, the polypeptide is an *Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium lucknowense, Coprinus cinereus, Diplodia gossypina, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Magnaporthe grisea, Mucor miehei, Myceliophthora thermophila Neurospora crassa, Penicillium purpurogenum, Phanerochaete chrysosporium, Pseudoplectania nigrella, Thermoascus aurantiacus, Thielavia terrestris, Trichoderma harzianum, Trichoderma koningii, Trichoderma longibrachiatum, Trichoderma reesei, Trichoderma viride*, or *Trichophaea saccata* polypeptide.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide sequence encoding a polypeptide has been detected with the probe(s), the polynucleotide can be isolated or cloned by utilizing techniques which are well known to those of ordinary skill in the art (see, e.g., Sambrook et al., 1989, supra).

The polypeptides can also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

A fusion polypeptide can further comprise a cleavage site. Upon secretion of the fusion protein, the site is cleaved releasing the polypeptide having activity from the fusion protein. Examples of cleavage sites include, but are not limited to, a Kex2 site that encodes the dipeptide Lys-Arg (Martin et al., 2003, *J. Ind. Microbiol. Biotechnol.* 3: 568-76; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381), an Ile-(Glu or Asp)-Gly-Arg site, which is cleaved by a Factor Xa protease after the arginine residue (Eaton et al., 1986, *Biochem.* 25: 505-512); a Asp-Asp-Asp-Asp-Lys site, which is cleaved by an enterokinase after the lysine (Collins-Racie et al., 1995, *Biotechnology* 13: 982-987); a His-Tyr-Glu site or His-Tyr-Asp site, which is cleaved by Genenase I (Carter et al., 1989, *Proteins: Structure, Function, and Genetics* 6: 240-248); a Leu-Val-Pro-Arg-Gly-Ser site, which is cleaved by thrombin after the Arg (Stevens, 2003, *Drug Discovery World* 4: 35-48); a Glu-Asn-Leu-Tyr-Phe-Gln-Gly site, which is cleaved by TEV protease after the Gln (Stevens, 2003, supra); and a Leu-Glu-Val-Leu-Phe-Gln-Gly-Pro site, which is cleaved by a genetically engineered form of human rhinovirus 3C protease after the Gln (Stevens, 2003, supra).

Polynucleotides Encoding Polypeptides Having Endoglucanase or Cellobiohydrolase Activity Polynucleotides comprising or consisting of nucleotide sequences that encode CEL7 polypeptides having endoglucanase activity, CEL12 polypeptides having endoglucanase activity, CEL45 polypeptides having endoglucanase activity, CEL7 polypeptides with a cellulose binding domain having cellobiohydrolase activity, or CEL7 polypeptides having cellobiohydrolase activity without a cellulose binding domain can be isolated and utilized to practice the methods of the present invention, as described herein.

The polynucleotides comprise or consist of nucleotide sequences that have a degree of sequence identity to the mature polypeptide coding sequence of SEQ ID NO: 1, SEQ ID NO: 3, SEQ ID NO: 5, SEQ ID NO: 7, or SEQ ID NO: 9 of preferably at least 70%, more preferably at least 75%, even more preferably at least 80%, even more preferably at least 85%, even more preferably at least 90%, most preferably at least 95%, and even most preferably at least 96%, 97%, 98%, or 99% identity, which encode polypeptides having enzyme activity.

In a preferred aspect, the nucleotide sequence encoding a CEL7 polypeptide having endoglucanase activity comprises or consists of SEQ ID NO: 1. In another preferred aspect, the nucleotide sequence comprises or consists of the mature polypeptide coding region of SEQ ID NO: 1. The present invention also encompasses nucleotide sequences that encode a polypeptide comprising or consisting of the amino acid sequence of SEQ ID NO: 2 or the mature polypeptide thereof, which differ from SEQ ID NO: 1 by virtue of the degeneracy of the genetic code. The present invention also relates to subsequences of SEQ ID NO: 1 that encode fragments of SEQ ID NO: 2 having CEL7 endoglucanase activity.

In another preferred aspect, the nucleotide sequence encoding a CEL12 polypeptide having endoglucanase activity comprises or consists of SEQ ID NO: 3. In another preferred aspect, the nucleotide sequence comprises or consists of the mature polypeptide coding region of SEQ ID NO: 3. The present invention also encompasses nucleotide sequences that encode a polypeptide comprising or consisting of the amino acid sequence of SEQ ID NO: 4 or the mature polypeptide thereof, which differ from SEQ ID NO: 3 by virtue of the degeneracy of the genetic code. The present invention also relates to subsequences of SEQ ID NO: 3 that encode fragments of SEQ ID NO: 4 having CEL12 endoglucanase activity.

In another preferred aspect, the nucleotide sequence encoding a CEL45 polypeptide having endoglucanase activity comprises or consists of SEQ ID NO: 5. In another preferred aspect, the nucleotide sequence is the mature polypeptide coding region of SEQ ID NO: 5. The present invention also encompasses nucleotide sequences that encode a polypeptide comprising or consisting of the amino acid sequence of SEQ ID NO: 6 or the mature polypeptide thereof, which differ from SEQ ID NO: 5 by virtue of the degeneracy of the genetic code. The present invention also relates to subsequences of SEQ ID NO: 5 that encode fragments of SEQ ID NO: 6 having CEL45 endoglucanase activity.

In another preferred aspect, the nucleotide sequence encoding a CEL7 polypeptide having cellobiohydrolase activity with a cellulose binding domain comprises or consists of SEQ ID NO: 7. In another preferred aspect, the nucleotide sequence comprises or consists of the mature polypeptide coding region of SEQ ID NO: 7. The present invention also encompasses nucleotide sequences that encode a polypeptide comprising or consisting of the amino acid sequence of SEQ ID NO: 8 or the mature polypeptide thereof, which differ from SEQ ID NO: 7 by virtue of the degeneracy of the genetic code. The present invention also relates to subsequences of SEQ ID NO: 7 that encode fragments of SEQ ID NO: 16 having CEL7 cellobiohydrolase activity.

In another preferred aspect, the nucleotide sequence encoding a CEL7 polypeptide having cellobiohydrolase activity without a cellulose binding domain comprises or consists of SEQ ID NO: 9. In another preferred aspect, the nucleotide sequence comprises or consists of the mature polypeptide coding region of SEQ ID NO: 9. The present invention also encompasses nucleotide sequences that encode a polypeptide comprising or consisting of the amino acid sequence of SEQ ID NO: 10 or the mature polypeptide thereof, which differ from SEQ ID NO: 9 by virtue of the degeneracy of the genetic code. The present invention also relates to subsequences of SEQ ID NO: 9 that encode fragments of SEQ ID NO: 18 having CEL7 cellobiohydrolase activity.

The present invention also relates to mutant polynucleotides comprising at least one mutation in the mature polypeptide coding sequence of SEQ ID NO: 1, SEQ ID NO: 3, SEQ ID NO: 5, SEQ ID NO: 7, or SEQ ID NO: 9, in which the mutant nucleotide sequence encodes the mature polypeptide of SEQ ID NO: 2, SEQ ID NO: 4, SEQ ID NO: 6, SEQ ID NO: 8, or SEQ ID NO: 10. In a preferred aspect, the mature polypeptide is amino acids 21 to 456 of SEQ ID NO: 2, amino acids 16 to 247 of SEQ ID NO: 4, amino acids 19 to 225 of SEQ ID NO: 6, amino acids 18 to 526 of SEQ ID NO: 8, or amino acids 21 to 450 of SEQ ID NO: 10. In another preferred aspect, the mature polypeptide coding sequence is nucleotides 61 to 1368 of SEQ ID NO: 1, nucleotides 46 to 741 of SEQ ID NO: 3, nucleotides 55 to 675 of SEQ ID NO: 5, nucleotides 52 to 1645 of SEQ ID NO: 7, or nucleotides 61 to 1350 of SEQ ID NO: 9.

The techniques used to isolate or clone a polynucleotide encoding such a polypeptide are known in the art and include isolation from genomic DNA, preparation from cDNA, or a combination thereof. The cloning of the polynucleotides from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be an allelic or species variant of the polypeptide encoding region of the nucleotide sequence.

The polynucleotide may also be a polynucleotide encoding a polypeptide having endoglucanase or cellobiohydrolase activity that hybridize under at least very low stringency conditions, preferably at least low stringency conditions, more preferably at least medium stringency conditions, more preferably at least medium-high stringency conditions, even more preferably at least high stringency conditions, and most preferably at least very high stringency conditions with (i) the mature polypeptide coding sequence of SEQ ID NO: 1, SEQ ID NO: 3, SEQ ID NO: 5, SEQ ID NO: 7, or SEQ ID NO: 9, (ii) the genomic DNA sequence comprising the mature polypeptide coding sequence of SEQ ID NO: 1, SEQ ID NO: 3, or SEQ ID NO: 9 or the cDNA sequence contained in the mature polypeptide coding sequence of SEQ ID NO: 5 or SEQ ID NO: 7, or (iii) a full-length complementary strand of (i) or (ii); or allelic variants and subsequences thereof (Sambrook et al., 1989, supra), as defined herein.

In a preferred aspect, the mature polypeptide coding sequence is nucleotides 61 to 1368 of SEQ ID NO: 1, nucleotides 46 to 741 of SEQ ID NO: 3, nucleotides 55 to 675 of SEQ ID NO: 5, nucleotides 52 to 1645 of SEQ ID NO: 7, or nucleotides 61 to 1350 of SEQ ID NO: 9.

Polynucleotides Encoding Polypeptides Having Beta-Glucosidase Activity

Polynucleotides comprising or consisting of nucleotide sequences that encode polypeptides having beta-glucosidase activity can be isolated and utilized to practice the methods of the present invention, as described herein.

The polynucleotides comprise or consist of nucleotide sequences that have a degree of sequence identity to the mature polypeptide coding sequence of SEQ ID NO: 25, SEQ ID NO: 27, or SEQ ID NO: 29 of preferably at least 70%, more preferably at least 75%, even more preferably at least 80%, even more preferably at least 85%, even more preferably at least 90%, most preferably at least 95%, and even most preferably at least 96%, 97%, 98%, or 99% identity, which encode polypeptides having enzyme activity.

In a preferred aspect, the nucleotide sequence encoding a polypeptide having beta-glucosidase activity comprises or consists of SEQ ID NO: 25, SEQ ID NO: 27, or SEQ ID NO: 29. In another preferred aspect, the nucleotide sequence comprises or consists of the mature polypeptide coding region of SEQ ID NO: 25, SEQ ID NO: 27, or SEQ ID NO: 29. The present invention also encompasses nucleotide sequences that encode a polypeptide comprising or consisting of the amino acid sequence of SEQ ID NO: 26, SEQ ID NO: 28, or SEQ ID NO: 30 or the mature polypeptide thereof, which differ from SEQ ID NO: 25, SEQ ID NO: 27, or SEQ ID NO: 29, respectively, by virtue of the degeneracy of the genetic code. The present invention also relates to subsequences of SEQ ID NO: 25, SEQ ID NO: 27, or SEQ ID NO: 29 that encode fragments of SEQ ID NO: 26, SEQ ID NO: 28, or SEQ ID NO: 30 having beta-glucosidase activity.

The present invention also relates to mutant polynucleotides comprising at least one mutation in the mature polypeptide coding sequence of SEQ ID NO: 25, SEQ ID NO: 27, or SEQ ID NO: 29, in which the mutant nucleotide sequence encodes the mature polypeptide of SEQ ID NO: 26, SEQ ID NO: 28, or SEQ ID NO: 30. In a preferred aspect, the mature polypeptide is amino acids 20 to 861 of SEQ ID NO: 26, amino acids 20 to 863 of SEQ ID NO: 28, or amino acids 37 to 878 of SEQ ID NO: 30. In another preferred aspect, the mature polypeptide coding sequence is nucleotides 87 to 2612 of SEQ ID NO: 25, nucleotides 58 to 2580 of SEQ ID NO: 27, or nucleotides 171 to 2753 of SEQ ID NO: 29.

The techniques used to isolate or clone a polynucleotide encoding such a polypeptide are known in the art and include isolation from genomic DNA, preparation from cDNA, or a combination thereof, as described supra.

The polynucleotide may also be a polynucleotide encoding a polypeptide having beta-glucosidase activity that hybridize under at least very low stringency conditions, preferably at least low stringency conditions, more preferably at least medium stringency conditions, more preferably at least medium-high stringency conditions, even more preferably at least high stringency conditions, and most preferably at least very high stringency conditions with (i) the mature polypeptide coding sequence of SEQ ID NO: 25, SEQ ID NO: 27, or SEQ ID NO: 29, (ii) the cDNA sequence contained in the mature polypeptide coding sequence of SEQ ID NO: 25, SEQ ID NO: 27, or SEQ ID NO: 29, or (iii) a full-length complementary strand of (i) or (ii); or allelic variants and subsequences thereof, as defined herein.

In a preferred aspect, the mature polypeptide coding sequence is nucleotides 87 to 2612 of SEQ ID NO: 25, nucleotides 58 to 2580 of SEQ ID NO: 27, or nucleotides 171 to 2753 of SEQ ID NO: 29.

Polypeptides Having Cellulolytic Enhancing Activity

In a first aspect, the isolated polypeptides having cellulolytic enhancing activity comprise the following motifs:
[ILMV]-P-X(4,5)-G-X-Y-[ILMV]-X-R-X-[EQ]-X(4)-
  [HNQ] (SEQ ID NO: 125 or SEQ ID NO: 126) and [FW]-
  [TF]-K-[AIV](SEQ ID NO: 41),
wherein X is any amino acid, X(4,5) is any amino acid at 4 or 5 contiguous positions, and X(4) is any amino acid at 4 contiguous positions.

The isolated polypeptide comprising the above-noted motifs may further comprise:
  H-X(1,2)-G-P-X(3)-[YW]-[AILMV](SEQ ID NO: 33 or SEQ ID NO: 34)
  [EQ]-X-Y-X(2)-C-X-[EHQN]-[FILV]-X-[ILV](SEQ ID NO: 35) or
  H-X(1,2)-G-P-X(3)-[YW]-[AILMV] (SEQ ID NO: 36 or SEQ ID NO: 37) and [EQ]-X-Y-X(2)-C-X-[EHQN]-[FILV]-X-[ILV](SEQ ID NO: 38)
wherein X is any amino acid, X(1,2) is any amino acid at 1 position or 2 contiguous positions, X(3) is any amino acid at 3 contiguous positions, and X(2) is any amino acid at 2 contiguous positions. In the above motifs, the accepted IUPAC single letter amino acid abbreviation is employed.

In a preferred aspect, the isolated polypeptide having cellulolytic enhancing activity further comprises H-X(1,2)-G-P-X(3)-[YW]-[AILMV](SEQ ID NO: 33 or SEQ ID NO: 34). In another preferred aspect, the isolated polypeptide having cellulolytic enhancing activity further comprises [EQ]-X-Y-X(2)-C-X-[EHQN]-[FILV]-X-[ILV](SEQ ID NO: 35). In another preferred aspect, the isolated polypeptide having cellulolytic enhancing activity further comprises H-X(1,2)-G-P-X(3)-[YW]-[AILMV](SEQ ID NO: 36 or SEQ ID NO: 37) and [EQ]X-Y-X(2)-C-X-[EHQN]-[FILV]-X-[ILV](SEQ ID NO: 38).

In a second aspect, the isolated polypeptides having cellulolytic enhancing activity comprise the following motif:
  [ILMV]-P-x(4,5)-G-x-Y-[ILMV]-x-R-x-[EQ]-x(3)-A-
    [HNQ](SEQ ID NO: 39 or SEQ ID NO: 40),
wherein x is any amino acid, x(4,5) is any amino acid at 4 or 5 contiguous positions, and x(3) is any amino acid at 3 contiguous positions. In the above motif, the accepted IUPAC single letter amino acid abbreviation is employed.

In a third aspect, the isolated polypeptides having cellulolytic enhancing activity comprise an amino acid sequence having a degree of sequence identity to the mature polypeptide of SEQ ID NO: 12, SEQ ID NO: 14, SEQ ID NO: 16, SEQ ID NO: 18, or SEQ ID NO: 20, SEQ ID NO: 22, or SEQ ID NO: 24 of preferably at least 70%, more preferably at least 75%, more preferably at least 80%, even more preferably at least 85%, even more preferably at least 90%, most preferably at least 95%, and even most preferably at least 96%, 97%, 98%, or 99%, which have cellulolytic enhancing activity (hereinafter "homologous polypeptides"). In a preferred aspect, the homologous polypeptides comprise an amino acid sequence that differs by ten amino acids, preferably by five amino acids, more preferably by four amino acids, even more preferably by three amino acids, most preferably by two amino acids, and even most preferably by one amino acid from the mature polypeptide of SEQ ID NO: 12, SEQ ID NO: 14, SEQ ID NO: 16, SEQ ID NO: 18, or SEQ ID NO: 20, SEQ ID NO: 22, or SEQ ID NO: 24.

A polypeptide having cellulolytic enhancing activity preferably comprises the amino acid sequence of SEQ ID NO: 12 or an allelic variant thereof; or a fragment thereof having cellulolytic enhancing activity. In a preferred aspect, the polypeptide comprises the amino acid sequence of SEQ ID NO: 12. In another preferred aspect, the polypeptide comprises the mature polypeptide of SEQ ID NO: 12. In another preferred aspect, the polypeptide comprises amino acids 20 to 326 of SEQ ID NO: 12, or an allelic variant thereof; or a fragment thereof having cellulolytic enhancing activity. In another preferred aspect, the polypeptide comprises amino acids 20 to 326 of SEQ ID NO: 12. In another preferred aspect, the polypeptide consists of the amino acid sequence of SEQ ID NO: 12 or an allelic variant thereof; or a fragment thereof having cellulolytic enhancing activity. In another preferred aspect, the polypeptide consists of the amino acid sequence of SEQ ID NO: 12. In another preferred aspect, the polypeptide consists of the mature polypeptide of SEQ ID NO: 12. In another preferred aspect, the polypeptide consists of amino acids 20 to 326 of SEQ ID NO: 12 or an allelic variant thereof; or a fragment thereof having cellulolytic enhancing activity. In another preferred aspect, the polypeptide consists of amino acids 20 to 326 of SEQ ID NO: 12.

A polypeptide having cellulolytic enhancing activity preferably comprises the amino acid sequence of SEQ ID NO: 14 or an allelic variant thereof; or a fragment thereof having cellulolytic enhancing activity. In a preferred aspect, the polypeptide comprises the amino acid sequence of SEQ ID NO: 14. In another preferred aspect, the polypeptide comprises the mature polypeptide of SEQ ID NO: 14. In another preferred aspect, the polypeptide comprises amino acids 18 to 240 of SEQ ID NO: 14, or an allelic variant thereof; or a fragment thereof having cellulolytic enhancing activity. In another preferred aspect, the polypeptide comprises amino acids 18 to 240 of SEQ ID NO: 14. In another preferred aspect, the polypeptide consists of the amino acid sequence of SEQ ID NO: 14 or an allelic variant thereof; or a fragment thereof having cellulolytic enhancing activity. In another preferred aspect, the polypeptide consists of the amino acid sequence of SEQ ID NO: 14. In another preferred aspect, the polypeptide consists of the mature polypeptide of SEQ ID NO: 14. In another preferred aspect, the polypeptide consists of amino acids 18 to 240 of SEQ ID NO: 14 or an allelic variant thereof; or a fragment thereof having cellulolytic enhancing activity. In another preferred aspect, the polypeptide consists of amino acids 18 to 240 of SEQ ID NO: 14.

A polypeptide having cellulolytic enhancing activity preferably comprises the amino acid sequence of SEQ ID NO: 16 or an allelic variant thereof; or a fragment thereof having cellulolytic enhancing activity. In a preferred aspect, the polypeptide comprises the amino acid sequence of SEQ ID NO: 16. In another preferred aspect, the polypeptide comprises the mature polypeptide of SEQ ID NO: 16. In another preferred aspect, the polypeptide comprises amino acids 20 to 258 of SEQ ID NO: 16, or an allelic variant thereof; or a fragment thereof having cellulolytic enhancing activity. In another preferred aspect, the polypeptide comprises amino acids 20 to 258 of SEQ ID NO: 16. In another preferred aspect, the polypeptide consists of the amino acid sequence of SEQ ID NO: 16 or an allelic variant thereof; or a fragment thereof having cellulolytic enhancing activity. In another preferred aspect, the polypeptide consists of the amino acid sequence of SEQ ID NO: 16. In another preferred aspect, the polypeptide consists of the mature polypeptide of SEQ ID NO: 16. In another preferred aspect, the polypeptide consists of amino acids 20 to 258 of SEQ ID NO: 16 or an allelic variant thereof; or a fragment thereof having cellulolytic enhancing activity. In another preferred aspect, the polypeptide consists of amino acids 20 to 258 of SEQ ID NO: 16.

A polypeptide having cellulolytic enhancing activity preferably comprises the amino acid sequence of SEQ ID NO: 18 or an allelic variant thereof; or a fragment thereof having cellulolytic enhancing activity. In a preferred aspect, the polypeptide comprises the amino acid sequence of SEQ ID NO: 18. In another preferred aspect, the polypeptide comprises the mature polypeptide of SEQ ID NO: 18. In another preferred aspect, the polypeptide comprises amino acids 19 to 226 of SEQ ID NO: 18, or an allelic variant thereof; or a fragment thereof having cellulolytic enhancing activity. In another preferred aspect, the polypeptide comprises amino acids 19 to 226 of SEQ ID NO: 18. In another preferred aspect, the polypeptide consists of the amino acid sequence of SEQ ID NO: 18 or an allelic variant thereof; or a fragment thereof having cellulolytic enhancing activity. In another preferred aspect, the polypeptide consists of the amino acid sequence of SEQ ID NO: 18. In another preferred aspect, the polypeptide consists of the mature polypeptide of SEQ ID NO: 18. In another preferred aspect, the polypeptide consists of amino acids 19 to 226 of SEQ ID NO: 18 or an allelic variant thereof; or a fragment thereof having cellulolytic enhancing activity. In another preferred aspect, the polypeptide consists of amino acids 19 to 226 of SEQ ID NO: 18.

A polypeptide having cellulolytic enhancing activity preferably comprises the amino acid sequence of SEQ ID NO: 20 or an allelic variant thereof; or a fragment thereof having cellulolytic enhancing activity. In a preferred aspect, the polypeptide comprises the amino acid sequence of SEQ ID NO: 20. In another preferred aspect, the polypeptide comprises the mature polypeptide of SEQ ID NO: 20. In another preferred aspect, the polypeptide comprises amino acids 20 to 304 of SEQ ID NO: 20, or an allelic variant thereof; or a fragment thereof having cellulolytic enhancing activity. In another preferred aspect, the polypeptide comprises amino acids 20 to 304 of SEQ ID NO: 20. In another preferred aspect, the polypeptide consists of the amino acid sequence of SEQ ID NO: 20 or an allelic variant thereof; or a fragment thereof having cellulolytic enhancing activity. In another preferred aspect, the polypeptide consists of the amino acid sequence of SEQ ID NO: 20. In another preferred aspect, the polypeptide consists of the mature polypeptide of SEQ ID NO: 20. In another preferred aspect, the polypeptide consists of amino acids 20 to 304 of SEQ ID NO: 20 or an allelic variant thereof; or a fragment thereof having cellulolytic enhancing activity. In another preferred aspect, the polypeptide consists of amino acids 20 to 304 of SEQ ID NO: 20.

A polypeptide having cellulolytic enhancing activity preferably comprises the amino acid sequence of SEQ ID NO: 22 or an allelic variant thereof; or a fragment thereof having cellulolytic enhancing activity. In a preferred aspect, the polypeptide comprises the amino acid sequence of SEQ ID NO: 22. In another preferred aspect, the polypeptide comprises the mature polypeptide of SEQ ID NO: 22. In another preferred aspect, the polypeptide comprises amino acids 23 to 250 of SEQ ID NO: 22, or an allelic variant thereof; or a fragment thereof having cellulolytic enhancing activity. In another preferred aspect, the polypeptide comprises amino acids 23 to 250 of SEQ ID NO: 22. In another preferred aspect, the polypeptide consists of the amino acid sequence of SEQ ID NO: 22 or an allelic variant thereof; or a fragment thereof having cellulolytic enhancing activity. In another preferred aspect, the polypeptide consists of the amino acid sequence of SEQ ID NO: 22. In another preferred aspect, the polypeptide consists of the mature polypeptide of SEQ ID NO: 22. In another preferred aspect, the polypeptide consists of amino acids 23 to 250 of SEQ ID NO: 22 or an allelic variant thereof; or a fragment thereof having cellulolytic enhancing activity. In another preferred aspect, the polypeptide consists of amino acids 23 to 250 of SEQ ID NO: 22.

A polypeptide having cellulolytic enhancing activity preferably comprises the amino acid sequence of SEQ ID NO: 24 or an allelic variant thereof; or a fragment thereof having cellulolytic enhancing activity. In a preferred aspect, the polypeptide comprises the amino acid sequence of SEQ ID NO: 24. In another preferred aspect, the polypeptide comprises the mature polypeptide of SEQ ID NO: 24. In another preferred aspect, the polypeptide comprises amino acids 20 to 249 of SEQ ID NO: 24, or an allelic variant thereof; or a fragment thereof having cellulolytic enhancing activity. In another preferred aspect, the polypeptide comprises amino acids 20 to 249 of SEQ ID NO: 24. In another preferred aspect, the polypeptide consists of the amino acid sequence of SEQ ID NO: 24 or an allelic variant thereof; or a fragment thereof having cellulolytic enhancing activity. In another preferred aspect, the polypeptide consists of the amino acid sequence of SEQ ID NO: 24. In another preferred aspect, the polypeptide consists of the mature polypeptide of SEQ ID NO: 24. In another preferred aspect, the polypeptide consists of amino acids 20 to 249 of SEQ ID NO: 24 or an allelic variant thereof; or a fragment thereof having cellulolytic enhancing activity. In another preferred aspect, the polypeptide consists of amino acids 20 to 249 of SEQ ID NO: 24.

In a fourth aspect, the isolated polypeptides having cellulolytic enhancing activity are encoded by polynucleotides that hybridize under at least very low stringency conditions, preferably at least low stringency conditions, more preferably at least medium stringency conditions, more preferably at least medium-high stringency conditions, even more preferably at least high stringency conditions, and most preferably at least very high stringency conditions with (i) the mature polypeptide coding sequence of SEQ ID NO: 11, SEQ ID NO: 13, SEQ ID NO: 15, SEQ ID NO: 17, SEQ ID NO: 19, SEQ ID NO: 21, or SEQ ID NO: 23, (ii) the cDNA sequence contained in the mature polypeptide coding sequence of SEQ ID NO: 11, SEQ ID NO: 13, SEQ ID NO: 15, or SEQ ID NO: 21, or the genomic DNA sequence comprising the mature polypeptide coding sequence of SEQ ID NO: 17, SEQ ID NO: 19, or SEQ ID NO: 23, or (iii) a full-length complementary strand of (i) or (ii). In a preferred aspect, the mature polypeptide coding sequence is nucleotides 388 to 1332 of SEQ ID NO: 11, nucleotides 98 to 821 of SEQ ID NO: 13, nucleotides 126 to 978 of SEQ ID NO: 15, nucleotides 55 to 678 of SEQ ID NO: 17, nucleotides 58 to 912 of SEQ ID NO: 19, nucleotides 67 to 796 of SEQ ID NO: 21, or nucleotides 77 to 766 of SEQ ID NO: 23.

The nucleotide sequence of SEQ ID NO: 11, SEQ ID NO: 13, SEQ ID NO: 15, SEQ ID NO: 17, SEQ ID NO: 19, SEQ ID NO: 21, or SEQ ID NO: 23, or a subsequence thereof; as well as the amino acid sequence of SEQ ID NO: 12, SEQ ID NO: 14, SEQ ID NO: 16, SEQ ID NO: 18, or SEQ ID NO: 20, SEQ ID NO: 22, or SEQ ID NO: 24, or a fragment thereof, may be used to design a nucleic acid probe to identify and clone DNA encoding polypeptides having cellulolytic enhancing activity from strains of different genera or species, as described supra.

For purposes of the present invention, hybridization indicates that the nucleotide sequence hybridizes to a labeled nucleic acid probe corresponding to the mature polypeptide coding sequence of SEQ ID NO: 11, SEQ ID NO: 13, SEQ ID NO: 15, SEQ ID NO: 17, SEQ ID NO: 19, SEQ ID NO: 21, or SEQ ID NO: 23, the cDNA sequence contained in the mature polypeptide coding sequence of SEQ ID NO: 11, SEQ ID NO: 13, SEQ ID NO: 15, or SEQ ID NO: 21, or the genomic DNA sequence comprising the mature polypeptide coding sequence of SEQ ID NO: 17, SEQ ID NO: 19, or SEQ ID NO: 23, its complementary strand, or a subsequence thereof, under very low to very high stringency conditions, as described supra.

In a preferred aspect, the nucleic acid probe is the mature polypeptide coding sequence of SEQ ID NO: 11. In another preferred aspect, the nucleic acid probe is nucleotides 388 to 1332 of SEQ ID NO: 11. In another preferred aspect, the nucleic acid probe is a polynucleotide sequence that encodes the polypeptide of SEQ ID NO: 12, or a subsequence thereof. In another preferred aspect, the nucleic acid probe is SEQ ID NO: 11. In another preferred aspect, the nucleic acid probe is the polynucleotide sequence contained in plasmid pEJG120 which is contained in *E. coli* NRRL B-30699, wherein the polynucleotide sequence thereof encodes a polypeptide having cellulolytic enhancing activity. In another preferred aspect, the nucleic acid probe is the mature polypeptide coding region contained in plasmid pEJG120 which is contained in *E. coli* NRRL B-30699.

In another preferred aspect, the nucleic acid probe is the mature polypeptide coding sequence of SEQ ID NO: 13. In another preferred aspect, the nucleic acid probe is nucleotides 98 to 821 of SEQ ID NO: 13. In another preferred aspect, the nucleic acid probe is a polynucleotide sequence that encodes the polypeptide of SEQ ID NO: 14, or a subsequence thereof. In another preferred aspect, the nucleic acid probe is SEQ ID NO: 13. In another preferred aspect, the nucleic acid probe is the polynucleotide sequence contained in plasmid pTter61C which is contained in *E. coli* NRRL B-30813, wherein the polynucleotide sequence thereof encodes a polypeptide having cellulolytic enhancing activity. In another preferred aspect, the nucleic acid probe is the mature polypeptide coding region contained in plasmid pTter61C which is contained in *E. coli* NRRL B-30813.

In another preferred aspect, the nucleic acid probe is the mature polypeptide coding sequence of SEQ ID NO: 15. In another preferred aspect, the nucleic acid probe is nucleotides 126 to 978 of SEQ ID NO: 15. In another preferred aspect, the nucleic acid probe is a polynucleotide sequence that encodes the polypeptide of SEQ ID NO: 16, or a subsequence thereof. In another preferred aspect, the nucleic acid probe is SEQ ID NO: 15. In another preferred aspect, the nucleic acid probe is the polynucleotide sequence contained in plasmid pTter61D which is contained in *E. coli* NRRL B-30812, wherein the polynucleotide sequence thereof encodes a polypeptide having cellulolytic enhancing activity. In another preferred aspect, the nucleic acid probe is the mature polypeptide coding region contained in plasmid pTter61D which is contained in *E. coli* NRRL B-30812.

In another preferred aspect, the nucleic acid probe is the mature polypeptide coding sequence of SEQ ID NO: 17. In another preferred aspect, the nucleic acid probe is nucleotides 55 to 678 of SEQ ID NO: 17. In another preferred aspect, the nucleic acid probe is a polynucleotide sequence that encodes the polypeptide of SEQ ID NO: 18, or a subsequence thereof.

In another preferred aspect, the nucleic acid probe is SEQ ID NO: 17. In another preferred aspect, the nucleic acid probe is the polynucleotide sequence contained in plasmid pTter61E which is contained in *E. coli* NRRL B-30814, wherein the polynucleotide sequence thereof encodes a polypeptide having cellulolytic enhancing activity. In another preferred aspect, the nucleic acid probe is the mature polypeptide coding region contained in plasmid pTter61E which is contained in *E. coli* NRRL B-30814.

In another preferred aspect, the nucleic acid probe is the mature polypeptide coding sequence of SEQ ID NO: 19. In another preferred aspect, the nucleic acid probe is nucleotides 58 to 912 of SEQ ID NO: 19 In another preferred aspect, the nucleic acid probe is a polynucleotide sequence that encodes the polypeptide of SEQ ID NO: 20, or a subsequence thereof. In another preferred aspect, the nucleic acid probe is SEQ ID NO: 19. In another preferred aspect, the nucleic acid probe is the polynucleotide sequence contained in plasmid pTter61G which is contained in *E. coli* NRRL B-30811, wherein the polynucleotide sequence thereof encodes a polypeptide having cellulolytic enhancing activity. In another preferred aspect, the nucleic acid probe is the mature polypeptide coding region contained in plasmid pTter61G which is contained in *E. coli* NRRL B-30811.

In another preferred aspect, the nucleic acid probe is the mature polypeptide coding sequence of SEQ ID NO: 21. In another preferred aspect, the nucleic acid probe is nucleotides 67 to 796 of SEQ ID NO: 21. In another preferred aspect, the nucleic acid probe is a polynucleotide sequence that encodes the polypeptide of SEQ ID NO: 22, or a subsequence thereof. In another preferred aspect, the nucleic acid probe is SEQ ID NO: 21. In another preferred aspect, the nucleic acid probe is the polynucleotide sequence contained in plasmid pDZA2-7 which is contained in *E. coli* NRRL B-30704, wherein the polynucleotide sequence thereof encodes a polypeptide having cellulolytic enhancing activity. In another preferred aspect, the nucleic acid probe is the mature polypeptide coding region contained in plasmid pDZA2-7 which is contained in *E. coli* NRRL B-30704.

In another preferred aspect, the nucleic acid probe is the mature polypeptide coding sequence of SEQ ID NO: 23. In another preferred aspect, the nucleic acid probe is nucleotides 77 to 766 of SEQ ID NO: 23. In another preferred aspect, the nucleic acid probe is a polynucleotide sequence that encodes the polypeptide of SEQ ID NO: 24, or a subsequence thereof. In another preferred aspect, the nucleic acid probe is SEQ ID NO: 23. In another preferred aspect, the nucleic acid probe is the polynucleotide sequence contained in plasmid pTr333 which is contained in *E. coli* NRRL B-30878, wherein the polynucleotide sequence thereof encodes a polypeptide having cellulolytic enhancing activity. In another preferred aspect, the nucleic acid probe is the mature polypeptide coding region contained in plasmid pTr333 which is contained in *E. coli* NRRL B-30878.

For long probes of at least 100 nucleotides in length, very low to very high stringency conditions are as defined herein.

For long probes of at least 100 nucleotides in length, the carrier material is finally washed as defined herein.

For short probes of about 15 nucleotides to about 70 nucleotides in length, stringency conditions are as defined herein.

For short probes of about 15 nucleotides to about 70 nucleotides in length, the carrier material is washed as defined herein.

In a fifth aspect, the polypeptides having cellulolytic enhancing activity are encoded by polynucleotides comprising or consisting of nucleotide sequences that have a degree of sequence identity to the mature polypeptide coding sequence of SEQ ID NO: 11, SEQ ID NO: 13, SEQ ID NO: 15, SEQ ID NO: 17, SEQ ID NO: 19, SEQ ID NO: 21, or SEQ ID NO: 23 of preferably at least 70%, more preferably at least 75%, more preferably at least 80%, even more preferably at least 85%, even more preferably at least 90%, most preferably at least 95%, and even most preferably at least 96%, 97%, 98%, or 99%, which encode an active polypeptide.

In a preferred aspect, the mature polypeptide coding sequence is nucleotides 388 to 1332 of SEQ ID NO: 11, nucleotides 98 to 821 of SEQ ID NO: 13, nucleotides 126 to 978 of SEQ ID NO: 15, nucleotides 55 to 678 of SEQ ID NO: 17, nucleotides 58 to 912 of SEQ ID NO: 19, nucleotides 67 to 796 of SEQ ID NO: 21, or nucleotides 77 to 766 of SEQ ID NO: 23. See polynucleotide section herein.

In a sixth aspect, the polypeptides having cellulolytic enhancing activity are artificial variants comprising a substitution, deletion, and/or insertion of one or more (or several) amino acids of the mature polypeptide of SEQ ID NO: 12, SEQ ID NO: 14, SEQ ID NO: 16, SEQ ID NO: 18, or SEQ ID NO: 20, SEQ ID NO: 22, or SEQ ID NO: 24; or a homologous sequence thereof. Methods for preparing such artificial variants are described supra.

The total number of amino acid substitutions, deletions and/or insertions of the mature polypeptide of SEQ ID NO: 12, SEQ ID NO: 14, SEQ ID NO: 16, SEQ ID NO: 18, SEQ ID NO: 20, SEQ ID NO: 22, or SEQ ID NO: 24, is 10, preferably 9, more preferably 8, more preferably 7, more preferably at most 6, more preferably 5, more preferably 4, even more preferably 3, most preferably 2, and even most preferably 1.

Sources for Polypeptides Having Cellulolytic Enhancing Activity

A polypeptide having cellulolytic enhancing activity may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

The polypeptide having cellulolytic enhancing activity may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus*, or *Oceanobacillus* polypeptide having cellulolytic enhancing activity, or a Gram negative bacterial polypeptide such as an *E. coli, Pseudomonas, Salmonella, Campylobacter, Helicobacter, Flavobacterium, Fusobacterium, Ilyobacter, Neisseria*, or *Ureaplasma* polypeptide having cellulolytic enhancing activity.

In a preferred aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* polypeptide having cellulolytic enhancing activity.

In another preferred aspect, the polypeptide is a *Streptococcus equisimilis, Streptococcus pyogenes, Streptococcus uberis*, or *Streptococcus equi* subsp. *Zooepidemicus* polypeptide having cellulolytic enhancing activity.

In another preferred aspect, the polypeptide is a *Streptomyces achromogenes, Streptomyces avermitilis, Streptomyces coelicolor, Streptomyces griseus*, or *Streptomyces lividans* polypeptide having cellulolytic enhancing activity.

The polypeptide having cellulolytic enhancing activity may also be a fungal polypeptide, and more preferably a yeast polypeptide such as a *Candida, Kluyveromyces, Pichia, Saccharomyces, Schizosaccharomyces,* or *Yarrowia* polypeptide having cellulolytic enhancing activity; or more preferably a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* polypeptide having cellulolytic enhancing activity.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide having cellulolytic enhancing activity.

In another preferred aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride,* or *Trichophaea saccata* polypeptide having cellulolytic enhancing activity.

In a more preferred aspect, the polypeptide is a *Thielavia terrestris* polypeptide having cellulolytic enhancing activity. In a most preferred embodiment, the polypeptide is a *Thielavia terrestris* NRRL 8126 polypeptide having cellulolytic enhancing activity, e.g., the mature polypeptide of SEQ ID NO: 12, 14, 16, 18, or 20, or fragments thereof that have cellulolytic enhancing activity.

In another more preferred aspect, the polypeptide is a *Thermoascus aurantiacus* polypeptide, e.g., the mature polypeptide of SEQ ID NO: 22.

In another more preferred aspect, the polypeptide is a *Trichoderma reesei* polypeptide having cellulolytic enhancing activity. In another most preferred aspect, the polypeptide is a *Trichoderma reesei* RutC30 (ATCC 56765) polypeptide, having cellulolytic enhancing activity e.g., the mature polypeptide of SEQ ID NO: 24, or fragments thereof that have cellulolytic enhancing activity.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide sequence encoding a polypeptide has been detected with the probe(s), the polynucleotide can be isolated or cloned by utilizing techniques which are well known to those of ordinary skill in the art (see, e.g., Sambrook et al., 1989, supra).

Polypeptides having cellulolytic enhancing activity also include fused polypeptides or cleavable fusion polypeptides in which another polypeptide is fused at the N-terminus or the C-terminus of the polypeptide or fragment thereof having cellulolytic enhancing activity. Techniques for producing fusion polypeptides are described supra.

For further details on polypeptides having cellulolytic enhancing activity and polynucleotides thereof, see WO 2005/074647, WO 2005/074656, and U.S. Published Application Serial No. 2007/0077630, which are incorporated herein by reference.

Polynucleotides Encoding Polypeptides Having Cellulolytic Enhancing Activity

Polynucleotides comprising or consisting of nucleotide sequences that encode polypeptides having cellulolytic enhancing activity can be isolated and utilized to practice the methods of the present invention, as described herein.

The isolated polynucleotides comprise or consist of nucleotide sequences that have a degree of sequence identity to the mature polypeptide coding sequence of SEQ ID NO: 11, SEQ ID NO: 13, SEQ ID NO: 15, SEQ ID NO: 17, SEQ ID NO: 19, SEQ ID NO: 21, or SEQ ID NO: 23 of preferably at least 70%, more preferably at least 75%, even more preferably at least 80%, even more preferably at least 85%, even more preferably at least 90%, most preferably at least 95%, and even most preferably at least 96%, 97%, 98%, or 99%, which encode a polypeptide having cellulolytic enhancing activity.

In a preferred aspect, the nucleotide sequence comprises or consists of SEQ ID NO: 11. In another more preferred aspect, the nucleotide sequence comprises the sequence contained in plasmid pEJG120 that is contained in *Escherichia coli* NRRL B-30699. In another preferred aspect, the nucleotide sequence comprises or consists of the mature polypeptide coding region of SEQ ID NO: 11. In another more preferred aspect, the nucleotide sequence comprises or consists of the mature polypeptide coding region contained in plasmid pEJG120 that is contained in *Escherichia coli* NRRL B-30699. The present invention also encompasses nucleotide sequences that encode a polypeptide comprising or consisting of the amino acid sequence of SEQ ID NO: 12 or the mature polypeptide thereof, which differ from SEQ ID NO: 11 by virtue of the degeneracy of the genetic code. The present invention also relates to subsequences of SEQ ID NO: 11 that encode fragments of SEQ ID NO: 12 that have cellulolytic enhancing activity.

In another preferred aspect, the nucleotide sequence comprises or consists of SEQ ID NO: 13. In another more preferred aspect, the nucleotide sequence comprises or consists of the sequence contained in plasmid pTter61C that is contained in *Escherichia coli* NRRL B-30813. In another preferred aspect, the nucleotide sequence comprises or consists of the mature polypeptide coding region of SEQ ID NO: 13. In another more preferred aspect, the nucleotide sequence comprises or consists of the mature polypeptide coding region contained in plasmid pTter61C that is contained in *Escherichia coli* NRRL B-30813. The present invention also encompasses nucleotide sequences that encode a polypeptide comprising or consisting of the amino acid sequence of SEQ ID NO: 14 or the mature polypeptide thereof, which differ from SEQ ID NO: 13 by virtue of the degeneracy of the genetic code. The present invention also relates to subsequences of SEQ ID NO: 13 that encode fragments of SEQ ID NO: 14 having cellulolytic enhancing activity.

In another preferred aspect, the nucleotide sequence comprises or consists of SEQ ID NO: 15. In another more preferred aspect, the nucleotide sequence comprises or consists of the sequence contained in plasmid pTter61D that is contained in *Escherichia coli* NRRL B-30812. In another preferred aspect, the nucleotide sequence comprises or consists of the mature polypeptide coding region of SEQ ID NO: 15. In another more preferred aspect, the nucleotide sequence comprises or consists of the mature polypeptide coding region contained in plasmid pTter61D that is contained in *Escherichia coli* NRRL B-30812. The present invention also encompasses nucleotide sequences that encode a polypeptide comprising or consisting of the amino acid sequence of SEQ ID NO: 16 or the mature polypeptide thereof, which differ from SEQ ID NO: 15 by virtue of the degeneracy of the genetic code. The present invention also relates to subsequences of SEQ ID NO: 15 that encode fragments of SEQ ID NO: 16 having cellulolytic enhancing activity.

In another preferred aspect, the nucleotide sequence comprises or consists of SEQ ID NO: 17. In another more preferred aspect, the nucleotide sequence comprises or consists of the sequence contained in plasmid pTter61E that is contained in *Escherichia coli* NRRL B-30814. In another preferred aspect, the nucleotide sequence comprises or consists of the mature polypeptide coding region of SEQ ID NO: 17. In another more preferred aspect, the nucleotide sequence comprises or consists of the mature polypeptide coding region contained in plasmid pTter61E that is contained in *Escherichia coli* NRRL B-30814. The present invention also encompasses nucleotide sequences that encode a polypeptide comprising or consisting of the amino acid sequence of SEQ ID NO: 18 or the mature polypeptide thereof, which differ from SEQ ID NO: 17 by virtue of the degeneracy of the genetic code. The present invention also relates to subsequences of SEQ ID NO: 17 that encode fragments of SEQ ID NO: 18 having cellulolytic enhancing activity.

In another preferred aspect, the nucleotide sequence comprises or consists of SEQ ID NO: 19. In another more preferred aspect, the nucleotide sequence comprises or consists of the sequence contained in plasmid pTter61G that is contained in *Escherichia coli* NRRL B-30811. In another preferred aspect, the nucleotide sequence comprises or consists of the mature polypeptide coding region of SEQ ID NO: 19.

In another more preferred aspect, the nucleotide sequence comprises or consists of the mature polypeptide coding region contained in plasmid pTter61G that is contained in *Escherichia coli* NRRL B-30811. The present invention also encompasses nucleotide sequences that encode a polypeptide comprising or consisting of the amino acid sequence of SEQ ID NO: 20 or the mature polypeptide thereof, which differ from SEQ ID NO: 19 by virtue of the degeneracy of the genetic code. The present invention also relates to subsequences of SEQ ID NO: 19 that encode fragments of SEQ ID NO: 20 that have cellulolytic enhancing activity.

In another preferred aspect, the nucleotide sequence comprises or consists of SEQ ID NO: 21. In another more preferred aspect, the nucleotide sequence comprises or consists of the sequence contained in plasmid pDZA2-7 that is contained in *Escherichia coli* NRRL B-30704. In another preferred aspect, the nucleotide sequence comprises or consists of the mature polypeptide coding region of SEQ ID NO: 21. In another more preferred aspect, the nucleotide sequence comprises or consists of the mature polypeptide coding region contained in plasmid pDZA2-7 that is contained in *Escherichia coli* NRRL B-30704. The present invention also encompasses nucleotide sequences that encode a polypeptide comprising or consisting of the amino acid sequence of SEQ ID NO: 22 or the mature polypeptide thereof, which differ from SEQ ID NO: 21 by virtue of the degeneracy of the genetic code. The present invention also relates to subsequences of SEQ ID NO: 21 that encode fragments of SEQ ID NO: 22 having cellulolytic enhancing activity.

In another preferred aspect, the nucleotide sequence comprises or consists of SEQ ID NO: 23. In another more preferred aspect, the nucleotide sequence comprises or consists of the sequence contained in plasmid pTr3337 which is contained in *Escherichia coli* NRRL B-30878. In another preferred aspect, the nucleotide sequence comprises or consists of the mature polypeptide coding region of SEQ ID NO: 23. In another more preferred aspect, the nucleotide sequence comprises or consists of the mature polypeptide coding region contained in plasmid pTr3337 which is contained in *Escherichia coli* NRRL B-30878. The present invention also encompasses nucleotide sequences that encode a polypeptide comprising or consisting of the amino acid sequence of SEQ ID NO: 24 or the mature polypeptide thereof, which differ from SEQ ID NO: 23 or the mature polypeptide coding sequence thereof by virtue of the degeneracy of the genetic code. The present invention also relates to subsequences of SEQ ID NO: 23 that encode fragments of SEQ ID NO: 24 that have cellulolytic enhancing activity.

The present invention also relates to mutant polynucleotides comprising at least one mutation in the mature polypeptide coding sequence of SEQ ID NO: 11, SEQ ID NO: 13, SEQ ID NO: 15, SEQ ID NO: 17, SEQ ID NO: 19, SEQ ID NO: 21, or SEQ ID NO: 23, in which the mutant nucleotide sequence encodes the mature polypeptide of SEQ ID NO: 12, SEQ ID NO: 14, SEQ ID NO: 16, SEQ ID NO: 18, or SEQ ID NO: 20, SEQ ID NO: 22, or SEQ ID NO: 24. In a preferred aspect, the mature polypeptide is amino acids 20 to 326 of SEQ ID NO: 12, amino acids 18 to 240 of SEQ ID NO: 14, amino acids 20 to 258 of SEQ ID NO: 16, amino acids 19 to 226 of SEQ ID NO: 18, or amino acids 20 to 304 of SEQ ID NO: 20, amino acids 23 to 250 of SEQ ID NO: 22, or amino acids 20 to 249 of SEQ ID NO: 24. In another preferred aspect, the mature polypeptide coding sequence is nucleotides 388 to 1332 of SEQ ID NO: 11, nucleotides 98 to 821 of SEQ ID NO: 13, nucleotides 126 to 978 of SEQ ID NO: 15, nucleotides 55 to 678 of SEQ ID NO: 17, nucleotides 58 to 912 of SEQ ID NO: 19, nucleotides 67 to 796 of SEQ ID NO: 21, or nucleotides 77 to 766 of SEQ ID NO: 23.

As described earlier, the techniques used to isolate or clone a polynucleotide encoding a polypeptide are known in the art and include isolation from genomic DNA, preparation from cDNA, or a combination thereof.

The isolated polynucleotide may also be a polynucleotide encoding a polypeptide having cellulolytic enhancing activity that hybridizes under at least very low stringency conditions, preferably at least low stringency conditions, more preferably at least medium stringency conditions, more preferably at least medium-high stringency conditions, even more preferably at least high stringency conditions, and most preferably at least very high stringency conditions with (i) the mature polypeptide coding sequence of SEQ ID NO: 11, SEQ ID NO: 13, SEQ ID NO: 15, SEQ ID NO: 17, SEQ ID NO: 19, SEQ ID NO: 21, or SEQ ID NO: 23, (ii) the cDNA sequence contained in the mature polypeptide coding sequence of SEQ ID NO: 11, SEQ ID NO: 13, SEQ ID NO: 15, or SEQ ID NO: 21, or the genomic DNA sequence comprising the mature polypeptide coding sequence of SEQ ID NO: 17, SEQ ID NO: 19, or SEQ ID NO: 23, or (iii) a full-length complementary strand of (i) or (ii); or allelic variants and subsequences thereof, as defined herein. In a preferred aspect, the mature polypeptide coding sequence is nucleotides 388 to 1332 of SEQ ID NO: 11, nucleotides 98 to 821 of SEQ ID NO: 13, nucleotides 126 to 978 of SEQ ID NO: 15, nucleotides 55 to 678 of SEQ ID NO: 17, nucleotides 58 to 912 of SEQ ID NO: 19, nucleotides 67 to 796 of SEQ ID NO: 21, or nucleotides 77 to 766 of SEQ ID NO: 23.

Nucleic Acid Constructs

An isolated polynucleotide encoding a polypeptide having cellulolytic enhancing activity, a CEL7 polypeptide having endoglucanase activity, a CEL12 polypeptide having endoglucanase activity, a CEL45 polypeptide having endoglucanase activity, a CEL7 polypeptide having cellobiohydrolase activity with a cellulose binding domain, a CEL7 polypeptide having cellobiohydrolase activity without a cellulose binding domain, and/or a polypeptide having beta-glucosidase activity may be manipulated in a variety of ways to provide for expression of the polypeptides by constructing a nucleic acid construct(s) comprising one or more (several) of the isolated polynucleotides operably linked to one or more (several) control sequences which direct the expression of the coding sequence in a suitable host cell under conditions compatible with the control sequences. Manipulation of the polynucleotides' sequences prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence that is recognized by a host cell for expression of a polynucleotide encoding such a polypeptide. The promoter sequence contains transcriptional control sequences which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator that is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence that is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice, i.e., secreted into a culture medium, may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

In a preferred aspect, the signal peptide comprises or consists of amino acids 1 to 20 of SEQ ID NO: 2. In another preferred aspect, the signal peptide coding region comprises or consists of nucleotides 1 to 60 of SEQ ID NO: 1.

In another preferred aspect, the signal peptide comprises or consists of amino acids 1 to 15 of SEQ ID NO: 4. In another preferred aspect, the signal peptide coding region comprises or consists of nucleotides 1 to 45 of SEQ ID NO: 3.

In another preferred aspect, the signal peptide comprises or consists of amino acids 1 to 18 of SEQ ID NO: 6. In another preferred aspect, the signal peptide coding region comprises or consists of nucleotides 1 to 54 of SEQ ID NO: 5.

In another preferred aspect, the signal peptide comprises or consists of amino acids 1 to 17 of SEQ ID NO: 8. In another preferred aspect, the signal peptide coding region comprises or consists of nucleotides 1 to 51 of SEQ ID NO: 7.

In another preferred aspect, the signal peptide comprises or consists of amino acids 1 to 20 of SEQ ID NO: 10. In another preferred aspect, the signal peptide coding region comprises or consists of nucleotides 1 to 60 of SEQ ID NO: 9.

In another preferred aspect, the signal peptide comprises or consists of amino acids 1 to 19 of SEQ ID NO: 12. In another preferred aspect, the signal peptide coding region comprises or consists of nucleotides 330 to 387 of SEQ ID NO: 11.

In another preferred aspect, the signal peptide comprises or consists of amino acids 1 to 17 of SEQ ID NO: 14. In another preferred aspect, the signal peptide coding region comprises or consists of nucleotides 47 to 97 of SEQ ID NO: 13.

In another preferred aspect, the signal peptide comprises or consists of amino acids coding region is amino acids 1 to 19 of SEQ ID NO: 16. In another preferred aspect, the signal peptide coding region comprises or consists of nucleotides 69 to 125 of SEQ ID NO: 15.

In another preferred aspect, the signal peptide comprises or consists of amino acids 1 to 18 of SEQ ID NO: 18. In another preferred aspect, the signal peptide coding region comprises or consists of nucleotides 1 to 54 of SEQ ID NO: 17.

In another preferred aspect, the signal peptide comprises or consists of amino acids 1 to 19 of SEQ ID NO: 20. In another preferred aspect, the signal peptide coding region comprises or consists of nucleotides 1 to 57 of SEQ ID NO: 19.

In another preferred aspect, the signal peptide comprises or consists of amino acids 1 to 22 of SEQ ID NO: 22. In another preferred aspect, the signal peptide coding region comprises or consists of nucleotides 1 to 66 of SEQ ID NO: 21.

In another preferred aspect, the signal peptide comprises or consists of amino acids 1 to 19 of SEQ ID NO: 24. In another preferred aspect, the signal peptide coding region comprises or consists of nucleotides 20 to 76 of SEQ ID NO: 23.

In another preferred aspect, the signal peptide comprises or consists of amino acids 1 to 19 of SEQ ID NO: 26. In another preferred aspect, the signal peptide coding region comprises or consists of nucleotides 31 to 86 of SEQ ID NO: 25.

In another preferred aspect, the signal peptide comprises or consists of amino acids 1 to 19 of SEQ ID NO: 26. In another preferred aspect, the signal peptide coding region comprises or consists of nucleotides 1 to 57 of SEQ ID NO: 27.

In another preferred aspect, the signal peptide comprises or consists of amino acids 1 to 19 of SEQ ID NO: 28. In another preferred aspect, the signal peptide coding region comprises or consists of nucleotides 6 to 62 of SEQ ID NO: 29.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene that is amplified in the presence of methotrexate, and the metallothionein genes which are amplified with heavy metals. In these cases, the nucleotide sequence encoding the polypeptide would be operably linked with the regulatory sequence.

Expression Vectors

The various nucleic acids and control sequences described herein may be joined together to produce a recombinant expression vector comprising a polynucleotide encoding a polypeptide having cellulolytic enhancing activity, a CEL7 polypeptide having endoglucanase activity, a CEL12 polypeptide having endoglucanase activity, a CEL45 polypeptide having endoglucanase activity, a CEL7 polypeptide having cellobiohydrolase activity with a cellulose binding domain, a CEL7 polypeptide having cellobiohydrolase activity without a cellulose binding domain, and/or a polypeptide having beta-glucosidase activity, a promoter, and transcriptional and translational stop signals. The expression vectors may include one or more (several) convenient restriction sites to allow for insertion or substitution of the nucleotide sequence encoding the polypeptide at such sites. Alternatively, a polynucleotide encoding such a polypeptide may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors preferably contain one or more (several) selectable markers which permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers which confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide encoding such a polypeptide may be inserted into the host cell to increase production of the polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors are well known to one skilled in the art (see, e.g., Sambrook et al., 1989, supra).

Host Cells

Recombinant host cells, comprising a polynucleotide(s) encoding a polypeptide having cellulolytic enhancing activity, a CEL7 polypeptide having endoglucanase activity, a CEL12 polypeptide having endoglucanase activity, a CEL45 polypeptide having endoglucanase activity, a CEL7 polypeptide having cellobiohydrolase activity with a cellulose binding domain, a CEL7 polypeptide having cellobiohydrolase activity without a cellulose binding domain, and/or a polypeptide having beta-glucosidase activity can be advantageously used in the recombinant production of the polypeptide. A vector comprising such a polynucleotide is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

The bacterial host cell may be any Gram positive bacterium or a Gram negative bacterium. Gram positive bacteria include, but not limited to, *Bacillus, Streptococcus, Streptomyces, Staphylococcus, Enterococcus, Lactobacillus, Lactococcus, Clostridium, Geobacillus*, and *Oceanobacillus*. Gram negative bacteria include, but not limited to, *E. coli, Pseudomonas, Salmonella, Campylobacter, Helicobacter, Flavobacterium, Fusobacterium, Ilyobacter, Neisseria*, and *Ureaplasma*.

The bacterial host cell may be any Bacillus cell. *Bacillus* cells useful in the practice of the present invention include, but are not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

In a preferred aspect, the bacterial host cell is a *Bacillus amyloliquefaciens, Bacillus lentus, Bacillus licheniformis, Bacillus stearothermophilus* or *Bacillus subtilis* cell. In a more preferred aspect, the bacterial host cell is a *Bacillus amyloliquefaciens* cell. In another more preferred aspect, the bacterial host cell is a *Bacillus clausii* cell. In another more preferred aspect, the bacterial host cell is a *Bacillus licheniformis* cell. In another more preferred aspect, the bacterial host cell is a *Bacillus subtilis* cell.

The bacterial host cell may also be any *Streptococcus* cell. *Streptococcus* cells useful in the practice of the present invention include, but are not limited to, *Streptococcus equisimilis, Streptococcus pyogenes, Streptococcus uberis*, and *Streptococcus equi* subsp. *Zooepidemicus*.

In a preferred aspect, the bacterial host cell is a *Streptococcus equisimilis* cell. In another preferred aspect, the bacterial host cell is a *Streptococcus pyogenes* cell. In another preferred aspect, the bacterial host cell is a *Streptococcus uberis* cell. In another preferred aspect, the bacterial host cell is a *Streptococcus equi* subsp. *Zooepidemicus* cell.

The bacterial host cell may also be any *Streptomyces* cell. *Streptomyces* cells useful in the practice of the present invention include, but are not limited to, *Streptomyces achromogenes, Streptomyces avermitilis, Streptomyces coelicolor, Streptomyces griseus*, and *Streptomyces lividans*.

In a preferred aspect, the bacterial host cell is a *Streptomyces achromogenes* cell. In another preferred aspect, the bacterial host cell is a *Streptomyces avermitilis* cell. In another preferred aspect, the bacterial host cell is a *Streptomyces coelicolor* cell. In another preferred aspect, the bacterial host cell is a *Streptomyces griseus* cell. In another preferred aspect, the bacterial host cell is a *Streptomyces lividans* cell.

The introduction of DNA into a *Bacillus* cell may, for instance, be effected by protoplast transformation (see, e.g., Chang and Cohen, 1979, *Molecular General Genetics* 168: 111-115), by using competent cells (see, e.g., Young and Spizizen, 1961, *Journal of Bacteriology* 81: 823-829, or Dubnau and Davidoff-Abelson, 1971, *Journal of Molecular Biology* 56: 209-221), by electroporation (see, e.g., Shigekawa and Dower, 1988, *Biotechniques* 6: 742-751), or by conjugation (see, e.g., Koehler and Thorne, 1987, *Journal of Bacteriology* 169: 5271-5278). The introduction of DNA into an *E coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (Praha) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98:6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios.* 68: 189-2070, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980).

In an even more preferred aspect, the yeast host cell is a *Candida, Hansenula, Kluyveromyces, Pichia, Saccharomyces, Schizosaccharomyces,* or *Yarrowia* cell.

In a most preferred aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Coprinus cinereus, Coriolus hirsutus, Humicola insolens, Humicola lanuginosa, Mucor miehei, Myceliophthora thermophile, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The cellulolytic enzyme composition of the present invention may be produced by fermentation of a microbial strain (wild-type or recombinant host cell) or by fermentation of several individual microbial strains (wild-type and/or recombinant host cells).

Methods for producing a polypeptide having cellulolytic enhancing activity, a CEL7 polypeptide having endoglucanase activity, a CEL12 polypeptide having endoglucanase activity, a CEL45 polypeptide having endoglucanase activity, a CEL7 polypeptide having cellobiohydrolase activity with a cellulose binding domain, a CEL7 polypeptide having cellobiohydrolase activity without a cellulose binding domain, and/or a polypeptide having beta-glucosidase activity, comprise (a) cultivating a cell, which in its wild-type form is capable of producing the polypeptide, under conditions conducive for production of the polypeptide; and (b) recovering the polypeptide.

Alternatively, methods for producing a polypeptide having cellulolytic enhancing activity, a CEL7 polypeptide having endoglucanase activity, a CEL12 polypeptide having endoglucanase activity, a CEL45 polypeptide having endoglucanase activity, a CEL7 polypeptide having cellobiohydrolase activity with a cellulose binding domain, and/or a CEL7 polypeptide having cellobiohydrolase activity without a cellulose binding domain, comprise (a) cultivating a recombinant host cell under conditions conducive for production of the polypeptide; and (b) recovering the polypeptide.

Further, methods for producing a polypeptide having cellulolytic enhancing activity, a CEL7 polypeptide having endoglucanase activity, a CEL12 polypeptide having endoglucanase activity, a CEL45 polypeptide having endoglucanase activity, a CEL7 polypeptide having cellobiohydrolase activity with a cellulose binding domain, a CEL7 polypeptide having cellobiohydrolase activity without a cellulose binding domain, and/or a polypeptide having beta-glucosidase activity, comprise (a) cultivating a host cell under conditions conducive for production of the polypeptide, wherein the host cell comprises a mutant nucleotide sequence comprising at least one mutation in the mature polypeptide coding region of SEQ ID NO: 1, SEQ ID NO: 3, SEQ ID NO: 5, SEQ ID NO: 5, SEQ ID NO: 7, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, or SEQ ID NO: 29, wherein the mutant nucleotide sequence encodes a polypeptide which consists of the mature polypeptide of SEQ ID NO: 2, SEQ ID NO: 4, SEQ ID NO: 6, SEQ ID NO: 8, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, or SEQ ID NO: 30 and (b) recovering the polypeptide.

In the production methods, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted into the medium, it can be recovered from cell lysates.

The polypeptides having cellulolytic enhancing activity, endoglucanase activity, cellobiohydrolase activity, or beta-glucosidase activity are detected using the methods described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification,* J.-C. Janson and Lars Ryden, editors, VCH Publishers, New York, 1989) to obtain substantially pure polypeptides.

Processing of Cellulose-Containing Material

The compositions and methods of the present invention can be used to hydrolyze (saccharify) a cellulose-containing material, e.g., lignocellulose, to fermentable sugars and convert the fermentable sugars to many useful substances, e.g., chemicals and fuels. The production of a desired fermentation product from cellulose-containing material typically involves pretreatment, enzymatic hydrolysis (saccharification), and fermentation.

The processing of cellulose-containing material according to the present invention can be accomplished using processes known in the art. Moreover, the methods of the present invention can be implemented using any biomass processing apparatus configured to operate in accordance with the invention.

Hydrolysis (saccharification) and fermentation, separate or simultaneous, include, but are not limited to, separate hydrolysis and fermentation (SHF), simultaneous saccharification and fermentation (SSF), simultaneous saccharification and cofermentation (SSCF), hybrid hydrolysis and fermentation (HHF), SHCF (separate hydrolysis and co-fermentation), HHCF (hybrid hydrolysis and fermentation), and direct microbial conversion (DMC). It is understood herein that any method known in the art comprising pretreatment, enzymatic hydrolysis (saccharification), fermentation, or a combination thereof, can be used in the practicing the methods of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flávio Faria de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include, for example, fluidized bed, upflow blanket, immobilized, and extruder type reactors for hydrolysis and/or fermentation.

Pretreatment. In practicing the methods of the present invention, any pretreatment process known in the art can be used to disrupt the plant cell wall components of the cellulose-containing material. The cellulose-containing material can also be subjected to pre-soaking, wetting, or conditioning prior to pretreatment using methods known in the art. Conventional pretreatments include, but are not limited to, steam pretreatment (with or without explosion), dilute acid pretreatment, hot water pretreatment, lime pretreatment, wet oxidation, wet explosion, ammonia fiber explosion, organosolv pretreatment, and biological pretreatment. Additional pretreatments include ultrasound, electroporation, microwave, supercritical $CO_2$, supercritical $H_2O$, and ammonia percolation.

The cellulose-containing material can be pretreated before hydrolysis and/or fermentation. Pretreatment is preferably performed prior to the hydrolysis. Alternatively, the pretreatment can be carried out simultaneously with hydrolysis, such as simultaneously with treatment of the cellulose-containing material with one or more cellulolytic enzymes, or other enzyme activities, to release fermentable sugars, such as glucose and/or maltose. In most cases the pretreatment step itself results in some conversion of biomass to fermentable sugars (even in absence of enzymes).

Steam Pretreatment. In steam pretreatment, the cellulose-containing material is heated to disrupt the plant cell wall components, including lignin, hemicellulose, and cellulose to make the cellulose and other fractions, e.g., hemicellulase, accessible to enzymes. The cellulose material is passed to or through a reaction vessel where steam is injected to increase the temperature to the required temperature and pressure and is retained therein for the desired reaction time. Steam pretreatment is preferably done at 140-230° C., more preferably at 160-200° C., and most preferably at 170-190° C., where the optimal temperature range depends on addition of a chemical catalyst. Residence time for the steam pretreatment is preferably 1-15 minutes, more preferably 3-12 minutes, and most preferably 4-10 minutes, where the optimal residence time depends on the temperature range and addition of a chemical catalyst. Steam pretreatment allows for relatively high solids loadings, so that the cellulose-containing material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 20020164730).

A catalyst such as $H_2SO_4$ or $SO_2$ (typically 0.3 to 3% w/w) is often added prior to steam pretreatment, which decreases the time and temperature, increases recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762).

Chemical Pretreatment: The term "chemical treatment" refers to any chemical pretreatment that promotes the separation and/or release of cellulose, hemicellulose, and/or lignin. Examples of suitable chemical pretreatment processes include, for example, dilute acid pretreatment, lime pretreatment, wet oxidation, ammonia fiber/freeze explosion (AFEX), ammonia percolation (APR), and organosolv pretreatments.

In dilute acid pretreatment, the cellulose-containing material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, lime pretreatment, wet oxidation, ammonia percolation (APR), and ammonia fiber/freeze explosion (AFEX).

Lime pretreatment is performed with calcium carbonate, sodium hydroxide, or ammonia at low temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/11899, WO 2006/11900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed at preferably 1-40% dry matter, more preferably 2-30% dry matter, and most preferably 5-20% dry matter, and often the initial pH is increased by the addition of alkali such as sodium carbonate.

A modification of the wet oxidation pretreatment method, known as wet explosion (combination of wet oxidation and steam explosion), can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating cellulose-containing material with liquid or gaseous ammonia at moderate temperatures such as 90-100° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121:1133-1141; Teymouri et al., 2005, *Bioresource Technol.* 96: 2014-2018).

Organosolv pretreatment delignifies cellulose-containing material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121:219-230). Sulphuric acid is usually added as a catalyst. In organosolv pretreatment, the majority of the hemicellulose is removed.

Other examples of suitable pretreatment methods are described by Schell et al., 2003, *Appl. Biochem. and Biotechnol.* Vol. 105-108, p. 69-85, and Mosier et al., 2005, *Bioresource Technology* 96: 673-686, and U.S. Published Application 2002/0164730.

In one aspect, the chemical pretreatment is preferably carried out as an acid treatment, and more preferably as a continuous dilute and/or mild acid treatment. The acid is typically sulfuric acid, but other acids can also be used, such as acetic acid, citric acid, nitric acid, phosphoric acid, tartaric acid, succinic acid, hydrogen chloride or mixtures thereof. Mild acid treatment is conducted in the pH range of preferably 1-5, more preferably 1-4, and most preferably 1-3. In one aspect, the acid concentration is in the range from preferably 0.01 to 20 wt % acid, more preferably 0.05 to 10 wt % acid, even more preferably 0.1 to 5 wt % acid, and most preferably 0.2 to 2.0 wt % acid. The acid is contacted with the cellulose-containing material and held at a temperature, for example, in the range of 160-220° C., preferably 165-195° C., for periods ranging from seconds to minutes to, e.g., 1 second to 60 minutes.

In another aspect, pretreatment is carried out as an ammonia fiber explosion step (AFEX pretreatment step).

In another aspect, pretreatment takes place in an aqueous slurry. In preferred aspects, the cellulose-containing material is present during pretreatment in amounts preferably between 10-80 wt %, more preferably between 20-70 wt %, and most preferably between 30-60 wt %, such as around 50 wt %. The pretreated cellulose-containing material can be unwashed or washed using any method known in the art, e.g., washed with water.

Mechanical Pretreatment: The term "mechanical pretreatment" refers to various types of grinding or milling (e.g., dry milling, wet milling, or vibratory ball milling).

Physical Pretreatment: The term "physical pretreatment" refers to any pretreatment that promotes the separation and/or release of cellulose, hemicellulose, and/or lignin from cellulose-containing material. For example, physical pretreatment can involve irradiation (e.g., microwave irradiation), steaming/steam explosion, hydrothermolysis, and combinations thereof.

Physical pretreatment can involve high pressure and/or high temperature (steam explosion). In one aspect, high pressure means pressure in the range of preferably about 300 to about 600 psi, more preferably about 350 to about 550 psi, and most preferably about 400 to about 500 psi, such as around 450 psi. In another aspect, high temperature means temperatures in the range of about 100 to about 300° C., preferably about 140 to about 235° C. In a preferred aspect, mechanical pretreatment is performed in a batch-process, steam gun hydrolyzer system that uses high pressure and high temperature as defined above, e.g., a Sunds Hydrolyzer available from Sunds Defibrator AB, Sweden.

Combined Physical and Chemical Pretreatment: The cellulose-containing material can be pretreated both physically and chemically. For instance, the pretreatment step can involve dilute or mild acid treatment and high temperature and/or pressure treatment. The physical and chemical pretreatments can be carried out sequentially or simultaneously, as desired. A mechanical pretreatment can also be included.

Accordingly, in a preferred aspect, the cellulose-containing material is subjected to mechanical, chemical, or physical pretreatment, or any combination thereof, to promote the separation and/or release of cellulose, hemicellulose and/or lignin.

Biological Pretreatment: The term "biological pretreatment" refers to any biological pretreatment that promotes the separation and/or release of cellulose, hemicellulose, and/or lignin from the cellulose-containing material. Biological pretreatment techniques can involve applying lignin-solubilizing microorganisms (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of lignocellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification. In the hydrolysis step, also known as saccharification, the pretreated cellulose-containing material is hydrolyzed to break down cellulose and alternatively also hemicellulose to fermentable sugars, such as glucose, xylose, xylulose, arabinose, maltose, mannose, galactose, and/or soluble oligosaccharides. The hydrolysis is performed enzymatically using a cellulolytic enzyme composition of the present invention comprising an effective amount of a polypeptide having cellulolytic enhancing activity. The enzymes components of the composition can also be added sequentially.

Enzymatic hydrolysis is preferably carried out in a suitable aqueous environment under conditions that can be readily determined by one skilled in the art. In a preferred aspect, hydrolysis is performed under conditions suitable for the activity of the enzyme(s), i.e., optimal for the enzyme(s). The hydrolysis can be carried out as a fed batch or continuous process where the pretreated cellulose-containing material (substrate) is fed gradually to, for example, an enzyme containing hydrolysis solution.

The saccharification is generally performed in stirred-tank reactors or fermentors under controlled pH, temperature, and mixing conditions. Suitable process time, temperature, and pH conditions can readily be determined by one skilled in the art. For example, the saccharification can last up to 200 hours, but is typically performed for preferably about 12 to about 96 hours, more preferably about 16 to about 72 hours, and most preferably about 24 to about 48 hours. The temperature is in the range of preferably about 25° C. to about 70° C., more preferably about 30° C. to about 65° C., and more preferably about 40° C. to 60° C., in particular about 50° C. The pH is in the range of preferably about 3 to about 8, more preferably about 3.5 to about 7, and most preferably about 4 to about 6, in particular about pH 5. The dry solids content is in the range of preferably about 5 to about 50 wt %, more preferably about 10 to about 40 wt %, and most preferably about 20 to about 30 wt %.

The optimum amounts of the enzymes and polypeptides having cellulolytic enhancing activity depend on several factors including, but not limited to, the mixture of component cellulolytic proteins, the cellulosic substrate, the concentration of cellulosic substrate, the pretreatment(s) of the cellulosic substrate, temperature, time, pH, and inclusion of fermenting organism (e.g., yeast for Simultaneous Saccharification and Fermentation).

In a preferred aspect, an effective amount of cellulolytic protein(s) to cellulose-containing material is about 0.5 to about 50 mg, preferably at about 0.5 to about 40 mg, more preferably at about 0.5 to about 25 mg, more preferably at about 0.75 to about 20 mg, more preferably at about 0.75 to about 15 mg, even more preferably at about 0.5 to about 10 mg, and most preferably at about 2.5 to about 10 mg per g of cellulose-containing material.

In another preferred aspect, an effective amount of a polypeptide having cellulolytic enhancing activity to cellulose-containing material is about 0.5 to about 50 mg, preferably at about 0.5 to about 40 mg, more preferably at about 0.5 to about 25 mg, more preferably at about 0.75 to about 20 mg, more preferably at about 0.75 to about 15 mg, even more preferably at about 0.5 to about 10 mg, and most preferably at about 2.5 to about 10 mg per g of cellulose-containing material.

In another preferred aspect, an effective amount of polypeptide(s) having cellulolytic enhancing activity to cellulose-containing material is about 0.01 to about 50.0 mg, preferably about 0.01 to about 40 mg, more preferably about 0.01 to about 30 mg, more preferably about 0.01 to about 20 mg, more preferably about 0.01 to about 10 mg, more preferably about 0.01 to about 5 mg, more preferably at about 0.025 to about 1.5 mg, more preferably at about 0.05 to about 1.25 mg, more preferably at about 0.075 to about 1.25 mg, more preferably at about 0.1 to about 1.25 mg, even more preferably at about 0.15 to about 1.25 mg, and most preferably at about 0.25 to about 1.0 mg per g of cellulose-containing material.

In another preferred aspect, an effective amount of polypeptide(s) having cellulolytic enhancing activity to cellulolytic protein(s) is about 0.005 to about 1.0 g, preferably at about 0.01 to about 1.0 g, more preferably at about 0.15 to about 0.75 g, more preferably at about 0.15 to about 0.5 g, more preferably at about 0.1 to about 0.5 g, even more preferably at about 0.1 to about 0.5 g, and most preferably at about 0.05 to about 0.2 g per g of cellulolytic protein(s).

Fermentation. The fermentable sugars obtained from the pretreated and hydrolyzed cellulose-containing material can be fermented by one or more fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the biofuel industry, consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulose-containing material as a result of the pretreatment and enzymatic hydrolysis steps, are fermented to a product, e.g., ethanol, by a fermenting organism, such as yeast. Hydrolysis (saccharification) and fermentation can be separate or simultaneous. Such methods include, but are not limited to, separate hydrolysis and fermentation (SHF), simultaneous saccharification and fermentation (SSF), simultaneous saccharification and cofermentation (SSCF), hybrid hydrolysis and fermentation (HHF), SHCF (separate hydrolysis and co-fermentation), HHCF (hybrid hydrolysis and fermentation), and direct microbial conversion (DMC).

Any suitable hydrolyzed cellulose-containing material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is (are) added, such as, a medium resulting from a saccharification process, as well as a medium, for example, used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be $C_6$ and/or $C_5$ fermenting organisms, or a combination thereof. Both $C_6$ and $C_5$ fermenting organisms are well known in the art. Suitable fermenting microorganisms are able to ferment, i.e., convert, sugars, such as glucose, xylose, xylulose, arabinose, maltose, mannose, galactose, or oligosaccharides, directly or indirectly into the desired fermentation product.

Examples of bacterial and fungal fermenting organisms producing ethanol are described by Lin et al., 2006, *Appl. Microbiol. Biotechnol.* 69: 627-642.

Examples of fermenting microorganisms that can ferment C6 sugars include bacterial and fungal organisms, such as yeast. Preferred yeast includes strains of *Saccharomyces* spp., preferably *Saccharomyces cerevisiae*.

Examples of fermenting organisms that can ferment C5 sugars include bacterial and fungal organisms, such as yeast. Preferred C5 fermenting yeast include strains of *Pichia*, preferably *Pichia stipitis*, such as *Pichia stipitis* CBS 5773; strains of *Candida*, preferably *Candida boidinii, Candida brassicae, Candida sheatae, Candida diddensii, Candida pseudotropicalis*, or *Candida utilis*.

Other fermenting organisms include strains of *Zymomonas*, such as *Zymomonas mobilis; Hansenula*, such as *Hansenula anomala; Klyveromyces*, such as *K. fragilis; Schizosaccharomyces*, such as *S. pombe*; and *E. coli*, especially *E. coli* strains that have been genetically modified to improve the yield of ethanol.

In a preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum*. In another preferred aspect, the yeast is a *Kluyveromyces*. In another more preferred aspect, the yeast is *Kluyveromyces marxianus*. In another more preferred aspect, the yeast is *Kluyveromyces fragilis*. In another preferred aspect, the yeast is a *Candida*. In another more preferred aspect, the yeast is *Candida boidinii*. In another more preferred aspect, the yeast is *Candida brassicae*. In another more preferred aspect, the yeast is *Candida diddensii*. In another more preferred aspect, the yeast is *Candida pseudotropicalis*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Bretannomyces*. In another more preferred aspect, the yeast is *Bretannomyces clausenii* (Philippidis, G. P., 1996, Cellulose bioconversion technology, in *Handbook on Bioethanol: Production and Utilization*, Wyman, C. E., ed., Taylor & Francis, Washington, D.C., 179-212).

Bacteria that can efficiently ferment hexose and pentose to ethanol include, for example, *Zymomonas mobilis* and *Clostridium thermocellum* (Philippidis, 1996, supra).

In a preferred aspect, the bacterium is a *Zymomonas*. In a more preferred aspect, the bacterium is *Zymomonas mobilis*. In another preferred aspect, the bacterium is a *Clostridium*. In another more preferred aspect, the bacterium is *Clostridium thermocellum*.

Commercially available yeast suitable for ethanol production includes, e.g., ETHANOL RED™ yeast (available from Fermentis/Lesaffre, USA), FALI™ (available from Fleischmann's Yeast, USA), SUPERSTART™ and THERMOSACC™ fresh yeast (available from Ethanol Technology, Wis., USA), BIOFERM™ AFT and XR (available from NABC—North American Bioproducts Corporation, Ga., USA), GERT STRAND™ (available from Gert Strand AB, Sweden), and FERMIOL™ (available from DSM Specialties).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (cofermentation) (Chen and Ho, 1993, Cloning and improving the expression of *Pichia stipitis* xylose reductase gene in *Saccharomyces cerevisiae, Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae*, *Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli, Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis, Science* 267: 240-243; Deanda et al., 1996, Development of an arabinose-fermenting *Zymomonas mobilis* strain by metabolic pathway engineering, *Appl. Environ. Microbiol.* 62: 4465-4470).

In a preferred aspect, the genetically modified fermenting microorganism is *Saccharomyces cerevisiae*. In another preferred aspect, the genetically modified fermenting microorganism is *Zymomonas mobilis*. In another preferred aspect, the genetically modified fermenting microorganism is

*Escherichia coli*. In another preferred aspect, the genetically modified fermenting microorganism is *Klebsiella oxytoca*.

The fermenting microorganism(s) is typically added to the degraded cellulose or hydrolysate and the fermentation is performed for about 8 to about 96 hours, such as about 24 to about 60 hours. The temperature is typically between about 26° C. to about 60° C., in particular about 32° C. or 50° C., and at about pH 3 to about pH 8, such as around pH 4-5, 6, or 7.

In a preferred aspect, the fermenting microorganism(s) is applied to the degraded cellulose or hydrolysate and the fermentation is performed for about 12 to about 96 hours, such as typically 24-60 hours. In a preferred aspect, the temperature is preferably between about 20° C. to about 60° C., more preferably about 25° C. to about 50° C., and most preferably about 32° C. to about 50° C., in particular about 32° C. or 50° C., and the pH is generally from about pH 3 to about pH 7, preferably around pH 4-7. However, some, e.g., bacterial fermenting organisms have higher fermentation temperature optima. The fermenting microorganism(s) is preferably applied in amounts of approximately $10^5$ to $10^{12}$, preferably from approximately $10^7$ to $10^{10}$, especially approximately $2 \times 10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation the fermented slurry is distilled to extract the ethanol. The ethanol obtained according to the methods of the invention can be used as, e.g., fuel ethanol, drinking ethanol, i.e., potable neutral spirits, or industrial ethanol.

A fermentation stimulator can be used in combination with any of the enzymatic processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation products: A fermentation product can be any substance derived from the fermentation. The fermentation product can be, without limitation, an alcohol (e.g., arabinitol, butanol, ethanol, glycerol, methanol, 1,3-propanediol, sorbitol, and xylitol); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, and xylonic acid); a ketone (e.g., acetone); an aldehyde (e.g., formaldehyde); an amino acid (e.g., aspartic acid, glutamic acid, glycine, lysine, serine, and threonine); and a gas (e.g., methane, hydrogen ($H_2$), carbon dioxide ($CO_2$), and carbon monoxide (CO)). The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is arabinitol. In another more preferred aspect, the alcohol is butanol. In another more preferred aspect, the alcohol is ethanol. In another more preferred aspect, the alcohol is glycerol. In another more preferred aspect, the alcohol is methanol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an aldehyde. In another more preferred aspect, the aldehyde is formaldehyde.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

Recovery. The fermentation product(s) can be optionally recovered from the fermentation medium using any method known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), distillation, or extraction. For example, ethanol is separated from the fermented cellulose-containing material and purified by conventional methods of distillation. Ethanol with a purity of up to about 96 vol. % can be obtained, which can be used as, for example, fuel ethanol, drinking ethanol, i.e., potable neutral spirits, or industrial ethanol.

The present invention is further described by the following examples which should not be construed as limiting the scope of the invention.

EXAMPLES

Materials

Chemicals used as buffers and substrates were commercial products of at least reagent grade.

Media

NNCYP medium was composed per liter of 5.0 g of $NH_4NO_3$, 0.5 g of $MgSO_4.7H_2O$, 0.3 g of $CaCl_2$, 2.5 g of citric acid, 1.0 g of Bacto Peptone, 5.0 g of yeast extract, 1 ml of COVE trace metals solution, and sufficient $K_2HPO_4$ to achieve the final pH of approximately 5.4.

COVE trace metals solution was composed per liter of 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, and 10 g of $ZnSO_4.7H_2O$.

Example 1

Preparation of *Thermoascus aurantiacus* Polypeptide Gh61A Having Cellulolytic Enhancing Activity and *Aspergillus oryzae* Beta-Glucosidase A *Thermoascus aurantiacus* polypeptide GH61A having cellulolytic enhancing activity and *Aspergillus oryzae* beta-glucosidase were prepared by overexpression in *Aspergillus oryzae* The *Thermoascus aurantiacus* polypeptide GH61A having cellulolytic enhancing activity was recombinantly produced in *Aspergillus oryzae* JaL250 according to WO 2005/074656. The *Aspergillus oryzae* beta-glucosidase was recombinantly produced in *Aspergillus oryzae* JaL250 according to WO 02/095014.

Fermentor cultures were grown by cultivating *Aspergillus oryzae* cultures on NNCYP medium supplemented with 52 g of cellulose per liter, which was batched in during fermentation (no additional carbon source) at 42° C. and maintained at pH 5.0. The fermentation was allowed to run until the batch cellulose had been exhausted (typically about 40 hours) at which time the broth was harvested and centrifuged to remove mycelia. Crude broth samples were cleared of cellular debris by centrifuging cultures for approximately 20 minutes at 9500×g. Cleared broth samples were then filtered (MILLEX® GP Express™ membrane, polyethersulfone, 0.22 µm, Millipore, Bedford, Mass., USA). Protein concentrations were determined for desalted material (HIPREP™ 26/10 Desalting Column, AKTA™, GE Healthcare, Piscataway, N.J., USA) using a BCA™ Protein Assay Kit (Pierce, Rockford, Ill., USA) in which bovine serum albumin was used as a protein standard. Aliquots were typically examined on 8-16% CRITERION™ SDS-PAGE gels (Bio-Rad, Hercules, Calif.; 200 V for 1 hour) in which PRECISION PLUS PROTEIN™ molecular weight standards (Bio-Rad, Hercules, Calif., USA) were included. Gels were stained for protein using BIO-SAFE™ Coomassie Stain (Bio-Rad, Hercules, Calif., USA) and destained using deionized water.

FIBREZYME® LDI (Dyadic International, Inc., Jupiter, Fla., USA) was used as received. Protein was determined as above.

Example 2

Pretreatment of Corn Stover

Corn stover was pretreated at the U.S. Department of Energy National Renewable Energy Laboratory (NREL) using dilute sulfuric acid. The following conditions were used for the pretreatment: 1.4 wt % sulfuric acid at 195° C. for 4.5 minutes. According to limit digestion with excess cellulase enzymes, the water-insoluble solids in the pretreated corn stover (PCS) contained 59.5% cellulose. Prior to enzymatic hydrolysis, the PCS was washed with a large volume of deionized water until soluble acid and sugars were removed. The dry weight of the water-washed PCS was found to be 19.16%.

Example 3

Cellulolytic Enhancing Activity of *Thermoascus aurantiacus* Polypeptide GH61A when Combined with *Aspergillus oryzae* Beta-Glucosidase and FIBREZYME® LDI Cellulase Hydrolysis of PCS was conducted using 125 ml screwtop Erlenmeyer flasks (VWR, West Chester, Pa., USA) using a total reaction mass of 50 g as per NREL Laboratory Analytical Protocol #008. In this protocol hydrolysis of PCS (approximately 11.4% in PCS and 6.8% cellulose in aqueous 50 mM sodium acetate pH 5.0 buffer) was performed using different protein loadings (expressed as mg of enzyme per gram of cellulose) of a FIBREZYME® LDI sample (Dyadic International, Inc., Jupiter, Fla., USA) in the absence and presence of 6% *Aspergillus oryzae* beta-glucosidase of cellulase protein loading with and without addition of 11% *Thermoascus aurantiacus* GH61A. Testing of PCS hydrolyzing capability was performed at 50° C. with orbital shaking at 150 rpm (INNOVA® 4080 Incubator, New Brunswick Scientific, Edison, N.J., USA). Aliquots were taken during the course of hydrolysis at 72, 120, and 172 hours. Aliquots were centrifuged, and the supernatant liquid was filtered by centrifugation (MULTISCREEN® HV 0.45 µm, Millipore, Billerica, Mass., USA) at 2000 rpm for 15 minutes using a plate centrifuge (SORVALL® RT7, Thermo Fisher Scientific, Waltham, Mass., USA). When not used immediately, filtered sugary aliquots were frozen at −20° C. Sugar concentrations of samples diluted in 0.005 M $H_2SO_4$ were measured after elution by 0.005 M $H_2SO_4$ at a flow rate of 0.4 ml per minute from a 4.6×250 mm AMINEX® HPX-87H column (Bio-Rad, Hercules, Calif., USA) at 65° C. with quantitation by integration of glucose and cellobiose signal from refractive index detector (CHEMSTATION®, AGILENT® 1100 HPLC, Agilent Technologies, Santa Clara, Calif., USA) calibrated by pure sugar samples. The resultant equivalents were used to calculate the percentage of cellulose conversion for each reaction.

glucose conversion above that obtained by equivalent amounts of protein of FIBREZYME® LDI alone or FIBREZYME™ LDI mixtures with beta-glucosidase. The results for 72 hour hydrolysis are plotted in FIG. 1.

The addition of the *Thermoascus auranticus* GH61A protein to FIBREZYME® LDI-containing solutions increased, therefore, the yield of glucose and cellobiose upon hydrolysis of acid-pretreated corn stover (PCS). The yield increase was higher than that achieved by addition of equal or lesser amounts of FIBREZYME® LDI or equal or lesser amounts of FIBREZYME® LDI admixed with beta-glucosidase, resulting in reduced enzyme loading requirements and increased enzyme efficiency.

TABLE 1

FIBREZYME ® LDI (cellulase), *Aspergillus oryzae* beta-glucosidase (BG) and *Thermoascus aurantiacus* GH61A values are in mg enzyme/g cellulose.

| Mixture of enzymes | % Biomass Content (w/w) | % Cellulose Content (w/w) | Total protein (mg/g cellulose) | FIBREZYME ™ LDI protein (mg/g cellulose) | Protein from FIBREZYME ™ LDI (% w/w) | Protein from BG (% w/w) | Protein from GH61A (% w/w) | conversion 72 hr | conversion 120 hr | conversion 172 hr |
|---|---|---|---|---|---|---|---|---|---|---|
| FIBREZYME ® LDI | 11.32 | 6.70 | 8.0 | 8.0 | 100.0% | 0.0% | 0.0% | 37 | 42 | 45 |
| FIBREZYME ® LDI | 11.42 | 6.76 | 10.5 | 10.5 | 100.0% | 0.0% | 0.0% | 41 | 45 | 49 |
| FIBREZYME ® LDI | 11.45 | 6.78 | 13.6 | 13.6 | 100.0% | 0.0% | 0.0% | 45 | 50 | 53 |
| FIBREZYME ® LDI | 11.45 | 6.78 | 21.1 | 21.1 | 100.0% | 0.0% | 0.0% | 53 | 52 | 55 |
| FIBREZYME ® LDI | 11.53 | 6.82 | 43.3 | 43.3 | 100.0% | 0.0% | 0.0% | 58 | 61 | 64 |
| FIBREZYME ® LDI + BG | 11.44 | 6.77 | 7.1 | 6.6 | 93.2% | 6.8% | 0.0% | 46 | 49 | 52 |
| FIBREZYME ® LDI + BG | 11.46 | 6.78 | 10.5 | 9.8 | 93.2% | 6.8% | 0.0% | 53 | 56 | 58 |
| FIBREZYME ® LDI + BG | 11.43 | 6.76 | 14.5 | 13.5 | 93.3% | 6.7% | 0.0% | 58 | 63 | 65 |
| FIBREZYME ® LDI + BG + 61A | 11.42 | 6.75 | 7.4 | 6.1 | 82.4% | 6.4% | 11.2% | 78 | 78 | 79 |
| FIBREZYME ® LDI + BG + 61A | 11.45 | 6.78 | 10.6 | 8.8 | 82.6% | 6.2% | 11.2% | 80 | 82 | 83 |

Conversion is shown as percent of theoretical glucose available by hydrolysis of PCS.

The degree of cellulose conversion to glucose plus cellobiose sugars (conversion, %) was calculated using the following equation:

$$\text{Conversion}_{(\%)} = (\text{glucose} + \text{cellobiose} \times 1.053)_{(mg/ml)} \times 100 \times 162/(\text{cellulose}_{(mg/ml)} \times 180) = (\text{glucose} + \text{cellobiose} \times 1.053)_{(mg/ml)} \times 100/(\text{cellulose}_{(mg/ml)} \times 1.111)$$

In this equation the factor 1.111 reflects the weight gain in converting cellulose to glucose, and the factor 1.053 reflects the weight gain in converting cellobiose to glucose. Cellulose in PCS was determined by a limit digest of PCS to release glucose and cellobiose.

Enzyme dilutions were prepared fresh before each experiment from stock enzyme solutions, which were stored at 4° C.

The results shown in Table 1 demonstrated that addition of *Aspergillus oryzae* beta-glucosidase to FIBREZYME® LDI to create a mixture of approximately 94% FIBREZYME® LDI and approximately 6% beta-glucosidase increased glucose conversion above that obtained by equivalent amounts of protein of FIBREZYME® LDI alone at protein levels from 7.1 to 43.3 mg/g cellulose. The results shown in Table 1 demonstrated that addition of *Aspergillus oryzae* beta-glucosidase and *Thermoascus auranticus* GH61A to FIBREZYME® LDI to create a mixture of approximately 83% FIBREZYME® LDI with approximately 6% beta-glucosidase and approximately 11% GH61A protein increased Deposits of Biological Material The following biological material has been deposited under the terms of the Budapest Treaty with the Agricultural Research Service Patent Culture Collection, Northern Regional Research Center, 1815 University Street, Peoria, Ill., 61604, and given the following accession numbers:

| Deposit | Accession Number | Date of Deposit |
|---|---|---|
| *E. coli* strain pEJG120 | NRRL B-30699 | Dec. 19, 2003 |
| *E. coli* strain pTter61C | NRRL B-30823 | Jan. 21, 2005 |
| *E. coli* strain pTter61D | NRRL B-30812 | Jan. 21, 2005 |
| *E. coli* strain pTter61E | NRRL B-30814 | Jan. 21, 2005 |
| *E. coli* strain pTter61G | NRRL B-30811 | Jan. 21, 2005 |
| *E. coli* strain pDZA2-7 | NRRL B-30704 | Jan. 30, 2004 |
| *E. coli* strain pTr3337 | NRRL B-30878 | Sep. 20, 2005 |
| *E. coli* TOP10 (pEJG113) | NRRL B-30695 | Oct. 17, 2003 |
| *E. coli* TOP10 pKKAB | NRRL B-30860 | Jul. 8, 2005 |
| NN049573 | DSM 14240 | Apr. 19, 2001 |

The strains have been deposited under conditions that assure that access to the cultures will be available during the pendency of this patent application to one determined by the Commissioner of Patents and Trademarks to be entitled thereto under 37 C.F.R. §1.14 and 35 U.S.C. §122. The depos-

What is claimed is:

1. A cellulolytic enzyme composition, comprising an effective amount of a GH61 polypeptide having cellulolytic enhancing activity, and a CEL7 polypeptide having endoglucanase activity, a CEL12 polypeptide having endoglucanase activity, a CEL45 polypeptide having endoglucanase activity, a CEL7 polypeptide having cellobiohydrolase activity with a cellulose binding domain, a CEL7 polypeptide having cellobiohydrolase activity without a cellulose binding domain, and a polypeptide having beta-glucosidase activity;

wherein the CEL7 polypeptide having endoglucanase activity is selected from the group consisting of: (a) a polypeptide comprising an amino acid sequence having at least 95% sequence identity to the mature polypeptide of SEQ ID NO: 2; (b) a polypeptide encoded by a polynucleotide that hybridizes under at least very high stringency conditions with (i) the mature polypeptide coding sequence of SEQ ID NO: 1, (ii) the genomic DNA sequence comprising the mature polypeptide coding sequence of SEQ ID NO: 1, or (iii) the full-length complement of (i) or (ii); and (c) a polypeptide encoded by a polynucleotide comprising a nucleotide sequence having at least 95% sequence identity to the mature polypeptide coding sequence of SEQ ID NO: 1;

wherein the CEL12 polypeptide having endoglucanase activity is selected from the group consisting of: (a) a polypeptide comprising an amino acid sequence having at least 95% sequence identity to the mature polypeptide of SEQ ID NO: 4; (b) a polypeptide encoded by a polynucleotide that hybridizes under at least very high stringency conditions with (i) the mature polypeptide coding sequence of SEQ ID NO: 3, (ii) the genomic DNA sequence comprising the mature polypeptide coding sequence of SEQ ID NO: 3, or (iii) the full-length complement of (i) or (ii); (c) a polypeptide encoded by a polynucleotide comprising a nucleotide sequence having at least 95% sequence identity to the mature polypeptide coding sequence of SEQ ID NO: 3;

wherein the CEL45 polypeptide having endoglucanase activity is selected from the group consisting of: (a) a polypeptide comprising an amino acid sequence having at least 95% sequence identity to the mature polypeptide of SEQ ID NO: 6; (b) a polypeptide encoded by a polynucleotide that hybridizes under at least very high stringency conditions with (i) the mature polypeptide coding sequence of SEQ ID NO: 5, (ii) the cDNA sequence contained in the mature polypeptide coding sequence of SEQ ID NO: 5, or (iii) the full-length complement of (i) or (ii); and (c) a polypeptide encoded by a polynucleotide comprising a nucleotide sequence having at least 95% sequence identity to the mature polypeptide coding sequence of SEQ ID NO: 5;

wherein the CEL7 polypeptide having cellobiohydrolase activity with a cellulose binding domain is selected from the group consisting of: (a) a polypeptide comprising an amino acid sequence having at least 95% sequence identity to the mature polypeptide of SEQ ID NO: 8; (b) a polypeptide encoded by a polynucleotide that hybridizes under at least very high stringency conditions with (i) the mature polypeptide coding sequence of SEQ ID NO: 7, (ii) the cDNA sequence contained in the mature polypeptide coding sequence of SEQ ID NO: 7, or (iii) the full-length complement of (i) or (ii); and (c) a polypeptide encoded by a polynucleotide comprising a nucleotide sequence having at least 95% sequence identity to the mature polypeptide coding sequence of SEQ ID NO: 7;

wherein the CEL7 polypeptide having cellobiohydrolase activity without a cellulose binding domain is selected from the group consisting of: (a) a polypeptide comprising an amino acid sequence having at least 95% sequence identity to the mature polypeptide of SEQ ID NO: 10; (b) a polypeptide encoded by a polynucleotide that hybridizes under at least very high stringency conditions with (i) the mature polypeptide coding sequence of SEQ ID NO: 9, (ii) the cDNA sequence contained in or the genomic DNA sequence comprising the mature polypeptide coding sequence of SEQ ID NO: 9, or (iii) the full-length complement of (i) or (ii); and (c) a polypeptide encoded by a polynucleotide comprising a nucleotide sequence having at least 95% sequence identity to the mature polypeptide coding sequence of SEQ ID NO: 9;

wherein very high stringency conditions are defined as prehybridization and hybridization at 42° C. in 5×SSPE, 0.3% SDS, 200 µg/ml sheared and denatured salmon sperm DNA, and 50% formamide and washing three times each for 15 minutes using 2×SSC, 0.2% SDS at 70° C.; and wherein the presence of the GH61 polypeptide having cellulolytic enhancing activity increases the degradation of a cellulose-containing material by the cellulolytic enzyme composition compared to the absence of the GH61 polypeptide having cellulolytic enhancing activity and wherein the effective amount of the GH61 polypeptide to the cellulolytic proteins of the enzyme composition is about 0.005 to about 1.0 g per g of the cellulolytic proteins.

2. The cellulolytic enzyme composition of claim 1, wherein the CEL7 polypeptide having endoglucanase activity comprises the mature polypeptide of SEQ ID NO: 2 or a fragment thereof having endoglucanase activity, the CEL12 polypeptide having endoglucanase activity comprises the mature polypeptide of SEQ ID NO: 4 or a fragment thereof having endoglucanase activity, the CEL45 polypeptide having endoglucanase activity comprises the mature polypeptide of SEQ ID NO: 6 or a fragment thereof having endoglucanase activity, the CEL7 polypeptide having cellobiohydrolase activity with a cellulose binding domain comprises the mature polypeptide of SEQ ID NO: 8 or a fragment thereof having cellobiohydrolase activity, and the CEL7 polypeptide having cellobiohydrolase activity without a cellulose binding domain comprises the mature polypeptide of SEQ ID NO: 10 or a fragment thereof having cellobiohydrolase activity.

3. The cellulolytic enzyme composition of claim 1, wherein the GH61 polypeptide having cellulolytic enhancing activity is selected from the group consisting of:
  (a) a GH61 polypeptide having cellulolytic enhancing activity comprising [ILMV]-P-X(4,5)-G-X-Y-[ILMV]-X-R-X-[EQ]-X(4)-[HNQ] (SEQ ID NO: 31 or SEQ ID NO: 32) and [FW]-[TF]-K-[AIV] (SEQ ID NO: 41 ), wherein X is any amino acid, X(4,5) is any amino acid at 4 or 5 contiguous positions, and X(4) is any amino acid at 4 contiguous positions; and
  (b) a GH61 polypeptide having cellulolytic enhancing activity comprising [ILMV]-P-X(4,5)-G-X-Y-[ILMV]-X-R-X-[EQ]-X(3)-A-[HNQ] (SEQ ID NO: 39 or SEQ ID NO: 40), wherein X is any amino acid, X(4,5) is any amino acid at 4 or 5 contiguous positions, and X(3) is any amino acid at 3 contiguous positions.

4. The cellulolytic enzyme composition of claim 3, wherein the GH61 polypeptide having cellulolytic enhancing activity comprising [ILMV]-P-X(4,5)-G-X-Y-[ILMV]-X-R-X-[EQ]-X(4)-[HNQ] (SEQ ID NO: 31 or SEQ ID NO: 32) and [FW]-[TF]-K-[AIV] (SEQ ID NO: 41) further comprises:
  H-X(1,2)-G-P-X(3)-[YW]-[AILMV] (SEQ ID NO: 33 or SEQ ID NO: 34),
  [EQ]-X-Y-X(2)-C-X-[EHQN]-[FILV]-X-[ILV] (SEQ ID NO: 35), or
  H-X(1,2)-G-P-X(3)-[YW]-[AILMV] (SEQ ID NO: 36 or SEQ ID NO: 37) and [EQ]-X-Y-X(2)-C-X-[EHQN]-[FILV]-X-[ILV] (SEQ ID NO: 38), wherein X is any amino acid, X(1,2) is any amino acid at 1 position or 2 contiguous positions, X(3) is any amino acid at 3 contiguous positions, and X(2) is any amino acid at 2 contiguous positions.

5. The cellulolytic enzyme composition of claim 1, wherein the GH61 polypeptide having cellulolytic enhancing activity is selected from the group consisting of:
  (a) a polypeptide comprising an amino acid sequence having at least 95% sequence identity to the mature polypeptide of SEQ ID NO: 12, SEQ ID NO: 14, SEQ ID NO: 16, SEQ ID NO: 18, or SEQ ID NO: 20, SEQ ID NO: 22, or SEQ ID NO: 24;
  (b) a polypeptide encoded by a polynucleotide that hybridizes under at least very high stringency conditions with (i) the mature polypeptide coding sequence of SEQ ID NO: 11, SEQ ID NO: 13, SEQ ID NO: 15, SEQ ID NO: 17, SEQ ID NO: 19, SEQ ID NO: 21, or SEQ ID NO: 23, (ii) the cDNA sequence contained in the mature polypeptide coding sequence of SEQ ID NO: 11, SEQ ID NO: 13, SEQ ID NO: 15, or SEQ ID NO: 21, or the genomic DNA sequence comprising the mature polypeptide coding sequence of SEQ ID NO: 17, SEQ ID NO: 19, or SEQ ID NO: 23, or (iii) the full-length complement of (i) or (ii); wherein very high stringency conditions are defined as prehybridization and hybridization at 42° C. in 5×SSPE, 0.3% SDS, 200 µg/ml sheared and denatured salmon sperm DNA, and 50% formamide and washing three times each for 15 minutes using 2×SSC, 0.2% SDS at 70° C.; and
  (c) a polypeptide encoded by a polynucleotide comprising a nucleotide sequence having at least 95% sequence identity to the mature polypeptide coding sequence of SEQ ID NO: 11, SEQ ID NO: 13, SEQ ID NO: 15, SEQ ID NO: 17, SEQ ID NO: 19, SEQ ID NO: 21, or SEQ ID NO: 23.

6. The cellulolytic enzyme composition of claim 1, wherein the effective amount of the GH61 polypeptide to the cellulolytic proteins of the enzyme composition is about 0.01 to about 1.0 g per g of the cellulolytic proteins.

7. The cellulolytic enzyme composition of claim 1, wherein the effective amount of the GH61 polypeptide to the cellulolytic proteins of the enzyme composition is about 0.1 to about 0.5 g per g of the cellulolytic proteins.

8. The cellulolytic enzyme composition of claim 1, wherein the effective amount of the GH61 polypeptide to the cellulolytic proteins of the enzyme composition is about 0.15 to about 0.75 g per g of the cellulolytic proteins.

9. The cellulolytic enzyme composition of claim 1, wherein the effective amount of the GH61 polypeptide to the cellulolytic proteins of the enzyme composition is about 0.05 to about 0.2 g per g of the cellulolytic proteins.

10. The cellulolytic enzyme composition of claim 1, wherein the effective amount of the GH61 polypeptide to the cellulose-containing material is about 0.01 to about 50.0 mg per g of the cellulose-containing material.

11. The cellulolytic enzyme composition of claim 1, wherein the effective amount of the GH61 polypeptide to the cellulose-containing material is about 0.01 to about 20 mg per g of the cellulose-containing material.

12. The cellulolytic enzyme composition of claim 1, wherein the effective amount of the GH61 polypeptide to the cellulose-containing material is about 0.01 to about 10 mg per g of the cellulose-containing material.

13. The cellulolytic enzyme composition of claim 1, wherein the effective amount of the GH61 polypeptide to the cellulose-containing material is about 0.01 to about 5 mg per g of the cellulose-containing material.

14. The cellulolytic enzyme composition of claim 1, wherein the effective amount of the GH61 polypeptide to the cellulose-containing material is about 0.025 to about 1.5 mg per g of the cellulose-containing material.

15. The cellulolytic enzyme composition of claim 1, wherein the effective amount of the GH61 polypeptide to the cellulose-containing material is about 0.05 to about 1.25 mg per g of the cellulose-containing material.

16. The cellulolytic enzyme composition of claim 1, wherein the effective amount of the GH61 polypeptide to the cellulose-containing material is about 0.075 to about 1.25 mg per g of the cellulose-containing material.

17. The cellulolytic enzyme composition of claim 1, wherein the effective amount of the GH61 polypeptide to the cellulose-containing material is about 0.1 to about 1.25 mg per g of the cellulose-containing material.

18. The cellulolytic enzyme composition of claim 1, wherein the effective amount of the GH61 polypeptide to the cellulose-containing material is about 0.15 to about 1.25 mg per g of the cellulose-containing material.

19. The cellulolytic enzyme composition of claim 1, wherein the effective amount of the GH61 polypeptide to the cellulose-containing material is about 0.25 to about 1.0 mg per g of the cellulose-containing material.

* * * * *

SEQUENCE LISTING

```
<160> NUMBER OF SEQ ID NOS: 41

<210> SEQ ID NO 1
<211> LENGTH: 1371
<212> TYPE: DNA
<213> ORGANISM: Myceliophthora thermophila

<400> SEQUENCE: 1
atgggtcgcg gcgctgcttt cctaggcctc gcctcgctcc tcgtgggcgc ggccaaggcc        60
cagacgcccg gcgagggcga ggaggtgcac ccgcagatca cgacgtaccg ctgcaccaag       120
gcggacgggt gcgaggagaa gaccaactac atcgtgctgg acgccctatc gcacccggtc       180
caccaggtcg acaacccgta caactgcggc gactggggcc agaagcccaa cgagacggcc       240
tgcccggacc tcgagtcgtg cgccaggaac tgcatcatgg acccggtctc ggactacggc       300
cggcacggtg tctcgaccga cggcacctcg ctgcgcctca gcagctagt cggcggcaac       360 gtcgtcagcc cgcgcgtcta cctgctcgac gagaccaagg agcgctacga gatgctcaag       420
ctgaccggca acgagttcac ctttgacgtc gacgccacca gctgccctg cggcatgaac       480 agcgccctct acctctccga gatggacgcc accggcgccc ggagcgagct caacccgggc       540
ggcgccacct ttggcaccgg ctactgcgac gcccagtgct acgtcacccc cttcatcaac       600
ggcctcggca acatcgaggg caaggcgcg tgctgcaacg agatggatat ctgggaggcc       660
aacgcgcggg cgcagcacat cgcgccgcac ccgtgcagca aggcggggcc gtacctgtgc       720
gagggcgccg agtgcgagtt cgacggcgtg tgcgacaaga acggctgcgc ctggaacccg       780
taccgggtca acgtgacgga ctactacggc gagggcgccg agttcagggt ggacacgacc       840
cggcccttct cggtcgtcac gcagttccgc gccggcggcg acgcggggg cggcaagctc       900 gagagcatct accggctctt cgtccaggac ggcagggtga ttgagtcgta cgtcgtcgac       960
aagcccggcc tgcccccgac ggaccgcatg acggacgagt tctgcgccgc caccggcgcc      1020
gcccgcttca cggagctcgg cgccatggag gccatgggcg acgccctgac gcgcggcatg      1080
gtcctcgccc tcagcatctg gtggagcgag ggcgacaaca tgaactggct cgactcgggc      1140
gaggccggcc cctgcgaccc ggacgagggc aacccgtcca acatcatccg cgtccagccc      1200
gacccggagg tcgtcttcag caacctgcgc tggggcgaga tcggctcaac ctacgagtcc      1260
gccgtcgacg ggcccgtcgg caagggcaag ggcaagggca agggcaaggc tcccgccggc      1320
gacggcaacg ggaaggagaa gagcaatggc aagcgcttca ggaggttctg a             1371

<210> SEQ ID NO 2
<211> LENGTH: 456
<212> TYPE: PRT
<213> ORGANISM: Myceliophthora thermophila

<400> SEQUENCE: 2

Met Gly Arg Gly Ala Ala Phe Leu Gly Leu Ala Ser Leu Leu Val Gly
1               5                   10                  15
```

```
Ala Ala Lys Ala Gln Thr Pro Gly Glu Gly Glu Val His Pro Gln
         20                  25                  30

Ile Thr Thr Tyr Arg Cys Thr Lys Ala Asp Gly Cys Glu Glu Lys Thr
             35                  40                  45

Asn Tyr Ile Val Leu Asp Ala Leu Ser His Pro Val His Gln Val Asp
 50                  55                  60

Asn Pro Tyr Asn Cys Gly Asp Trp Gly Gln Lys Pro Asn Glu Thr Ala
 65                  70                  75                  80

Cys Pro Asp Leu Glu Ser Cys Ala Arg Asn Cys Ile Met Asp Pro Val
                 85                  90                  95

Ser Asp Tyr Gly Arg His Gly Val Ser Thr Asp Gly Thr Ser Leu Arg
            100                 105                 110

Leu Lys Gln Leu Val Gly Gly Asn Val Val Ser Pro Arg Val Tyr Leu
            115                 120                 125

Leu Asp Glu Thr Lys Glu Arg Tyr Glu Met Leu Lys Leu Thr Gly Asn
130                 135                 140

Glu Phe Thr Phe Asp Val Asp Ala Thr Lys Leu Pro Cys Gly Met Asn
145                 150                 155                 160

Ser Ala Leu Tyr Leu Ser Glu Met Asp Ala Thr Gly Ala Arg Ser Glu
                165                 170                 175

Leu Asn Pro Gly Gly Ala Thr Phe Gly Thr Gly Tyr Cys Asp Ala Gln
            180                 185                 190

Cys Tyr Val Thr Pro Phe Ile Asn Gly Leu Gly Asn Ile Glu Gly Lys
            195                 200                 205

Gly Ala Cys Cys Asn Glu Met Asp Ile Trp Glu Ala Asn Ala Arg Ala
210                 215                 220

Gln His Ile Ala Pro His Pro Cys Ser Lys Ala Gly Pro Tyr Leu Cys
225                 230                 235                 240

Glu Gly Ala Glu Cys Glu Phe Asp Gly Val Cys Asp Lys Asn Gly Cys
                245                 250                 255

Ala Trp Asn Pro Tyr Arg Val Asn Val Thr Asp Tyr Tyr Gly Glu Gly
            260                 265                 270

Ala Glu Phe Arg Val Asp Thr Thr Arg Pro Phe Ser Val Val Thr Gln
            275                 280                 285

Phe Arg Ala Gly Gly Asp Ala Gly Gly Lys Leu Glu Ser Ile Tyr
290                 295                 300

Arg Leu Phe Val Gln Asp Gly Arg Val Ile Glu Ser Tyr Val Val Asp
305                 310                 315                 320

Lys Pro Gly Leu Pro Pro Thr Asp Arg Met Thr Asp Glu Phe Cys Ala
                325                 330                 335

Ala Thr Gly Ala Ala Arg Phe Thr Glu Leu Gly Ala Met Glu Ala Met
            340                 345                 350

Gly Asp Ala Leu Thr Arg Gly Met Val Leu Ala Leu Ser Ile Trp Trp
            355                 360                 365

Ser Glu Gly Asp Asn Met Asn Trp Leu Asp Ser Gly Glu Ala Gly Pro
            370                 375                 380

Cys Asp Pro Asp Glu Gly Asn Pro Ser Asn Ile Ile Arg Val Gln Pro
385                 390                 395                 400

Asp Pro Glu Val Val Phe Ser Asn Leu Arg Trp Gly Glu Ile Gly Ser
                405                 410                 415

Thr Tyr Glu Ser Ala Val Asp Gly Pro Val Gly Lys Gly Lys Gly Lys
            420                 425                 430
```

```
Gly Lys Gly Lys Ala Pro Ala Gly Asp Gly Asn Gly Lys Glu Lys Ser
            435                 440                 445

Asn Gly Lys Arg Phe Arg Arg Phe
    450                 455

<210> SEQ ID NO 3
<211> LENGTH: 744
<212> TYPE: DNA
<213> ORGANISM: Chrysosoporium lucknowense

<400> SEQUENCE: 3
atgcagccgt tctgctctt gttcctctcg tcggtcacgg cggcgagccc cctgacggcg      60
ctcgacaagc ggcagcaggc gacgttgtgc gagcagtacg gctactggtc gggcaacggt     120
tacgaggtca acaacaacaa ctggggcaag gattcggcct cggcggcca tcagtgcacc      180 tacgtcgaca gcagcagctc cagcggcgtc gcctggcaca cgacctggca gtgggaagga     240
ggccagaacc aggtcaagag cttcgccaac tgcggcctgc aggtgcccaa gggcaggacc     300
atctcgtcca tcagcaacct gcagacctcc atctcgtggt cctacagcaa caccaacatc     360
cgcgccaacg tggcctacga cctcttcacc gcggcagacc cgaaccacgc gaccagcagc     420
ggcgactacg agctcatgat ctggctggcg agattcggcg acgtctaccc catcggctcg     480
tcccagggcc acgtcaacgt ggccggccag gactgggagc tgtggacggg cttcaacggc     540
aacatgcggg tctacagctt cgtagcgccc agccccgca acagcttcag cgccaacgtc     600
aaggacttct tcaactatct ccagtccaac cagggcttcc cggccagcag ccaataccct     660
ctcatcttcc aggcgggcac cgagcccttc accggcggcg agaccaccct taccgtcaac     720
aactactctg caagggttgc ttaa                                            744

<210> SEQ ID NO 4
<211> LENGTH: 247
<212> TYPE: PRT
<213> ORGANISM: Chrysosoporium lucknowense

<400> SEQUENCE: 4

Met Gln Pro Phe Leu Leu Leu Phe Leu Ser Ser Val Thr Ala Ala Ser
1               5                   10                  15

Pro Leu Thr Ala Leu Asp Lys Arg Gln Gln Ala Thr Leu Cys Glu Gln
            20                  25                  30

Tyr Gly Tyr Trp Ser Gly Asn Gly Tyr Glu Val Asn Asn Asn Asn Trp
        35                  40                  45

Gly Lys Asp Ser Ala Ser Gly Gly His Gln Cys Thr Tyr Val Asp Ser
    50                  55                  60

Ser Ser Ser Ser Gly Val Ala Trp His Thr Thr Trp Gln Trp Glu Gly
65                  70                  75                  80

Gly Gln Asn Gln Val Lys Ser Phe Ala Asn Cys Gly Leu Gln Val Pro
                85                  90                  95

Lys Gly Arg Thr Ile Ser Ser Ile Ser Asn Leu Gln Thr Ser Ile Ser
            100                 105                 110

Trp Ser Tyr Ser Asn Thr Asn Ile Arg Ala Asn Val Ala Tyr Asp Leu
        115                 120                 125

Phe Thr Ala Ala Asp Pro Asn His Ala Thr Ser Ser Gly Asp Tyr Glu
    130                 135                 140

Leu Met Ile Trp Leu Ala Arg Phe Gly Asp Val Tyr Pro Ile Gly Ser
145                 150                 155                 160

Ser Gln Gly His Val Asn Val Ala Gly Gln Asp Trp Glu Leu Trp Thr
```

-continued

```
                165                 170                 175

Gly Phe Asn Gly Asn Met Arg Val Tyr Ser Phe Val Ala Pro Ser Pro
            180                 185                 190

Arg Asn Ser Phe Ser Ala Asn Val Lys Asp Phe Phe Asn Tyr Leu Gln
        195                 200                 205

Ser Asn Gln Gly Phe Pro Ala Ser Ser Gln Tyr Leu Leu Ile Phe Gln
    210                 215                 220

Ala Gly Thr Glu Pro Phe Thr Gly Gly Glu Thr Thr Leu Thr Val Asn
225                 230                 235                 240

Asn Tyr Ser Ala Arg Val Ala
                245

<210> SEQ ID NO 5
<211> LENGTH: 678
<212> TYPE: DNA
<213> ORGANISM: Chrysosoporium lucknowense

<400> SEQUENCE: 5
atgcatctct ccgccaccac cgggttcctc gccctcccgg ccctggccct ggcccagctc      60
tcgggcagcg gccagacgac ccggtactgg gactgctgca agccgagctg cgcctggccc     120
ggcaagggcc cctcgtctcc ggtgcaggcc tgcgacaaga acgacaaccc gctcaacgac     180
ggcggctcca cccggtccgg ctgcgacgcg ggcggcagcg cctacatgtg ctcctcccag     240
agcccctggg ccgtcagcga cgagctgtcg tacggctggg cggccgtcaa gctcgccggc     300
agctccgagt cgcagtggtg ctgcgcctgc tacgagctga ccttcaccag cgggccggtc     360
gcgggcaaga agatgattgt gcaggcgacc aacaccggtg gcgacctggg cgacaaccac     420
tttgacctgg ccatccccgg tggcggtgtc ggtattttca acgcctgcac cgaccagtac     480
ggcgctcccc cgaacggctg gggcgaccgc tacggcggca tccattccaa ggaagagtgc     540
gaatccttcc cggaggccct caagcccggc tgcaactggc gcttcgactg gttccaaaac     600
gccgacaacc cgtcggtcac cttccaggag gtggcctgcc cgtcggagct cacgtccaag     660
agcggctgct cccgttaa                                                   678

<210> SEQ ID NO 6
<211> LENGTH: 225
<212> TYPE: PRT
<213> ORGANISM: Chrysosoporium lucknowense

<400> SEQUENCE: 6

Met His Leu Ser Ala Thr Thr Gly Phe Leu Ala Leu Pro Ala Leu Ala
1               5                   10                  15

Leu Ala Gln Leu Ser Gly Ser Gly Gln Thr Thr Arg Tyr Trp Asp Cys
            20                  25                  30

Cys Lys Pro Ser Cys Ala Trp Pro Gly Lys Gly Pro Ser Ser Pro Val
        35                  40                  45

Gln Ala Cys Asp Lys Asn Asp Asn Pro Leu Asn Asp Gly Gly Ser Thr
    50                  55                  60

Arg Ser Gly Cys Asp Ala Gly Gly Ser Ala Tyr Met Cys Ser Ser Gln
65                  70                  75                  80

Ser Pro Trp Ala Val Ser Asp Glu Leu Ser Tyr Gly Trp Ala Ala Val
                85                  90                  95

Lys Leu Ala Gly Ser Ser Glu Ser Gln Trp Cys Cys Ala Cys Tyr Glu
            100                 105                 110

Leu Thr Phe Thr Ser Gly Pro Val Ala Gly Lys Lys Met Ile Val Gln
```

```
                    115                 120                 125
Ala Thr Asn Thr Gly Gly Asp Leu Gly Asp Asn His Phe Asp Leu Ala
        130                 135                 140

Ile Pro Gly Gly Gly Val Gly Ile Phe Asn Ala Cys Thr Asp Gln Tyr
145                 150                 155                 160

Gly Ala Pro Pro Asn Gly Trp Gly Asp Arg Tyr Gly Gly Ile His Ser
                165                 170                 175

Lys Glu Glu Cys Glu Ser Phe Pro Glu Ala Leu Lys Pro Gly Cys Asn
            180                 185                 190

Trp Arg Phe Asp Trp Phe Gln Asn Ala Asp Asn Pro Ser Val Thr Phe
                195                 200                 205

Gln Glu Val Ala Cys Pro Ser Glu Leu Thr Ser Lys Ser Gly Cys Ser
    210                 215                 220

Arg
225

<210> SEQ ID NO 7
<211> LENGTH: 1648
<212> TYPE: DNA
<213> ORGANISM: Chrysosoporium lucknowense
<220> FEATURE:
<221> NAME/KEY: misc_feature
<222> LOCATION: (1162)..(1162)
<223> OTHER INFORMATION: N= A, C, G, OR T

<400> SEQUENCE: 7
atgtacgcca agttcgcgac cctcgccgcc cttgtggctg gcgccgctgc tcagaacgcc      60
tgcactctga ccgctgagaa ccaccccctcg ctgacgtggt ccaagtgcac gtctggcggc     120
agctgcacca gcgtccaggg ttccatcacc atcgacgcca actggcggtg gactcaccgg     180
accgatagcg ccaccaactg ctacgagggc aacaagtggg atacttcgta ctgcagcgat     240
ggtccttctt gcgcctccaa gtgctgcatc gacggcgctg actactcgag cacctatggc     300
atcaccacga gcggtaactc cctgaacctc aagttcgtca ccaagggcca gtactcgacc     360
aacatcggct cgcgtaccta cctgatggag agcgacacca gtaccagag taagttcctc      420 tcgcacccgg ccgccgggag atgatggcgc ccagcccgct gacgcgaatg acacagtgtt     480
ccagctcctc ggcaacgagt tcaccttcga tgtcgacgtc tccaacctcg gctgcggcct     540
caatggcgcc ctctacttcg tgtccatgga tgccgatggt ggcatgtcca agtactcggg     600
caacaaggca ggtgccaagt acggtaccgg ctactgtgat tctcagtgcc ccgcgaccct     660
caagttcatc aacggcgagg ccaacgtaga gaactggcag agctcgacca acgatgccaa     720
cgccggcacg ggcaagtacg gcagctgctg ctccgagatg gacgtctggg aggccaacaa     780
catggccgcc gccttcactc cccaccctg accgtgatc ggccagtcgc gctgcgaggg      840
cgactcgtgc ggcggtacct acagcaccga ccgctatgcc ggcatctgcg accccgacgg     900
atgcgacttc aactcgtacc gccagggcaa caagaccttc tacggcaagg gcatgacggt     960
cgacacgacc aagaagatca cggtcgtcac ccagttcctc aagaactcgg ccggcgagct    1020
ctccgagatc aagcggttct acgtccagaa cggcaaggtc atccccaact ccgagtccac    1080
catcccgggc gtcgagggca actccatcac ccaggactgg tgcgaccgcc agaaggccgc    1140
cttcggcgac gtgaccgact ncaggacaa gggcggcatg gtccagatgg caaggccct     1200 cgcggggccc atggtcctcg tcatgtccat ctgggacgac cacgccgtca acatgctctg    1260
gctcgactcc acctggccca tcgacggcgc cggcaagccg ggcgccgagc gcggtgcctg    1320
```

```
cccaccacc tcgggcgtcc ccgctgaggt cgaggccgag gcccccaact ccaacgtcat   1380
cttctccaac atccgcttcg gccccatcgg ctccaccgtc tccggcctgc ccgacggcgg   1440
cagcggcaac cccaacccgc ccgtcagctc gtccaccccg gtccctcct cgtccaccac   1500 atcctccggt tcctccggcc cgactggcgg cacgggtgtc gctaagcact atgagcaatg   1560
cggaggaatc gggttcactg ccctacccca gtgcgagagc ccctacactt gcaccaagct   1620
gaatgactgg tactcgcagt gcctgtaa                                      1648
```

```
<210> SEQ ID NO 8
<211> LENGTH: 526
<212> TYPE: PRT
<213> ORGANISM: Chrysosoporium lucknowense
<220> FEATURE:
<221> NAME/KEY: MISC_FEATURE
<222> LOCATION: (365)..(365)
<223> OTHER INFORMATION: X= any amino acid

<400> SEQUENCE: 8
```

```
Met Tyr Ala Lys Phe Ala Thr Leu Ala Ala Leu Val Ala Gly Ala Ala
  1               5                  10                  15

Ala Gln Asn Ala Cys Thr Leu Thr Ala Glu Asn His Pro Ser Leu Thr
             20                  25                  30

Trp Ser Lys Cys Thr Ser Gly Gly Ser Cys Thr Ser Val Gln Gly Ser
         35                  40                  45

Ile Thr Ile Asp Ala Asn Trp Arg Trp Thr His Arg Thr Asp Ser Ala
     50                  55                  60

Thr Asn Cys Tyr Glu Gly Asn Lys Trp Asp Thr Ser Tyr Cys Ser Asp
 65                  70                  75                  80

Gly Pro Ser Cys Ala Ser Lys Cys Cys Ile Asp Gly Ala Asp Tyr Ser
                 85                  90                  95

Ser Thr Tyr Gly Ile Thr Thr Ser Gly Asn Ser Leu Asn Leu Lys Phe
            100                 105                 110

Val Thr Lys Gly Gln Tyr Ser Thr Asn Ile Gly Ser Arg Thr Tyr Leu
        115                 120                 125

Met Glu Ser Asp Thr Lys Tyr Gln Met Phe Gln Leu Leu Gly Asn Glu
    130                 135                 140

Phe Thr Phe Asp Val Asp Val Ser Asn Leu Gly Cys Gly Leu Asn Gly
145                 150                 155                 160

Ala Leu Tyr Phe Val Ser Met Asp Ala Asp Gly Gly Met Ser Lys Tyr
                165                 170                 175

Ser Gly Asn Lys Ala Gly Ala Lys Tyr Gly Thr Gly Tyr Cys Asp Ser
            180                 185                 190

Gln Cys Pro Arg Asp Leu Lys Phe Ile Asn Gly Glu Ala Asn Val Glu
        195                 200                 205

Asn Trp Gln Ser Ser Thr Asn Asp Ala Asn Ala Gly Thr Gly Lys Tyr
    210                 215                 220

Gly Ser Cys Cys Ser Glu Met Asp Val Trp Glu Ala Asn Asn Met Ala
225                 230                 235                 240

Ala Ala Phe Thr Pro His Pro Cys Trp Val Ile Gly Gln Ser Arg Cys
                245                 250                 255

Glu Gly Asp Ser Cys Gly Gly Thr Tyr Ser Thr Asp Arg Tyr Ala Gly
            260                 265                 270

Ile Cys Asp Pro Asp Gly Cys Asp Phe Asn Ser Tyr Arg Gln Gly Asn
        275                 280                 285

Lys Thr Phe Tyr Gly Lys Gly Met Thr Val Asp Thr Thr Lys Lys Ile
```

```
              290                 295                 300
Thr Val Thr Gln Phe Leu Lys Asn Ser Ala Gly Glu Leu Ser Glu
305                 310                 315                 320

Ile Lys Arg Phe Tyr Val Gln Asn Gly Lys Val Ile Pro Asn Ser Glu
                325                 330                 335

Ser Thr Ile Pro Gly Val Glu Gly Asn Ser Ile Thr Gln Asp Trp Cys
                340                 345                 350

Asp Arg Gln Lys Ala Ala Phe Gly Asp Val Thr Asp Xaa Gln Asp Lys
                355                 360                 365

Gly Gly Met Val Gln Met Gly Lys Ala Leu Ala Gly Pro Met Val Leu
                370                 375                 380

Val Met Ser Ile Trp Asp Asp His Ala Val Asn Met Leu Trp Leu Asp
385                 390                 395                 400

Ser Thr Trp Pro Ile Asp Gly Ala Gly Lys Pro Gly Ala Glu Arg Gly
                405                 410                 415

Ala Cys Pro Thr Thr Ser Gly Val Pro Ala Glu Val Glu Ala Glu Ala
                420                 425                 430

Pro Asn Ser Asn Val Ile Phe Ser Asn Ile Arg Phe Gly Pro Ile Gly
                435                 440                 445

Ser Thr Val Ser Gly Leu Pro Asp Gly Gly Ser Gly Asn Pro Asn Pro
                450                 455                 460

Pro Val Ser Ser Ser Thr Pro Val Pro Ser Ser Thr Thr Ser Ser
465                 470                 475                 480

Gly Ser Ser Gly Pro Thr Gly Gly Thr Gly Val Ala Lys His Tyr Glu
                485                 490                 495

Gln Cys Gly Gly Ile Gly Phe Thr Gly Pro Thr Gln Cys Glu Ser Pro
                500                 505                 510

Tyr Thr Cys Thr Lys Leu Asn Asp Trp Tyr Ser Gln Cys Leu
                515                 520                 525

<210> SEQ ID NO 9
<211> LENGTH: 1353
<212> TYPE: DNA
<213> ORGANISM: Myceliophthora thermophila

<400> SEQUENCE: 9
atgaagcagt acctccagta cctcgcggcg accctgcccc tggtgggcct ggccacggcc      60
cagcaggcgg gtaacctgca gaccgagact cacccccagg ctcacttggt caagtgcacg     120
gccccgggat cctgccaaca ggtcaacggc gaggtcgtca tcgactccaa ctggcgctgg     180
gtgcacgacg agaacgcgca gaactgctac gacggcaacc agtggaccaa cgcttgcagc     240
tctgccaccg actgcgccga gaattgcgcg ctcgagggtg ccgactacca gggcacctat     300
ggcgcctcga ccagcggcaa tgccctgacg ctcaccttcg tcactaagca cgagtacggc     360
accaacattg gctcgcgcct ctacctcatg aacggcgcga acaagtacca gatgttcacc     420
ctcaagggca acgagctggc cttcgacgtc gacctctcgg ccgtcgagtg cggcctcaac     480
agcgccctct acttcgtggc catggaggag gatggcggtg tgtcgagcta cccgaccaac     540
acggccggtg ctaagttcgg cactgggtac tgcgacgccc aatgcgcacg cgacctcaag     600
ttcgtcggcg gcaagggcaa catcgagggc tggaagccgt ccaccaacga tgccaatgcc     660
ggtgtcggtc cttatggcgg tgctgcgcgt gagatcgacg tctgggagtc gaacaagtat     720
gctttcgctt caccccgca cggttgcgag aaccctaaat accacgtctg cgagaccacc     780
aactgcggtg gcacctactc cgaggaccgc ttcgctggtg actgcgatgc caacggctgc     840
```

```
gactacaacc cctaccgcat gggcaaccag gacttctacg gtcccggctt gacggtcgat    900
accagcaaga agttcaccgt cgtcagccag ttcgaggaga acaagctcac ccagttcttc    960
gtccaggacg caagaagat tgagatcccc ggccccaagg tcgagggcat cgatgcggac   1020
agcgccgcta tcaccccga gctgtgcagt gccctgttca aggccttcga tgaccgtgac   1080
cgcttctcgg aggttggcgg cttcgatgcc atcaacacgg ccctcagcac tcccatggtc   1140
ctcgtcatgt ccatctggga tgatcactac gccaatatgc tctggctcga ctcgagctac   1200 cccctgaga aggctggcca gctggcggt gaccgtggcc cgtgtcctca ggactctggc   1260 gtccggccg acgttgaggc tcagtaccct aatgccaagg tcatctggtc caacatccgc   1320
ttcggcccca tcggctcgac tgtcaacgtc taa                              1353
```

<210> SEQ ID NO 10
<211> LENGTH: 450
<212> TYPE: PRT
<213> ORGANISM: Myceliophthora thermophila

<400> SEQUENCE: 10

```
Met Lys Gln Tyr Leu Gln Tyr Leu Ala Ala Thr Leu Pro Leu Val Gly
1               5                   10                  15

Leu Ala Thr Ala Gln Gln Ala Gly Asn Leu Gln Thr Glu Thr His Pro
            20                  25                  30

Arg Leu Thr Trp Ser Lys Cys Thr Ala Pro Gly Ser Cys Gln Gln Val
        35                  40                  45

Asn Gly Glu Val Val Ile Asp Ser Asn Trp Arg Trp Val His Asp Glu
    50                  55                  60

Asn Ala Gln Asn Cys Tyr Asp Gly Asn Gln Trp Thr Asn Ala Cys Ser
65                  70                  75                  80

Ser Ala Thr Asp Cys Ala Glu Asn Cys Ala Leu Glu Gly Ala Asp Tyr
                85                  90                  95

Gln Gly Thr Tyr Gly Ala Ser Thr Ser Gly Asn Ala Leu Thr Leu Thr
            100                 105                 110

Phe Val Thr Lys His Glu Tyr Gly Thr Asn Ile Gly Ser Arg Leu Tyr
        115                 120                 125

Leu Met Asn Gly Ala Asn Lys Tyr Gln Met Phe Thr Leu Lys Gly Asn
    130                 135                 140

Glu Leu Ala Phe Asp Val Asp Leu Ser Ala Val Glu Cys Gly Leu Asn
145                 150                 155                 160

Ser Ala Leu Tyr Phe Val Ala Met Glu Glu Asp Gly Gly Val Ser Ser
                165                 170                 175

Tyr Pro Thr Asn Thr Ala Gly Ala Lys Phe Gly Thr Gly Tyr Cys Asp
            180                 185                 190

Ala Gln Cys Ala Arg Asp Leu Lys Phe Val Gly Gly Lys Gly Asn Ile
        195                 200                 205

Glu Gly Trp Lys Pro Ser Thr Asn Asp Ala Asn Ala Gly Val Gly Pro
    210                 215                 220

Tyr Gly Gly Cys Cys Ala Glu Ile Asp Val Trp Glu Ser Asn Lys Tyr
225                 230                 235                 240

Ala Phe Ala Phe Thr Pro His Gly Cys Glu Asn Pro Lys Tyr His Val
                245                 250                 255

Cys Glu Thr Thr Asn Cys Gly Gly Thr Tyr Ser Glu Asp Arg Phe Ala
            260                 265                 270

Gly Asp Cys Asp Ala Asn Gly Cys Asp Tyr Asn Pro Tyr Arg Met Gly
```

```
                    275                 280                 285
Asn Gln Asp Phe Tyr Gly Pro Gly Leu Thr Val Asp Thr Ser Lys Lys
    290                 295                 300
Phe Thr Val Val Ser Gln Phe Glu Glu Asn Lys Leu Thr Gln Phe Phe
305                 310                 315                 320
Val Gln Asp Gly Lys Lys Ile Glu Ile Pro Gly Pro Lys Val Glu Gly
                325                 330                 335
Ile Asp Ala Asp Ser Ala Ala Ile Thr Pro Glu Leu Cys Ser Ala Leu
            340                 345                 350
Phe Lys Ala Phe Asp Asp Arg Asp Arg Phe Ser Glu Val Gly Gly Phe
        355                 360                 365
Asp Ala Ile Asn Thr Ala Leu Ser Thr Pro Met Val Leu Val Met Ser
    370                 375                 380
Ile Trp Asp Asp His Tyr Ala Asn Met Leu Trp Leu Asp Ser Ser Tyr
385                 390                 395                 400
Pro Pro Glu Lys Ala Gly Gln Pro Gly Gly Asp Arg Gly Pro Cys Pro
                405                 410                 415
Gln Asp Ser Gly Val Pro Ala Asp Val Glu Ala Gln Tyr Pro Asn Ala
            420                 425                 430
Lys Val Ile Trp Ser Asn Ile Arg Phe Gly Pro Ile Gly Ser Thr Val
        435                 440                 445
Asn Val
    450

<210> SEQ ID NO 11
<211> LENGTH: 1800
<212> TYPE: DNA
<213> ORGANISM: Thielavia terrestris

<400> SEQUENCE: 11
aattgaagga gggagtggcg gagtggccac caagtcaggc ggctgtcaac taaccaagga      60
tgggaacagt tcggctcgcc ttgcccgagg gcagcgttcc ctgatgggga cgaaccatgg     120
gactggggtc agctgctgta taaaagttca aatcgatgat ctctcagatg gcgctgctgg     180
ggtgttctgc gcttttccat cctcgcaacc tggtatccca ctagtccagc gttcggcacc     240
atgaagtcgt tcaccattgc cgccttggca gccctatggg cccaggaggc cgccgcccac     300
gcgaccttcc aggacctctg gattgatgga tcgactacg gctcgcaatg tgtccgcctc     360
ccggcgtcca actcccccgt caccaatgtt gcgtccgacg atatccgatg caatgtcggc     420
acctcgaggc ccaccgtcaa gtgcccggtc aaggccggct ccacggtcac gatcgagatg     480
caccaggttc gcacgcctct ctgcgtaggc cccccagcta ctatatggca ctaacacgac     540
ctccagcaac ctggcgaccg gtcttgcgcc aacgaggcta tcggcggcga ccactacggc     600
cccgtaatgg tgtacatgtc caaggtcgat gacgcggtga cagccgacgg ttcatcgggc     660
tggttcaagg tgttccagga cagctgggcc aagaacccgt cgggttcgac gggcgacgac     720
gactactggg gcaccaagga cctcaactcg tgctgcggca agatgaacgt caagatcccc     780
gaagacatcg agccgggcga ctacctgctc cgcgccgagg ttatcgcgct gcacgtggcc     840
gccagctcgg gcggcgcgca gttctacatg tcctgctacc agctgaccgt gacgggctcc     900
ggcagcgcca ccccctcgac cgtgaatttc ccgggcgcct actcggccag cgacccgggc     960
atcctgatca acatccacgc gcccatgtcg acctacgtcg tcccgggccc gaccgtgtac    1020
gcgggcggct cgaccaagtc ggctggcagc tcctgctccg gctgcgaggc gacctgcacg    1080
```

```
gttggttccg gccccagcgc gacactgacg cagcccacct ccaccgcgac cgcgacctcc   1140
gcccctggcg gcggcggctc cggctgcacg gcggccaagt accagcagtg cggcggcacc   1200
ggctacactg ggtgcaccac ctgcgctgta agttccctcg tgatatgcag cggaacaccg   1260
tctggactgt tttgctaact cgcgtcgtag tccgggtcta cctgcagcgc cgtctcgcct   1320
ccgtactact cgcagtgcct ctaagccggg agcgcttgct cagcgggctg ctgtgaagga   1380
gctccatgtc cccatgccgc catggccgga gtacccgggct gagcgcccaa ttcttgtata   1440
tagttgagtt ttcccaatca tgaatacata tgcatctgca tggactgttg cgtcgtcagt   1500
ctacatcctt tgctccactg aactgtgaga ccccatgtca tccggaccat cgatcggtg    1560 ctcgctctac catctcggtt gatgggtctg ggcttgagag tcactggcac gtcctcggcg   1620
gtaatgaaat gtggaggaaa gtgtgagctg tctgacgcac tcggcgctga tgagacgttg   1680
agcgcggccc acactggtgt tctgtaagcc agcacacaaa agaatactcc aggatggccc   1740
atagcggcaa atatacagta tcagggatgc aaaaagtgca aaagtaaggg gctcaatcgg   1800
```

<210> SEQ ID NO 12
<211> LENGTH: 326
<212> TYPE: PRT
<213> ORGANISM: Thielavia terrestris

<400> SEQUENCE: 12

```
Met Lys Ser Phe Thr Ile Ala Ala Leu Ala Ala Leu Trp Ala Gln Glu
1               5                   10                  15

Ala Ala Ala His Ala Thr Phe Gln Asp Leu Trp Ile Asp Gly Val Asp
            20                  25                  30

Tyr Gly Ser Gln Cys Val Arg Leu Pro Ala Ser Asn Ser Pro Val Thr
        35                  40                  45

Asn Val Ala Ser Asp Asp Ile Arg Cys Asn Val Gly Thr Ser Arg Pro
    50                  55                  60

Thr Val Lys Cys Pro Val Lys Ala Gly Ser Thr Val Thr Ile Glu Met
65                  70                  75                  80

His Gln Gln Pro Gly Asp Arg Ser Cys Ala Asn Glu Ala Ile Gly Gly
                85                  90                  95

Asp His Tyr Gly Pro Val Met Val Tyr Met Ser Lys Val Asp Asp Ala
            100                 105                 110

Val Thr Ala Asp Gly Ser Ser Gly Trp Phe Lys Val Phe Gln Asp Ser
        115                 120                 125

Trp Ala Lys Asn Pro Ser Gly Ser Thr Gly Asp Asp Tyr Trp Gly
    130                 135                 140

Thr Lys Asp Leu Asn Ser Cys Cys Gly Lys Met Asn Val Lys Ile Pro
145                 150                 155                 160

Glu Asp Ile Glu Pro Gly Asp Tyr Leu Leu Arg Ala Glu Val Ile Ala
                165                 170                 175

Leu His Val Ala Ala Ser Ser Gly Gly Ala Gln Phe Tyr Met Ser Cys
            180                 185                 190

Tyr Gln Leu Thr Val Thr Gly Ser Gly Ser Ala Thr Pro Ser Thr Val
        195                 200                 205

Asn Phe Pro Gly Ala Tyr Ser Ala Ser Asp Pro Gly Ile Leu Ile Asn
    210                 215                 220

Ile His Ala Pro Met Ser Thr Tyr Val Val Pro Gly Pro Thr Val Tyr
225                 230                 235                 240

Ala Gly Gly Ser Thr Lys Ser Ala Gly Ser Ser Cys Ser Gly Cys Glu
                245                 250                 255
```

-continued

```
Ala Thr Cys Thr Val Gly Ser Gly Pro Ser Ala Thr Leu Thr Gln Pro
            260                 265                 270

Thr Ser Thr Ala Thr Ala Thr Ser Ala Pro Gly Gly Gly Ser Gly
        275                 280                 285

Cys Thr Ala Ala Lys Tyr Gln Gln Cys Gly Gly Thr Gly Tyr Thr Gly
            290                 295                 300

Cys Thr Thr Cys Ala Ser Gly Ser Thr Cys Ser Ala Val Ser Pro Pro
305                 310                 315                 320

Tyr Tyr Ser Gln Cys Leu
                325

<210> SEQ ID NO 13
<211> LENGTH: 880
<212> TYPE: DNA
<213> ORGANISM: Thielavia terrestris

<400> SEQUENCE: 13
accccgggat cactgcccct aggaaccagc acacctcggt ccaatcatgc ggttcgacgc      60
cctctccgcc ctcgctcttg cgccgcttgt ggctggccac ggcgccgtga ccagctacat     120
catcggcggc aaaacctatc ccggctacga gggcttctcg cctgcctcga gcccgccgac     180
gatccagtac cagtggcccg actacaaccc gaccctgagc gtgaccgacc cgaagatgcg     240
ctgcaacggc ggcacctcgg cagagctcag cgcgcccgtc caggccggcg agaacgtgac     300
ggccgtctgg aagcagtgga cccaccagca aggccccgtc atggtctgga tgttcaagtg     360
ccccggcgac ttctcgtcgt gccacggcga cggcaagggc tggttcaaga tcgaccagct     420
gggcctgtgg ggcaacaacc tcaactcgaa caactggggc accgcgatcg tctacaagac     480
cctccagtgg agcaacccga tccccaagaa cctcgcgccg gcaactacc tcatccgcca     540 cgagctgctc gccctgcacc aggccaacac gccgcagttc tacgccgagt gcgcccagct     600
ggtcgtctcc ggcagcggct ccgccctgcc ccgtccgac tacctctaca gcatccccgt     660
ctacgcgccc cagaacgacc ccggcatcac cgtgagtggg cttccgttcc gcggcgagct     720
ctgtggaaat cttgctgacg atgggctagg ttgacatcta caacggcggg cttacctcct     780
acaccccgcc cggcggcccc gtctggtctg gcttcgagtt ttaggcgcat tgagtcgggg     840
gctacgaggg gaaggcatct gttcgcatga gcgtgggtac                          880

<210> SEQ ID NO 14
<211> LENGTH: 478
<212> TYPE: PRT
<213> ORGANISM: Theilavia terrestris

<400> SEQUENCE: 14

Met Arg Phe Asp Ala Leu Ser Ala Leu Ala Leu Ala Pro Leu Val Ala
1               5                   10                  15

Gly His Gly Ala Val Thr Ser Tyr Ile Ile Gly Gly Lys Thr Tyr Pro
            20                  25                  30

Gly Tyr Glu Gly Phe Ser Pro Ala Ser Ser Pro Pro Thr Ile Gln Tyr
        35                  40                  45

Gln Trp Pro Asp Tyr Asn Pro Thr Leu Ser Val Thr Asp Pro Lys Met
    50                  55                  60

Arg Cys Asn Gly Gly Thr Ser Ala Glu Leu Ser Ala Pro Val Gln Ala
65                  70                  75                  80

Gly Glu Asn Val Thr Ala Val Trp Lys Gln Trp Thr His Gln Gln Gly
                85                  90                  95
```

-continued

Pro Val Met Val Trp Met Phe Lys Cys Pro Gly Asp Phe Ser Ser Ser
            100                 105                 110

His Gly Asp Gly Lys Gly Trp Phe Lys Ile Asp Gln Leu Gly Leu Trp
        115                 120                 125

Gly Asn Asn Leu Asn Ser Asn Asn Trp Gly Thr Ala Ile Val Tyr Lys
130                 135                 140

Thr Leu Gln Trp Ser Asn Pro Ile Pro Lys Asn Leu Ala Pro Gly Asn
145                 150                 155                 160

Tyr Leu Ile Arg His Glu Leu Leu Ala Leu His Gln Ala Asn Thr Pro
                165                 170                 175

Gln Phe Tyr Ala Glu Cys Ala Gln Leu Val Val Ser Gly Ser Gly Ser
            180                 185                 190

Ala Leu Pro Pro Ser Asp Tyr Leu Tyr Ser Ile Pro Val Tyr Ala Pro
        195                 200                 205

Gln Asn Asp Pro Gly Ile Thr Val Asp Ile Tyr Asn Gly Gly Leu Thr
210                 215                 220

Ser Tyr Thr Pro Pro Gly Gly Pro Val Trp Ser Gly Phe Glu Phe Met
225                 230                 235                 240

Arg Phe Asp Ala Leu Ser Ala Leu Ala Leu Ala Pro Leu Val Ala Gly
                245                 250                 255

His Gly Ala Val Thr Ser Tyr Ile Ile Gly Gly Lys Thr Tyr Pro Gly
            260                 265                 270

Tyr Glu Gly Phe Ser Pro Ala Ser Ser Pro Thr Ile Gln Tyr Gln
        275                 280                 285

Trp Pro Asp Tyr Asn Pro Thr Leu Ser Val Thr Asp Pro Lys Met Arg
290                 295                 300

Cys Asn Gly Gly Thr Ser Ala Glu Leu Ser Ala Pro Val Gln Ala Gly
305                 310                 315                 320

Glu Asn Val Thr Ala Val Trp Lys Gln Trp Thr His Gln Gln Gly Pro
                325                 330                 335

Val Met Val Trp Met Phe Lys Cys Pro Gly Asp Phe Ser Ser Ser His
            340                 345                 350

Gly Asp Gly Lys Gly Trp Phe Lys Ile Asp Gln Leu Gly Leu Trp Gly
        355                 360                 365

Asn Asn Leu Asn Ser Asn Asn Trp Gly Thr Ala Ile Val Tyr Lys Thr
370                 375                 380

Leu Gln Trp Ser Asn Pro Ile Pro Lys Asn Leu Ala Pro Gly Asn Tyr
385                 390                 395                 400

Leu Ile Arg His Glu Leu Leu Ala Leu His Gln Ala Asn Thr Pro Gln
                405                 410                 415

Phe Tyr Ala Glu Cys Ala Gln Leu Val Val Ser Gly Ser Gly Ser Ala
            420                 425                 430

Leu Pro Pro Ser Asp Tyr Leu Tyr Ser Ile Pro Val Tyr Ala Pro Gln
        435                 440                 445

Asn Asp Pro Gly Ile Thr Val Asp Ile Tyr Asn Gly Gly Leu Thr Ser
450                 455                 460

Tyr Thr Pro Pro Gly Gly Pro Val Trp Ser Gly Phe Glu Phe
465                 470                 475

<210> SEQ ID NO 15
<211> LENGTH: 1000
<212> TYPE: DNA
<213> ORGANISM: Thielavia terrestris

<400> SEQUENCE: 15

```
ctcctgttcc tgggccaccg cttgttgcct gcactattgg tagagttggt ctattgctag      60
agttggccat gcttctcaca tcagtcctcg gctcggctgc cctgcttgct agcggcgctg     120
cggcacacgg cgccgtgacc agctacatca tcgccggcaa gaattacccg ggtgggtag      180
ctgattattg agggcgcatt caaggttcat accggtgtgc atggctgaca accggctggc     240
agataccaag gctttctcc tgcgaactcg ccgaacgtca tccaatggca atggcatgac     300
tacaaccccg tcttgtcgtg cagcgactcg aagcttcgct gcaacggcgg cacgtcggcc     360
accctgaacg ccacggccgc accgggcgac accatcaccg ccatctgggc gcagtggacg     420
cacagccagg gccccatcct ggtgtggatg tacaagtgcc cgggctcctt cagctcctgt     480
gacggctccg gcgctggctg gttcaagatc gacgaggccg gcttccacgg cgacggcgtc     540
aaggtcttcc tcgacaccga gaacccgtcc ggctgggaca tcgccaagct cgtcggcggc     600
aacaagcagt ggagcagcaa ggtccccgag ggcctcgccc ccggcaacta cctcgtccgc     660
cacgagttga tcgccctgca ccaggccaac aacccgcagt tctacccgga gtgcgcccag     720
gtcgtcatca ccggctccgg caccgcgcag ccggatgcct catacaaggc ggctatcccc     780
ggctactgca accagaatga cccgaacatc aaggtgagat ccaggcgtaa tgcagtctac     840
tgctggaaag aaagtggtcc aagctaaacc gcgctccagg tgcccatcaa cgaccactcc     900
atccctcaga cctacaagat tcccggcccct cccgtcttca agggcaccgc cagcaagaag     960
gcccgggact tcaccgcctg aagttgttga atcgatggag                          1000
```

<210> SEQ ID NO 16
<211> LENGTH: 516
<212> TYPE: PRT
<213> ORGANISM: Thielavia terrestris

<400> SEQUENCE: 16

```
Met Leu Leu Thr Ser Val Leu Gly Ser Ala Ala Leu Ala Ser Gly
1               5                   10                  15

Ala Ala Ala His Gly Ala Val Thr Ser Tyr Ile Ile Ala Gly Lys Asn
            20                  25                  30

Tyr Pro Gly Tyr Gln Gly Phe Ser Pro Ala Asn Ser Pro Asn Val Ile
        35                  40                  45

Gln Trp Gln Trp His Asp Tyr Asn Pro Val Leu Ser Cys Ser Asp Ser
    50                  55                  60

Lys Leu Arg Cys Asn Gly Gly Thr Ser Ala Thr Leu Asn Ala Thr Ala
65                  70                  75                  80

Ala Pro Gly Asp Thr Ile Thr Ala Ile Trp Ala Gln Trp Thr His Ser
                85                  90                  95

Gln Gly Pro Ile Leu Val Trp Met Tyr Lys Cys Pro Gly Ser Phe Ser
            100                 105                 110

Ser Cys Asp Gly Ser Gly Ala Gly Trp Phe Lys Ile Asp Glu Ala Gly
        115                 120                 125

Phe His Gly Asp Gly Val Lys Val Phe Leu Asp Thr Glu Asn Pro Ser
    130                 135                 140

Gly Trp Asp Ile Ala Lys Leu Val Gly Gly Asn Lys Gln Trp Ser Ser
145                 150                 155                 160

Lys Val Pro Glu Gly Leu Ala Pro Gly Asn Tyr Leu Val Arg His Glu
                165                 170                 175

Leu Ile Ala Leu His Gln Ala Asn Asn Pro Gln Phe Tyr Pro Glu Cys
            180                 185                 190
```

Ala Gln Val Val Ile Thr Gly Ser Gly Thr Ala Gln Pro Asp Ala Ser
        195                 200                 205

Tyr Lys Ala Ala Ile Pro Gly Tyr Cys Asn Gln Asn Asp Pro Asn Ile
    210                 215                 220

Lys Val Pro Ile Asn Asp His Ser Ile Pro Gln Thr Tyr Lys Ile Pro
225                 230                 235                 240

Gly Pro Pro Val Phe Lys Gly Thr Ala Ser Lys Lys Ala Arg Asp Phe
            245                 250                 255

Thr Ala Met Leu Leu Thr Ser Val Leu Gly Ser Ala Ala Leu Leu Ala
                260                 265                 270

Ser Gly Ala Ala Ala His Gly Ala Val Thr Ser Tyr Ile Ile Ala Gly
            275                 280                 285

Lys Asn Tyr Pro Gly Tyr Gln Gly Phe Ser Pro Ala Asn Ser Pro Asn
        290                 295                 300

Val Ile Gln Trp Gln Trp His Asp Tyr Asn Pro Val Leu Ser Cys Ser
305                 310                 315                 320

Asp Ser Lys Leu Arg Cys Asn Gly Gly Thr Ser Ala Thr Leu Asn Ala
            325                 330                 335

Thr Ala Ala Pro Gly Asp Thr Ile Thr Ala Ile Trp Ala Gln Trp Thr
                340                 345                 350

His Ser Gln Gly Pro Ile Leu Val Trp Met Tyr Lys Cys Pro Gly Ser
            355                 360                 365

Phe Ser Ser Cys Asp Gly Ser Gly Ala Gly Trp Phe Lys Ile Asp Glu
        370                 375                 380

Ala Gly Phe His Gly Asp Gly Val Lys Val Phe Leu Asp Thr Glu Asn
385                 390                 395                 400

Pro Ser Gly Trp Asp Ile Ala Lys Leu Val Gly Gly Asn Lys Gln Trp
            405                 410                 415

Ser Ser Lys Val Pro Glu Gly Leu Ala Pro Gly Asn Tyr Leu Val Arg
                420                 425                 430

His Glu Leu Ile Ala Leu His Gln Ala Asn Asn Pro Gln Phe Tyr Pro
            435                 440                 445

Glu Cys Ala Gln Val Val Ile Thr Gly Ser Gly Thr Ala Gln Pro Asp
        450                 455                 460

Ala Ser Tyr Lys Ala Ala Ile Pro Gly Tyr Cys Asn Gln Asn Asp Pro
465                 470                 475                 480

Asn Ile Lys Val Pro Ile Asn Asp His Ser Ile Pro Gln Thr Tyr Lys
            485                 490                 495

Ile Pro Gly Pro Pro Val Phe Lys Gly Thr Ala Ser Lys Lys Ala Arg
                500                 505                 510

Asp Phe Thr Ala
        515

<210> SEQ ID NO 17
<211> LENGTH: 681
<212> TYPE: DNA
<213> ORGANISM: Thielavia terrestris

<400> SEQUENCE: 17
atgctcgcaa acggtgccat cgtcttcctg ccgccgcccc tcggcgtcag tggccactac    60
acctggccac gggttaacga cggcgccgac tggcaacagg tccgtaaggc ggacaactgg   120
caggacaacg gctacgtcgg ggatgtcacg tcgccacaga tccgctgttt ccaggcgacc   180
ccgtccccgg ccccatccgt cctcaacacc acggccggct cgaccgtgac ctactgggcc   240

```
aaccccgacg tctaccaccc cgggcctgtg cagttttaca tggcccgcgt gcccgatggc    300
gaggacatca actcgtggaa cggcgacggc gccgtgtggt tcaaggtgta cgaggaccat    360
cctacctttg gcgctcagct cacatggccc agcacgggca agagctcgtt cgcggttccc    420
atccccccgt gcatcaagtc cggctactac ctcctccggg cggagcaaat cggcctgcac    480
gtcgcccaga gcgtaggcgg agcgcagttc tacatctcat gcgcccagct cagcgtcacc    540
ggcggcggca gcaccgagcc gccgaacaag gtggccttcc ccggcgctta cagtgcgacg    600
gacccgggca ttctgatcaa catctactac cctgttccca cgtcctacca gaaccccggc    660
ccggccgtct tcagctgctg a                                             681
```

```
<210> SEQ ID NO 18
<211> LENGTH: 452
<212> TYPE: PRT
<213> ORGANISM: Thielavia terrestris

<400> SEQUENCE: 18

Met Leu Ala Asn Gly Ala Ile Val Phe Leu Ala Ala Leu Gly Val
1               5                   10                  15

Ser Gly His Tyr Thr Trp Pro Arg Val Asn Asp Gly Ala Asp Trp Gln
                20                  25                  30

Gln Val Arg Lys Ala Asp Asn Trp Gln Asp Asn Gly Tyr Val Gly Asp
            35                  40                  45

Val Thr Ser Pro Gln Ile Arg Cys Phe Gln Ala Thr Pro Ser Pro Ala
        50                  55                  60

Pro Ser Val Leu Asn Thr Thr Ala Gly Ser Thr Val Thr Tyr Trp Ala
65                  70                  75                  80

Asn Pro Asp Val Tyr His Pro Gly Pro Val Gln Phe Tyr Met Ala Arg
                85                  90                  95

Val Pro Asp Gly Glu Asp Ile Asn Ser Trp Asn Gly Asp Gly Ala Val
            100                 105                 110

Trp Phe Lys Val Tyr Glu Asp His Pro Thr Phe Gly Ala Gln Leu Thr
        115                 120                 125

Trp Pro Ser Thr Gly Lys Ser Ser Phe Ala Val Pro Ile Pro Pro Cys
130                 135                 140

Ile Lys Ser Gly Tyr Tyr Leu Leu Arg Ala Glu Gln Ile Gly Leu His
145                 150                 155                 160

Val Ala Gln Ser Val Gly Gly Ala Gln Phe Tyr Ile Ser Cys Ala Gln
                165                 170                 175

Leu Ser Val Thr Gly Gly Ser Thr Glu Pro Pro Asn Lys Val Ala
            180                 185                 190

Phe Pro Gly Ala Tyr Ser Ala Thr Asp Pro Gly Ile Leu Ile Asn Ile
        195                 200                 205

Tyr Tyr Pro Val Pro Thr Ser Tyr Gln Asn Pro Gly Pro Ala Val Phe
        210                 215                 220

Ser Cys Met Leu Ala Asn Gly Ala Ile Val Phe Leu Ala Ala Ala Leu
225                 230                 235                 240

Gly Val Ser Gly His Tyr Thr Trp Pro Arg Val Asn Asp Gly Ala Asp
                245                 250                 255

Trp Gln Gln Val Arg Lys Ala Asp Asn Trp Gln Asp Asn Gly Tyr Val
            260                 265                 270

Gly Asp Val Thr Ser Pro Gln Ile Arg Cys Phe Gln Ala Thr Pro Ser
        275                 280                 285
```

-continued

```
Pro Ala Pro Ser Val Leu Asn Thr Thr Ala Gly Ser Thr Val Thr Tyr
    290                 295                 300

Trp Ala Asn Pro Asp Val Tyr His Pro Gly Pro Val Gln Phe Tyr Met
305                 310                 315                 320

Ala Arg Val Pro Asp Gly Glu Asp Ile Asn Ser Trp Asn Gly Asp Gly
                325                 330                 335

Ala Val Trp Phe Lys Val Tyr Glu Asp His Pro Thr Phe Gly Ala Gln
            340                 345                 350

Leu Thr Trp Pro Ser Thr Gly Lys Ser Ser Phe Ala Val Pro Ile Pro
        355                 360                 365

Pro Cys Ile Lys Ser Gly Tyr Tyr Leu Leu Arg Ala Glu Gln Ile Gly
    370                 375                 380

Leu His Val Ala Gln Ser Val Gly Gly Ala Gln Phe Tyr Ile Ser Cys
385                 390                 395                 400

Ala Gln Leu Ser Val Thr Gly Gly Ser Thr Glu Pro Pro Asn Lys
                405                 410                 415

Val Ala Phe Pro Gly Ala Tyr Ser Ala Thr Asp Pro Gly Ile Leu Ile
            420                 425                 430

Asn Ile Tyr Tyr Pro Val Pro Thr Ser Tyr Gln Asn Pro Gly Pro Ala
        435                 440                 445

Val Phe Ser Cys
    450

<210> SEQ ID NO 19
<211> LENGTH: 960
<212> TYPE: DNA
<213> ORGANISM: Thielavia terrestris

<400> SEQUENCE: 19 atgaaggggac ttttcagtgc cgccgccctc tccctggccg tcggccaggc ttcggcccat      60
tacatcttcc agcaactctc catcaacggg aaccagtttc cggtgtacca atatattcgc     120
aagaacacca attataacag tcccgttacc gatctcacgt ccgacgatct tcggtgcaat     180
gtcggcgccc agggtgctgg acagacacc gtcacggtga aggccggcga ccagttcacc     240
ttcacccttg acaccctgt ttaccaccag gggcccatct ccatctacat gtccaaggcc     300
ccgggcgcgg cgtcagacta cgatggcagc ggcggctggt tcaagatcaa ggactgggc     360 ccgactttca cgccgacgg cacggccacc tgggacatgg ccggctcata cacctacaac     420
atcccgacct gcattcccga cggcgactat ctgctccgca tccagtcgct ggccatccac     480 aaccccctggc cggcgggcat cccgcagttc tacatctcct cgcccagat caccgtgacc     540 ggcggcggca acggcaaccc tggcccgacg ccctcatcc ccggcgcctt caaggacacc     600
gacccgggct acacggtgaa catctacacg aacttccaca actacacggt tcccggcccg     660
gaggtcttca gctgcaacgg cggcggctcg aacccgcccc gccggtgag tagcagcacg     720 cccgcgacca cgacgctggt cacgtcgacg cgcaccacgt cctccacgtc ctccgcctcg     780
acgccggcct cgaccggcgg ctgcaccgtc gccaagtggg gccagtgcgg cggcaacggg     840
tacaccggct gcacgacctg cgcggccggg tccacctgca gcaagcagaa cgactactac     900
tcgcagtgct tgtaaggggag gccgcaaagc atgaggtgtt tgaagaggag gagaggggtc     960

<210> SEQ ID NO 20
<211> LENGTH: 608
<212> TYPE: PRT
<213> ORGANISM: Thielavia terrestris
```

```
<400> SEQUENCE: 20

Met Lys Gly Leu Phe Ser Ala Ala Ala Leu Ser Leu Ala Val Gly Gln
1               5                   10                  15

Ala Ser Ala His Tyr Ile Phe Gln Gln Leu Ser Ile Asn Gly Asn Gln
            20                  25                  30

Phe Pro Val Tyr Gln Tyr Ile Arg Lys Asn Thr Asn Tyr Asn Ser Pro
        35                  40                  45

Val Thr Asp Leu Thr Ser Asp Asp Leu Arg Cys Asn Val Gly Ala Gln
    50                  55                  60

Gly Ala Gly Thr Asp Thr Val Thr Val Lys Ala Gly Asp Gln Phe Thr
65              70                  75                  80

Phe Thr Leu Asp Thr Pro Val Tyr His Gln Gly Pro Ile Ser Ile Tyr
                85                  90                  95

Met Ser Lys Ala Pro Gly Ala Ala Ser Asp Tyr Asp Gly Ser Gly Gly
            100                 105                 110

Trp Phe Lys Ile Lys Asp Trp Gly Pro Thr Phe Asn Ala Asp Gly Thr
        115                 120                 125

Ala Thr Trp Asp Met Ala Gly Ser Tyr Thr Tyr Asn Ile Pro Thr Cys
    130                 135                 140

Ile Pro Asp Gly Asp Tyr Leu Leu Arg Ile Gln Ser Leu Ala Ile His
145                 150                 155                 160

Asn Pro Trp Pro Ala Gly Ile Pro Gln Phe Tyr Ile Ser Cys Ala Gln
                165                 170                 175

Ile Thr Val Thr Gly Gly Gly Asn Gly Asn Pro Gly Pro Thr Ala Leu
            180                 185                 190

Ile Pro Gly Ala Phe Lys Asp Thr Asp Pro Gly Tyr Thr Val Asn Ile
        195                 200                 205

Tyr Thr Asn Phe His Asn Tyr Thr Val Pro Gly Pro Glu Val Phe Ser
    210                 215                 220

Cys Asn Gly Gly Ser Asn Pro Pro Pro Val Ser Ser Ser Thr
225                 230                 235                 240

Pro Ala Thr Thr Thr Leu Val Thr Ser Thr Arg Thr Thr Ser Ser Thr
                245                 250                 255

Ser Ser Ala Ser Thr Pro Ala Ser Thr Gly Gly Cys Thr Val Ala Lys
            260                 265                 270

Trp Gly Gln Cys Gly Gly Asn Gly Tyr Thr Gly Cys Thr Thr Cys Ala
        275                 280                 285

Ala Gly Ser Thr Cys Ser Lys Gln Asn Asp Tyr Tyr Ser Gln Cys Leu
    290                 295                 300

Met Lys Gly Leu Phe Ser Ala Ala Ala Leu Ser Leu Ala Val Gly Gln
305                 310                 315                 320

Ala Ser Ala His Tyr Ile Phe Gln Gln Leu Ser Ile Asn Gly Asn Gln
                325                 330                 335

Phe Pro Val Tyr Gln Tyr Ile Arg Lys Asn Thr Asn Tyr Asn Ser Pro
            340                 345                 350

Val Thr Asp Leu Thr Ser Asp Asp Leu Arg Cys Asn Val Gly Ala Gln
        355                 360                 365

Gly Ala Gly Thr Asp Thr Val Thr Val Lys Ala Gly Asp Gln Phe Thr
    370                 375                 380

Phe Thr Leu Asp Thr Pro Val Tyr His Gln Gly Pro Ile Ser Ile Tyr
385                 390                 395                 400

Met Ser Lys Ala Pro Gly Ala Ala Ser Asp Tyr Asp Gly Ser Gly Gly
                405                 410                 415
```

Trp Phe Lys Ile Lys Asp Trp Gly Pro Thr Phe Asn Ala Asp Gly Thr
        420                 425                 430

Ala Thr Trp Asp Met Ala Gly Ser Tyr Thr Tyr Asn Ile Pro Thr Cys
        435                 440                 445

Ile Pro Asp Gly Asp Tyr Leu Leu Arg Ile Gln Ser Leu Ala Ile His
450                 455                 460

Asn Pro Trp Pro Ala Gly Ile Pro Gln Phe Tyr Ile Ser Cys Ala Gln
465                 470                 475                 480

Ile Thr Val Thr Gly Gly Asn Gly Asn Pro Gly Pro Thr Ala Leu
            485                 490                 495

Ile Pro Gly Ala Phe Lys Asp Thr Asp Pro Gly Tyr Thr Val Asn Ile
            500                 505                 510

Tyr Thr Asn Phe His Asn Tyr Thr Val Pro Gly Pro Glu Val Phe Ser
            515                 520                 525

Cys Asn Gly Gly Ser Asn Pro Pro Pro Val Ser Ser Ser Thr
            530                 535                 540

Pro Ala Thr Thr Thr Leu Val Thr Ser Thr Arg Thr Thr Ser Ser Thr
545                 550                 555                 560

Ser Ser Ala Ser Thr Pro Ala Ser Thr Gly Gly Cys Thr Val Ala Lys
            565                 570                 575

Trp Gly Gln Cys Gly Gly Asn Gly Tyr Thr Gly Cys Thr Thr Cys Ala
            580                 585                 590

Ala Gly Ser Thr Cys Ser Lys Gln Asn Asp Tyr Tyr Ser Gln Cys Leu
            595                 600                 605

<210> SEQ ID NO 21
<211> LENGTH: 799
<212> TYPE: DNA
<213> ORGANISM: Thermoascus aurantiacus

<400> SEQUENCE: 21

```
atgtcctttt ccaagataat tgctactgcc ggcgttcttg cctctgcttc tctagtggct      60
ggccatggct tcgttcagaa catcgtgatt gatggtaaaa agtatgtcat tgcaagacgc     120
acataagcgg caacagctga caatcgacag ttatggcggg tatctagtga accagtatcc     180
atacatgtcc aatcctccag aggtcatcgc ctggtctact acggcaactg atcttggatt     240
tgtggacggt actggatacc aaaccccaga tatcatctgc cataggggcg ccaagcctgg     300
agccctgact gctccagtct ctccaggagg aactgttgag cttcaatgga ctccatggcc     360
tgattctcac catggcccag ttatcaacta ccttgctccg tgcaatggtg attgttccac     420
tgtggataag acccaattag aattcttcaa aattgccgag agcggtctca tcaatgatga     480
caatcctcct gggatctggg cttcagacaa tctgatagca gccaacaaca gctggactgt     540
caccattcca accacaattg cacctggaaa ctatgttctg aggcatgaga ttattgctct     600
tcactcagct cagaaccagg atggtgccca gaactatccc cagtgcatca atctgcaggt     660
cactggaggt ggttctgata cccctgctgg aactcttgga acggcactct accacgatac     720
cgatcctgga attctgatca acatctatca gaaactttcc agctatatca tccctggtcc     780
tcctctgtat actggttaa                                                  799
```

<210> SEQ ID NO 22
<211> LENGTH: 250
<212> TYPE: PRT
<213> ORGANISM: Thermoascus aurantiacus

<400> SEQUENCE: 22

```
Met Ser Phe Ser Lys Ile Ile Ala Thr Ala Gly Val Leu Ala Ser Ala
1               5                   10                  15
Ser Leu Val Ala Gly His Gly Phe Val Gln Asn Ile Val Ile Asp Gly
            20                  25                  30
Lys Lys Tyr Tyr Gly Gly Tyr Leu Val Asn Gln Tyr Pro Tyr Met Ser
        35                  40                  45
Asn Pro Pro Glu Val Ile Ala Trp Ser Thr Thr Ala Thr Asp Leu Gly
    50                  55                  60
Phe Val Asp Gly Thr Gly Tyr Gln Thr Pro Asp Ile Ile Cys His Arg
65                  70                  75                  80
Gly Ala Lys Pro Gly Ala Leu Thr Ala Pro Val Ser Pro Gly Gly Thr
                85                  90                  95
Val Glu Leu Gln Trp Thr Pro Trp Pro Asp Ser His Gly Pro Val
            100                 105                 110
Ile Asn Tyr Leu Ala Pro Cys Asn Gly Asp Cys Ser Thr Val Asp Lys
        115                 120                 125
Thr Gln Leu Glu Phe Phe Lys Ile Ala Glu Ser Gly Leu Ile Asn Asp
    130                 135                 140
Asp Asn Pro Pro Gly Ile Trp Ala Ser Asp Asn Leu Ile Ala Ala Asn
145                 150                 155                 160
Asn Ser Trp Thr Val Thr Ile Pro Thr Thr Ile Ala Pro Gly Asn Tyr
                165                 170                 175
Val Leu Arg His Glu Ile Ile Ala Leu His Ser Ala Gln Asn Gln Asp
            180                 185                 190
Gly Ala Gln Asn Tyr Pro Gln Cys Ile Asn Leu Gln Val Thr Gly Gly
        195                 200                 205
Gly Ser Asp Asn Pro Ala Gly Thr Leu Gly Thr Ala Leu Tyr His Asp
    210                 215                 220
Thr Asp Pro Gly Ile Leu Ile Asn Ile Tyr Gln Lys Leu Ser Ser Tyr
225                 230                 235                 240
Ile Ile Pro Gly Pro Pro Leu Tyr Thr Gly
                245                 250
```

<210> SEQ ID NO 23
<211> LENGTH: 1172
<212> TYPE: DNA
<213> ORGANISM: Trichoderma reesei

<400> SEQUENCE: 23

```
ggatctaagc cccatcgata tgaagtcctg cgccattctt gcagcccttg gctgtcttgc      60
cgggagcgtt ctcggccatg gacaagtcca aaacttcacg atcaatggac aatacaatca    120
gggtttcatt ctcgattact actatcagaa gcagaatact ggtcacttcc ccaacgttgc    180
tggctggtac gccgaggacc tagacctggg cttcatctcc cctgaccaat acaccacgcc    240
cgacattgtc tgtcacaaga acgcggcccc aggtgccatt tctgccactg cagcggccgg    300
cagcaacatc gtcttccaat ggggccctgg cgtctggcct cacccctacg gtcccatcgt    360
tacctacgtg gctgagtgca gcggatcgtg cacgaccgtg aacaagaaca acctgcgctg    420
ggtcaagatt caggaggccg gcatcaacta aacacccaa gtctgggcgc agcaggatct    480
gatcaaccag gcaacaagt ggactgtgaa gatcccgtcg agcctcaggc ccggaaacta    540
tgtcttccgc catgaacttc ttgctgccca tggtgcctct agtgcgaacg gcatgcagaa    600
ctatcctcag tgcgtgaaca tcgccgtcac aggctcgggc acgaaagcgc tccctgccgg    660
```

```
aactcctgca actcagctct acaagcccac tgaccctggc atcttgttca acccttacac    720
aacaatcacg agctacacca tccctggccc agccctgtgg caaggctaga tccagggta    780 cggtgttggc gttcgtgaag tcggagctgt tgacaaggat atctgatgat gaacggagag    840
gactgatggg cgtgactgag tgtatatatt tttgatgacc aaattgtata cgaaatccga    900
acgcatggtg atcattgttt atccctgtag tatattgtct ccaggctgct aagagcccac    960
cgggtgtatt acggcaacaa agtcaggaat ttgggtggca atgaacgcag gtctccatga   1020
atgtatatgt gaagaggcat cggctggcat gggcattacc agatataggc cctgtgaaac   1080
atatagtact tgaacgtgct actggaacgg atcataagca agtcatcaac atgtgaaaaa   1140
acactacatg taaaaaaaaa aaaaaaaaaa aa                                 1172
```

<210> SEQ ID NO 24
<211> LENGTH: 249
<212> TYPE: PRT
<213> ORGANISM: Trichoderma reesei

<400> SEQUENCE: 24

```
Met Lys Ser Cys Ala Ile Leu Ala Ala Leu Gly Cys Leu Ala Gly Ser
1               5                   10                  15

Val Leu Gly His Gly Gln Val Gln Asn Phe Thr Ile Asn Gly Gln Tyr
            20                  25                  30

Asn Gln Gly Phe Ile Leu Asp Tyr Tyr Gln Lys Gln Asn Thr Gly
        35                  40                  45

His Phe Pro Asn Val Ala Gly Trp Tyr Ala Glu Asp Leu Asp Leu Gly
    50                  55                  60

Phe Ile Ser Pro Asp Gln Tyr Thr Thr Pro Asp Ile Val Cys His Lys
65                  70                  75                  80

Asn Ala Ala Pro Gly Ala Ile Ser Ala Thr Ala Ala Gly Ser Asn
                85                  90                  95

Ile Val Phe Gln Trp Gly Pro Gly Val Trp Pro His Pro Tyr Gly Pro
            100                 105                 110

Ile Val Thr Tyr Val Val Glu Cys Ser Gly Ser Cys Thr Thr Val Asn
        115                 120                 125

Lys Asn Asn Leu Arg Trp Val Lys Ile Gln Glu Ala Gly Ile Asn Tyr
    130                 135                 140

Asn Thr Gln Val Trp Ala Gln Gln Asp Leu Ile Asn Gln Gly Asn Lys
145                 150                 155                 160

Trp Thr Val Lys Ile Pro Ser Ser Leu Arg Pro Gly Asn Tyr Val Phe
                165                 170                 175

Arg His Glu Leu Leu Ala Ala His Gly Ala Ser Ser Ala Asn Gly Met
            180                 185                 190

Gln Asn Tyr Pro Gln Cys Val Asn Ile Ala Val Thr Gly Ser Gly Thr
        195                 200                 205

Lys Ala Leu Pro Ala Gly Thr Pro Ala Thr Gln Leu Tyr Lys Pro Thr
    210                 215                 220

Asp Pro Gly Ile Leu Phe Asn Pro Tyr Thr Thr Ile Thr Ser Tyr Thr
225                 230                 235                 240

Ile Pro Gly Pro Ala Leu Trp Gln Gly
                245
```

<210> SEQ ID NO 25
<211> LENGTH: 2771
<212> TYPE: DNA

<213> ORGANISM: Aspergillus oryzae

<400> SEQUENCE: 25

```
ctgttctgct ggttacctgc cacgttatca tgaagcttgg ttggatcgag gtggccgcat      60
tggcggctgc ctcagtagtc agtgccaagg atgatctcgc gtactcccct cctttctacc     120
cttccccatg ggcagatggt cagggtgaat gggcggaagt atacaaacgc gctgtagaca     180
tagtttccca gatgacgttg acagagaaag tcaacttaac gactggaaca ggatggcaac     240
tagagaggtg tgttggacaa actggcagtg ttcccagact caacatcccc agcttgtgtt     300
tgcaggatag tcctcttggt attcgtttct cggactacaa ttcagctttc cctgcgggtg     360
ttaatgtcgc tgccacctgg gacaagacgc tcgcctacct tcgtggtcag gcaatgggtg     420
aggagttcag tgataagggt attgacgttc agctgggtcc tgctgctggc cctctcggtg     480
ctcatccgga tggcggtaga aactgggaag gtttctcacc agatccagcc ctcaccggtg     540
tacttttttgc ggagacgatt aagggtattc aagatgctgg tgtcattgcg acagctaagc     600
attatatcat gaacgaacaa gagcatttcc gccaacaacc cgaggctgcg ggttacggat     660
tcaacgtaag cgacagtttg agttccaacg ttgatgacaa gactatgcat gaattgtacc     720
tctggcccct cgcggatgca gtacgcgctg gagtcggtgc tgtcatgtgc tcttacaacc     780
aaatcaacaa cagctacggt tgcgagaata gcgaaactct gaacaagctt ttgaaggcgg     840
agcttggttt ccaaggcttc gtcatgagtg attggaccgc tcatcacagc ggcgtaggcg     900
ctgctttagc aggtctggat atgtcgatgc ccggtgatgt taccttcgat agtggtacgt     960
ctttctgggg tgcaaacttg acggtcgtgt ccttaacgg tacaatcccc caatggcgtg    1020
ttgatgacat ggctgtccgt atcatggccg cttattacaa ggttggccgc gacaccaaat    1080
acaccctcc caacttcagc tcgtggacca gggacgaata tggtttcgcg cataaccatg    1140
tttcggaagg tgcttacgag agggtcaacg aattcgtgga cgtgcaacgc gatcatgccg    1200
acctaatccg tcgcatcggc gcgcagagca ctgttctgct gaagaacaag ggtgccttgc    1260
ccttgagccg caaggaaaag ctggtcgccc ttctgggaga ggatgcgggt tccaactcgt    1320
ggggcgctaa cggctgtgat gaccgtggtt gcgataacgg tacccttgcc atggcctggg    1380
gtagcggtac tgcgaatttc ccatacctcg tgacaccaga gcaggcgatt cagaacgaag    1440
ttcttcaggg ccgtggtaat gtcttcgccg tgaccgacag ttgggcgctc gacaagatcg    1500
ctgcggctgc ccgccaggcc agcgtatctc tcgtgttcgt caactccgac tcaggagaaa    1560
gctatcttag tgtggatgga atgagggcg atcgtaacaa catcactctg tggaagaacg    1620
gcgacaatgt ggtcaagacc gcagcgaata actgtaacaa caccgtggtc atcatccact    1680
ccgtcggacc agttttgatc gatgaatggt atgaccaccc caatgtcact ggtattctct    1740
gggctggtct gccaggccag gagtctggta actccatcgc cgatgtgctg tacggtcgtg    1800
tcaaccctgg cgccaagtct cctttcactt ggggcaagac ccgggagtcg tatggttctc    1860
ccttggtcaa ggatgccaac aatggcaacg gagcgcccca gtctgatttc acccagggtg    1920
ttttcatcga ttaccgccat ttcgataagt tcaatgagac ccctatctac gagtttggct    1980
acggcttgag ctacaccacc ttcgagctct ccgacctcca tgttcagccc ctgaacgcgt    2040
cccgatacac tcccaccagt ggcatgactg aagctgcaaa gaactttggt gaaattggcg    2100
atgcgtcgga gtacgtgtat ccggagggc tggaaaggat ccatgagttt atctatccct    2160
ggatcaactc taccgacctg aaggcatcgt ctgacgattc taactacggc tgggaagact    2220
ccaagtatat tcccgaaggc gccacggatg ggtctgccca gccccgtttg cccgctagtg    2280
```

```
gtggtgccgg aggaaacccc ggtctgtacg aggatctttt ccgcgtctct gtgaaggtca    2340
agaacacggg caatgtcgcc ggtgatgaag ttcctcagct gtacgtttcc ctaggcggcc    2400
cgaatgagcc caaggtggta ctgcgcaagt ttgagcgtat tcacttggcc ccttcgcagg    2460
aggccgtgtg acaacgacc cttacccgtc gtgaccttgc aaactgggac gtttcggctc    2520
aggactggac cgtcactcct taccccaaga cgatctacgt tggaaactcc tcacggaaac    2580
tgccgctcca ggcctcgctg cctaaggccc agtaagggc aagtcctgat tgtacagagc    2640
atttcgagat ttatgatgta catgtttatg aatgacctag ggtagggtaa tacttagtag    2700
ggttagttct aattcttgga gtcaagtatt gactcactgg gccgataaaa aaaaaaaaa    2760 aaaaaaaaa a                                                         2771
```

<210> SEQ ID NO 26
<211> LENGTH: 861
<212> TYPE: PRT
<213> ORGANISM: Aspergillus oryzae

<400> SEQUENCE: 26

```
Met Lys Leu Gly Trp Ile Glu Val Ala Ala Leu Ala Ala Ala Ser Val
1               5                   10                  15

Val Ser Ala Lys Asp Asp Leu Ala Tyr Ser Pro Pro Phe Tyr Pro Ser
            20                  25                  30

Pro Trp Ala Asp Gly Gln Gly Glu Trp Ala Glu Val Tyr Lys Arg Ala
        35                  40                  45

Val Asp Ile Val Ser Gln Met Thr Leu Thr Glu Lys Val Asn Leu Thr
    50                  55                  60

Thr Gly Thr Gly Trp Gln Leu Glu Arg Cys Val Gly Gln Thr Gly Ser
65                  70                  75                  80

Val Pro Arg Leu Asn Ile Pro Ser Leu Cys Leu Gln Asp Ser Pro Leu
                85                  90                  95

Gly Ile Arg Phe Ser Asp Tyr Asn Ser Ala Phe Pro Ala Gly Val Asn
            100                 105                 110

Val Ala Ala Thr Trp Asp Lys Thr Leu Ala Tyr Leu Arg Gly Gln Ala
        115                 120                 125

Met Gly Glu Glu Phe Ser Asp Lys Gly Ile Asp Val Gln Leu Gly Pro
    130                 135                 140

Ala Ala Gly Pro Leu Gly Ala His Pro Asp Gly Gly Arg Asn Trp Glu
145                 150                 155                 160

Gly Phe Ser Pro Asp Pro Ala Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Met Asn Glu Gln Glu His Phe Arg Gln Gln Pro Glu Ala Ala Gly
        195                 200                 205

Tyr Gly Phe Asn Val Ser Asp Ser Leu Ser Ser Asn Val Asp Asp Lys
    210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Glu Asn Ser Glu Thr Leu Asn Lys Leu Leu Lys Ala Glu Leu
            260                 265                 270

Gly Phe Gln Gly Phe Val Met Ser Asp Trp Thr Ala His His Ser Gly
```

-continued

```
            275                 280                 285
Val Gly Ala Ala Leu Ala Gly Leu Asp Met Ser Met Pro Gly Asp Val
            290                 295                 300
Thr Phe Asp Ser Gly Thr Ser Phe Trp Gly Ala Asn Leu Thr Val Gly
305                 310                 315                 320
Val Leu Asn Gly Thr Ile Pro Gln Trp Arg Val Asp Asp Met Ala Val
                    325                 330                 335
Arg Ile Met Ala Ala Tyr Tyr Lys Val Gly Arg Asp Thr Lys Tyr Thr
                340                 345                 350
Pro Pro Asn Phe Ser Ser Trp Thr Arg Asp Glu Tyr Gly Phe Ala His
                355                 360                 365
Asn His Val Ser Glu Gly Ala Tyr Glu Arg Val Asn Glu Phe Val Asp
            370                 375                 380
Val Gln Arg Asp His Ala Asp Leu Ile Arg Arg Ile Gly Ala Gln Ser
385                 390                 395                 400
Thr Val Leu Leu Lys Asn Lys Gly Ala Leu Pro Leu Ser Arg Lys Glu
                    405                 410                 415
Lys Leu Val Ala Leu Leu Gly Glu Asp Ala Gly Ser Asn Ser Trp Gly
                420                 425                 430
Ala Asn Gly Cys Asp Asp Arg Gly Cys Asp Asn Gly Thr Leu Ala Met
                435                 440                 445
Ala Trp Gly Ser Gly Thr Ala Asn Phe Pro Tyr Leu Val Thr Pro Glu
450                 455                 460
Gln Ala Ile Gln Asn Glu Val Leu Gln Gly Arg Gly Asn Val Phe Ala
465                 470                 475                 480
Val Thr Asp Ser Trp Ala Leu Asp Lys Ile Ala Ala Ala Arg Gln
                    485                 490                 495
Ala Ser Val Ser Leu Val Phe Val Asn Ser Asp Ser Gly Glu Ser Tyr
                500                 505                 510
Leu Ser Val Asp Gly Asn Glu Gly Asp Arg Asn Asn Ile Thr Leu Trp
                515                 520                 525
Lys Asn Gly Asp Asn Val Val Lys Thr Ala Ala Asn Cys Asn Asn
                530                 535                 540
Thr Val Val Ile Ile His Ser Val Gly Pro Val Leu Ile Asp Glu Trp
545                 550                 555                 560
Tyr Asp His Pro Asn Val Thr Gly Ile Leu Trp Ala Gly Leu Pro Gly
                    565                 570                 575
Gln Glu Ser Gly Asn Ser Ile Ala Asp Val Leu Tyr Gly Arg Val Asn
                580                 585                 590
Pro Gly Ala Lys Ser Pro Phe Thr Trp Gly Lys Thr Arg Glu Ser Tyr
                595                 600                 605
Gly Ser Pro Leu Val Lys Asp Ala Asn Asn Gly Asn Gly Ala Pro Gln
            610                 615                 620
Ser Asp Phe Thr Gln Gly Val Phe Ile Asp Tyr Arg His Phe Asp Lys
625                 630                 635                 640
Phe Asn Glu Thr Pro Ile Tyr Glu Phe Gly Tyr Gly Leu Ser Tyr Thr
                    645                 650                 655
Thr Phe Glu Leu Ser Asp Leu His Val Gln Pro Leu Asn Ala Ser Arg
                660                 665                 670
Tyr Thr Pro Thr Ser Gly Met Thr Glu Ala Ala Lys Asn Phe Gly Glu
                675                 680                 685
Ile Gly Asp Ala Ser Glu Tyr Val Tyr Pro Glu Gly Leu Glu Arg Ile
            690                 695                 700
```

```
His Glu Phe Ile Tyr Pro Trp Ile Asn Ser Thr Asp Leu Lys Ala Ser
705                 710                 715                 720

Ser Asp Asp Ser Asn Tyr Gly Trp Glu Asp Ser Lys Tyr Ile Pro Glu
            725                 730                 735

Gly Ala Thr Asp Gly Ser Ala Gln Pro Arg Leu Pro Ala Ser Gly Gly
        740                 745                 750

Ala Gly Gly Asn Pro Gly Leu Tyr Glu Asp Leu Phe Arg Val Ser Val
    755                 760                 765

Lys Val Lys Asn Thr Gly Asn Val Ala Gly Asp Glu Val Pro Gln Leu
770                 775                 780

Tyr Val Ser Leu Gly Gly Pro Asn Glu Pro Lys Val Val Leu Arg Lys
785                 790                 795                 800

Phe Glu Arg Ile His Leu Ala Pro Ser Gln Glu Ala Val Trp Thr Thr
                805                 810                 815

Thr Leu Thr Arg Arg Asp Leu Ala Asn Trp Asp Val Ser Ala Gln Asp
            820                 825                 830

Trp Thr Val Thr Pro Tyr Pro Lys Thr Ile Tyr Val Gly Asn Ser Ser
        835                 840                 845

Arg Lys Leu Pro Leu Gln Ala Ser Leu Pro Lys Ala Gln
    850                 855                 860

<210> SEQ ID NO 27
<211> LENGTH: 3060
<212> TYPE: DNA
<213> ORGANISM: Aspergillus fumigatus

<400> SEQUENCE: 27
atgagattcg gttggctcga ggtggccgct ctgacggccg cttctgtagc caatgcccag      60
gtttgtgatg cttttcccgtc attgtttcgg atatagttga caatagtcat ggaaataatc     120
aggaattggc tttctctcca ccattctacc cttcgccttg ggctgatggc cagggagagt     180
gggcagatgc ccatcgacgc gccgtcgaga tcgtttctca gatgacactg gcggagaagg     240
ttaaccttac aacgggtact gggtgggttg cgactttttt gttgacagtg agctttcttc     300
actgaccatc tacacagatg ggaaatggac cgatgcgtcg gtcaaacgg cagcgttccc     360 aggtaagctt gcaattctgc aacaacgtgc aagtgtagtt gctaaaacgc ggtggtgcag     420
acttggtatc aactggggtc tttgtggcca ggattcccct ttgggtatcc gtttctgtga     480
gctatacccg cggagtcttt cagtccttgt attatgtgct gatgattgtc tctgtatagc     540
tgacctcaac tccgccttcc ctgctggtac taatgtcgcc gcgacatggg acaagacact     600
cgcctacctt cgtggcaagg ccatgggtga ggaattcaac gacaagggcg tggacatttt     660 gctgggggcct gctgctggtc ctctcggcaa atacccggac ggcggcagaa tctgggaagg     720
cttctctcct gatccggttc tcactggtgt acttttcgcc gaaactatca agggtatcca     780
agacgcgggt gtgattgcta ctgccaagca ttacattctg aatgaacagg agcatttccg     840
acaggttggc gaggcccagg gatatggtta caacatcacg gagacgatca gctccaacgt     900
ggatgacaag accatgcacg agttgtacct ttggtgagta gttgcactg caaatgagga     960 ccttgattga tttgactgac ctggaatgca ggcccttgc agatgctgtg cgcggtaaga    1020 tttttccgtag acttgaccctc gcgacgaaga atcgctgac gaaccatcgt agctggcgtt    1080
ggcgctgtca tgtgttccta caatcaaatc aacaacagct acggttgtca aaacagtcaa    1140
actctcaaca agctcctcaa ggctgagctg ggcttccaag gcttcgtcat gagtgactgg    1200
```

```
agcgctcacc acagcggtgt cggcgctgcc ctcgctgggt tggatatgtc gatgcctgga    1260
gacatttcct tcgacgacgg actctccttc tggggcacga acctaactgt cagtgttctt    1320
aacggcaccg ttccagcctg gcgtgtcgat gacatggctg ttcgtatcat gaccgcgtac    1380
tacaaggttg gtcgtgaccg tcttcgtatt cccctaact tcagctcctg gacccgggat    1440
gagtacggct gggagcattc tgctgtctcc gagggagcct ggaccaaggt gaacgacttc    1500
gtcaatgtgc agcgcagtca ctctcagatc atccgtgaga ttggtgccgc tagtacagtg    1560
ctcttgaaga cacgggtgc tcttcctttg accggcaagg aggttaaagt gggtgttctc    1620
ggtgaagacg ctggttccaa cccgtggggt gctaacggct gccccgaccg cggctgtgat    1680
aacggcactc ttgctatggc ctggggtagt ggtactgcca acttcccta ccttgtcacc    1740
cccgagcagg ctatccagcg agaggtcatc agcaacggcg gcaatgtctt tgctgtgact    1800
gataacgggg ctctcagcca gatggcagat gttgcatctc aatccaggtg agtgcgggct    1860
cttagaaaaa gaacgttctc tgaatgaagt tttttaacca ttgcgaacag cgtgtctttg    1920
gtgtttgtca acgccgactc tggagagggt ttcatcagtg tcgacggcaa cgagggtgac    1980
cgcaaaaatc tcactctgtg gaagaacggc gaggccgtca ttgacactgt tgtcagccac    2040
tgcaacaaca cgattgtggt tattcacagt gttgggcccg tcttgatcga ccggtggtat    2100
gataacccca acgtcactgc catcatctgg gccggcttgc ccggtcagga gagtggcaac    2160
tccctggtcg acgtgctcta tggccgcgtc aaccccagcg ccaagacccc gttcacctgg    2220
ggcaagactc gggagtctta cggggctccc ttgctcaccg agcctaacaa tggcaatggt    2280
gctccccagg atgatttcaa cgagggcgtc ttcattgact accgtcactt tgacaagcgc    2340
aatgagaccc ccatttatga gtttggccat ggcttgagct acaccacctt tggttactct    2400
caccttcggg ttcaggccct caatagttcg agttcggcat atgtcccgac tagcggagag    2460
accaagcctg cgccaaccta tggtgagatc ggtagtgccg ccgactacct gtatcccgag    2520
ggtctcaaaa gaattaccaa gtttatttac ccttggctca actcgaccga cctcgaggat    2580
tcttctgacg acccgaacta cggctgggag gactcggagt acattcccga aggcgctagg    2640
gatgggtctc ctcaaccccct cctgaaggct ggcggcgctc ctggtggtaa ccctacccct    2700
tatcaggatc ttgttagggt gtcggccacc ataaccaaca ctggtaacgt cgccggttat    2760
gaagtccctc aattggtgag tgacccgcat gttccttgcg ttgcaatttg gctaactcgc    2820
ttctagtatg tttcactggg cggaccgaac gagcctcggg tcgttctgcg caagttcgac    2880
cgaatcttcc tggctcctgg ggagcaaaag gtttggacca cgactcttaa ccgtcgtgat    2940
ctcgccaatt gggatgtgga ggctcaggac tgggtcatca caaagtaccc caagaaagtg    3000
cacgtcggca gctcctcgcg taagctgcct ctgagagcgc tctgccccg tgtctactag    3060
```

<210> SEQ ID NO 28
<211> LENGTH: 863
<212> TYPE: PRT
<213> ORGANISM: Aspergillus fumigatus

<400> SEQUENCE: 28

```
Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
            20                  25                  30

Trp Ala Asp Gly Gln Gly Glu Trp Ala Asp Ala His Arg Arg Ala Val
        35                  40                  45
```

-continued

```
Glu Ile Val Ser Gln Met Thr Leu Ala Glu Lys Val Asn Leu Thr Thr
     50                  55                  60
Gly Thr Gly Trp Glu Met Asp Arg Cys Val Gly Gln Thr Gly Ser Val
 65                  70                  75                  80
Pro Arg Leu Gly Ile Asn Trp Gly Leu Cys Gly Gln Asp Ser Pro Leu
                 85                  90                  95
Gly Ile Arg Phe Ser Asp Leu Asn Ser Ala Phe Pro Ala Gly Thr Asn
            100                 105                 110
Val Ala Ala Thr Trp Asp Lys Thr Leu Ala Tyr Leu Arg Gly Lys Ala
        115                 120                 125
Met Gly Glu Glu Phe Asn Asp Lys Gly Val Asp Ile Leu Leu Gly Pro
130                 135                 140
Ala Ala Gly Pro Leu Gly Lys Tyr Pro Asp Gly Gly Arg Ile Trp Glu
145                 150                 155                 160
Gly Phe Ser Pro Asp Pro Val Leu Thr Gly Val Leu Phe Ala Glu Thr
                165                 170                 175
Ile Lys Gly Ile Gln Asp Ala Gly Val Ile Ala Thr Ala Lys His Tyr
            180                 185                 190
Ile Leu Asn Glu Gln Glu His Phe Arg Gln Val Gly Glu Ala Gln Gly
        195                 200                 205
Tyr Gly Tyr Asn Ile Thr Glu Thr Ile Ser Ser Asn Val Asp Asp Lys
210                 215                 220
Thr Met His Glu Leu Tyr Leu Trp Pro Phe Ala Asp Ala Val Arg Ala
225                 230                 235                 240
Gly Val Gly Ala Val Met Cys Ser Tyr Asn Gln Ile Asn Asn Ser Tyr
                245                 250                 255
Gly Cys Gln Asn Ser Gln Thr Leu Asn Lys Leu Leu Lys Ala Glu Leu
            260                 265                 270
Gly Phe Gln Gly Phe Val Met Ser Asp Trp Ser Ala His His Ser Gly
        275                 280                 285
Val Gly Ala Ala Leu Ala Gly Leu Asp Met Ser Met Pro Gly Asp Ile
290                 295                 300
Ser Phe Asp Asp Gly Leu Ser Phe Trp Gly Thr Asn Leu Thr Val Ser
305                 310                 315                 320
Val Leu Asn Gly Thr Val Pro Ala Trp Arg Val Asp Asp Met Ala Val
                325                 330                 335
Arg Ile Met Thr Ala Tyr Tyr Lys Val Gly Arg Asp Arg Leu Arg Ile
            340                 345                 350
Pro Pro Asn Phe Ser Ser Trp Thr Arg Asp Glu Tyr Gly Trp Glu His
        355                 360                 365
Ser Ala Val Ser Glu Gly Ala Trp Thr Lys Val Asn Asp Phe Val Asn
370                 375                 380
Val Gln Arg Ser His Ser Gln Ile Ile Arg Glu Ile Gly Ala Ala Ser
385                 390                 395                 400
Thr Val Leu Leu Lys Asn Thr Gly Ala Leu Pro Leu Thr Gly Lys Glu
                405                 410                 415
Val Lys Val Gly Val Leu Gly Glu Asp Ala Gly Ser Asn Pro Trp Gly
            420                 425                 430
Ala Asn Gly Cys Pro Asp Arg Gly Cys Asp Asn Gly Thr Leu Ala Met
        435                 440                 445
Ala Trp Gly Ser Gly Thr Ala Asn Phe Pro Tyr Leu Val Thr Pro Glu
450                 455                 460
Gln Ala Ile Gln Arg Glu Val Ile Ser Asn Gly Gly Asn Val Phe Ala
```

```
                465                 470                 475                 480
        Val Thr Asp Asn Gly Ala Leu Ser Gln Met Ala Asp Val Ala Ser Gln
                        485                 490                 495

Ser Ser Val Ser Leu Val Phe Val Asn Ala Asp Ser Gly Glu Gly Phe
                        500                 505                 510

Ile Ser Val Asp Gly Asn Glu Gly Asp Arg Lys Asn Leu Thr Leu Trp
                        515                 520                 525

Lys Asn Gly Glu Ala Val Ile Asp Thr Val Val Ser His Cys Asn Asn
                        530                 535                 540

Thr Ile Val Val Ile His Ser Val Gly Pro Val Leu Ile Asp Arg Trp
        545                 550                 555                 560

Tyr Asp Asn Pro Asn Val Thr Ala Ile Ile Trp Ala Gly Leu Pro Gly
                        565                 570                 575

Gln Glu Ser Gly Asn Ser Leu Val Asp Val Leu Tyr Gly Arg Val Asn
                        580                 585                 590

Pro Ser Ala Lys Thr Pro Phe Thr Trp Gly Lys Thr Arg Glu Ser Tyr
                        595                 600                 605

Gly Ala Pro Leu Leu Thr Glu Pro Asn Asn Gly Asn Gly Ala Pro Gln
                        610                 615                 620

Asp Asp Phe Asn Glu Gly Val Phe Ile Asp Tyr Arg His Phe Asp Lys
        625                 630                 635                 640

Arg Asn Glu Thr Pro Ile Tyr Glu Phe Gly His Gly Leu Ser Tyr Thr
                        645                 650                 655

Thr Phe Gly Tyr Ser His Leu Arg Val Gln Ala Leu Asn Ser Ser Ser
                        660                 665                 670

Ser Ala Tyr Val Pro Thr Ser Gly Glu Thr Lys Pro Ala Pro Thr Tyr
                        675                 680                 685

Gly Glu Ile Gly Ser Ala Ala Asp Tyr Leu Tyr Pro Glu Gly Leu Lys
                        690                 695                 700

Arg Ile Thr Lys Phe Ile Tyr Pro Trp Leu Asn Ser Thr Asp Leu Glu
        705                 710                 715                 720

Asp Ser Ser Asp Asp Pro Asn Tyr Gly Trp Glu Asp Ser Glu Tyr Ile
                        725                 730                 735

Pro Glu Gly Ala Arg Asp Gly Ser Pro Gln Pro Leu Leu Lys Ala Gly
                        740                 745                 750

Gly Ala Pro Gly Gly Asn Pro Thr Leu Tyr Gln Asp Leu Val Arg Val
                        755                 760                 765

Ser Ala Thr Ile Thr Asn Thr Gly Asn Val Ala Gly Tyr Glu Val Pro
        770                 775                 780

Gln Leu Tyr Val Ser Leu Gly Gly Pro Asn Glu Pro Arg Val Val Leu
        785                 790                 795                 800

Arg Lys Phe Asp Arg Ile Phe Leu Ala Pro Gly Glu Gln Lys Val Trp
                        805                 810                 815

Thr Thr Thr Leu Asn Arg Arg Asp Leu Ala Asn Trp Asp Val Glu Ala
                        820                 825                 830

Gln Asp Trp Val Ile Thr Lys Tyr Pro Lys Lys Val His Val Gly Ser
                        835                 840                 845

Ser Ser Arg Lys Leu Pro Leu Arg Ala Pro Leu Pro Arg Val Tyr
                        850                 855                 860

<210> SEQ ID NO 29
<211> LENGTH: 2800
<212> TYPE: DNA
<213> ORGANISM: Penicillium brasilianum
```

<400> SEQUENCE: 29

```
tgaaaatgca gggttctaca atctttctgg ctttcgcctc atgggcgagc caggttgctg      60
ccattgcgca gcccatacag aagcacgagg tttgttttat cttgctcatg gacgtgcttt     120
gacttgacta attgttttac atacagcccg gatttctgca cgggcccaa gccatagaat      180
cgttctcaga accgttctac ccgtcgccct ggatgaatcc tcacgccgag ggctgggagg     240
ccgcatatca gaaagctcaa gattttgtct cgcaactcac tatcttggag aaaataaatc    300
tgaccaccgg tgttgggtaa gtctctccga ctgcttctgg gtcacggtgc gacgagccac    360
tgactttttg aagctgggaa atgggccgt gtgtaggaaa cactggatca attcctcgtc     420
tcggattcaa aggattttgt acccaggatt caccacaggg tgttcggttc gcagattatt    480
cctccgcttt cacatctagc caaatggccg ccgcaacatt tgaccgctca attctttatc    540
aacgaggcca agccatggca caggaacaca aggctaaggg tatcacaatt caattgggcc    600
ctgttgccgg ccctctcggt cgcatccccg agggcggccg caactgggaa ggattctccc    660
ctgatcctgt cttgactggt atagccatgg ctgagacaat taagggcatg caggatactg    720
gagtgattgc ttgcgctaaa cattatattg gaaacgagca ggagcacttc cgtcaagtgg    780
gtgaagctgc gggtcacgga tacactatt ccgatactat ttcatctaat attgacgacc     840
gtgctatgca tgagctatac ttgtggccat ttgctgatgc cgttcgcgct ggtgtgggtt    900
cttctcatgtg ctcatactct cagatcaaca actcctacgg atgccaaaac agtcagaccc   960
tcaacaagct cctcaagagc gaattgggct tccaaggctt tgtcatgagc gattggggtg   1020
cccatcactc tggagtgtca tcggcgctag ctggacttga tatgagcatg ccgggtgata   1080
ccgaatttga ttctggcttg agcttctggg gctctaacct caccattgca attctgaacg   1140
gcacggttcc cgaatggcgc ctggatgaca tggcgatgcg aattatggct gcatacttca   1200
aagttggcct tactattgag gatcaaccag atgtcaactt caatgcctgg acccatgaca   1260
cctacggata taaatacgct tatagcaagg aagattacga gcaggtcaac tggcatgtcg   1320
atgttcgcag cgaccacaat aagctcattc gcgagactgc cgcgaagggt acagttctgc   1380
tgaagaacaa ctttcatgct ctccctctga agcagcccag gttcgtggcc gtcgttggtc   1440
aggatgccgg gccaaacccc aagggcccta acggctgcgc agaccgagga tgcgaccaag   1500
gcactctcgc aatgggatgg ggctcagggt ctaccgaatt cccttacctg gtcactcctg   1560
acactgctat tcagtcaaag gtcctcgaat acggggtcg atacgagagt attttgata    1620
actatgacga caatgctatc ttgtcgcttg tctcacagcc tgatgcaacc tgtatcgttt   1680
ttgcaaatgc cgattccggt gaaggctaca tcactgtcga caacaactgg ggtgaccgca   1740
acaatctgac cctctggcaa aatgccgatc aagtgattag cactgtcagc tcgcgatgca   1800
acaacacaat cgttgttctc cactctgtcg gaccagtgtt gctaaatggt atatatgagc   1860
acccgaacat cacagctatt gtctgggcag ggatgccagg cgaagaatct ggcaatgctc   1920
tcgtggatat tctttggggc aatgttaacc ctgccggtcg cactccgttc acctgggcca   1980
aaagtcgaga ggactatggc actgatataa tgtacgagcc caacaacggc cagcgtgcgc   2040
ctcagcagga tttcaccgag agcatctacc tcgactaccg ccatttcgac aaagctggta   2100
tcgagccaat ttacgagttt ggattcggcc tctcctatac caccttcgaa tactctgacc   2160
tccgtgttgt gaagaagtat gttcaaccat acagtcccac gaccggcacc ggtgctcaag   2220
caccttccat cggacagcca cctagccaga acctggatac ctacaagttc cctgctacat   2280
```

```
acaagtacat caaaaccttc atttatccct acctgaacag cactgtctcc ctccgcgctg    2340
cttccaagga tcccgaatac ggtcgtacag actttatccc accccacgcg cgtgatggct    2400
cccctcaacc tctcaacccc gctggagacc cagtggccag tggtggaaac aacatgctct    2460
acgacgaact ttacgaggtc actgcacaga tcaaaaacac tggcgacgtg gccggcgacg    2520
aagtcgtcca gctttacgta gatctcgggg gtgacaaccc gcctcgtcag ttgagaaact    2580
ttgacaggtt ttatctgctg cccggtcaga gctcaacatt ccgggctaca ttgacgcgcc    2640
gtgatttgag caactgggat attgaggcgc agaactggcg agttacggaa tcgcctaaga    2700
gagtgtatgt tggacggtcg agtcgggatt tgccgctgag ctcacaattg gagtaatgat    2760
catgtctacc aatagatgtt gaatgtctgg tgtggatatt                          2800
```

<210> SEQ ID NO 30
<211> LENGTH: 878
<212> TYPE: PRT
<213> ORGANISM: Penicillium brasilianum

<400> SEQUENCE: 30

```
Met Gln Gly Ser Thr Ile Phe Leu Ala Phe Ala Ser Trp Ala Ser Gln
1               5                   10                  15

Val Ala Ala Ile Ala Gln Pro Ile Gln Lys His Glu Pro Gly Phe Leu
            20                  25                  30

His Gly Pro Gln Ala Ile Glu Ser Phe Ser Glu Pro Phe Tyr Pro Ser
        35                  40                  45

Pro Trp Met Asn Pro His Ala Glu Gly Trp Glu Ala Ala Tyr Gln Lys
    50                  55                  60

Ala Gln Asp Phe Val Ser Gln Leu Thr Ile Leu Glu Lys Ile Asn Leu
65                  70                  75                  80

Thr Thr Gly Val Gly Trp Glu Asn Gly Pro Cys Val Gly Asn Thr Gly
                85                  90                  95

Ser Ile Pro Arg Leu Gly Phe Lys Gly Phe Cys Thr Gln Asp Ser Pro
            100                 105                 110

Gln Gly Val Arg Phe Ala Asp Tyr Ser Ser Ala Phe Thr Ser Ser Gln
        115                 120                 125

Met Ala Ala Ala Thr Phe Asp Arg Ser Ile Leu Tyr Gln Arg Gly Gln
    130                 135                 140

Ala Met Ala Gln Glu His Lys Ala Lys Gly Ile Thr Ile Gln Leu Gly
145                 150                 155                 160

Pro Val Ala Gly Pro Leu Gly Arg Ile Pro Glu Gly Gly Arg Asn Trp
                165                 170                 175

Glu Gly Phe Ser Pro Asp Pro Val Leu Thr Gly Ile Ala Met Ala Glu
            180                 185                 190

Thr Ile Lys Gly Met Gln Asp Thr Gly Val Ile Ala Cys Ala Lys His
        195                 200                 205

Tyr Ile Gly Asn Glu Gln Glu His Phe Arg Gln Val Gly Glu Ala Ala
    210                 215                 220

Gly His Gly Tyr Thr Ile Ser Asp Thr Ile Ser Ser Asn Ile Asp Asp
225                 230                 235                 240

Arg Ala Met His Glu Leu Tyr Leu Trp Pro Phe Ala Asp Ala Val Arg
                245                 250                 255

Ala Gly Val Gly Ser Phe Met Cys Ser Tyr Ser Gln Ile Asn Asn Ser
            260                 265                 270

Tyr Gly Cys Gln Asn Ser Gln Thr Leu Asn Lys Leu Leu Lys Ser Glu
        275                 280                 285
```

```
Leu Gly Phe Gln Gly Phe Val Met Ser Asp Trp Ala His His Ser
    290                 295                 300

Gly Val Ser Ser Ala Leu Ala Gly Leu Asp Met Ser Met Pro Gly Asp
305                 310                 315                 320

Thr Glu Phe Asp Ser Gly Leu Ser Phe Trp Gly Ser Asn Leu Thr Ile
                325                 330                 335

Ala Ile Leu Asn Gly Thr Val Pro Glu Trp Arg Leu Asp Asp Met Ala
            340                 345                 350

Met Arg Ile Met Ala Ala Tyr Phe Lys Val Gly Leu Thr Ile Glu Asp
        355                 360                 365

Gln Pro Asp Val Asn Phe Asn Ala Trp Thr His Asp Thr Tyr Gly Tyr
    370                 375                 380

Lys Tyr Ala Tyr Ser Lys Glu Asp Tyr Glu Gln Val Asn Trp His Val
385                 390                 395                 400

Asp Val Arg Ser Asp His Asn Lys Leu Ile Arg Glu Thr Ala Ala Lys
                405                 410                 415

Gly Thr Val Leu Leu Lys Asn Asn Phe His Ala Leu Pro Leu Lys Gln
            420                 425                 430

Pro Arg Phe Val Ala Val Gly Gln Asp Ala Gly Pro Asn Pro Lys
        435                 440                 445

Gly Pro Asn Gly Cys Ala Asp Arg Gly Cys Asp Gln Gly Thr Leu Ala
    450                 455                 460

Met Gly Trp Gly Ser Gly Ser Thr Glu Phe Pro Tyr Leu Val Thr Pro
465                 470                 475                 480

Asp Thr Ala Ile Gln Ser Lys Val Leu Glu Tyr Gly Arg Tyr Glu
                485                 490                 495

Ser Ile Phe Asp Asn Tyr Asp Asp Asn Ala Ile Leu Ser Leu Val Ser
            500                 505                 510

Gln Pro Asp Ala Thr Cys Ile Val Phe Ala Asn Ala Asp Ser Gly Glu
        515                 520                 525

Gly Tyr Ile Thr Val Asp Asn Asn Trp Gly Asp Arg Asn Asn Leu Thr
    530                 535                 540

Leu Trp Gln Asn Ala Asp Gln Val Ile Ser Thr Val Ser Ser Arg Cys
545                 550                 555                 560

Asn Asn Thr Ile Val Val Leu His Ser Val Gly Pro Val Leu Leu Asn
                565                 570                 575

Gly Ile Tyr Glu His Pro Asn Ile Thr Ala Ile Val Trp Ala Gly Met
            580                 585                 590

Pro Gly Glu Glu Ser Gly Asn Ala Leu Val Asp Ile Leu Trp Gly Asn
        595                 600                 605

Val Asn Pro Ala Gly Arg Thr Pro Phe Thr Trp Ala Lys Ser Arg Glu
    610                 615                 620

Asp Tyr Gly Thr Asp Ile Met Tyr Glu Pro Asn Asn Gly Gln Arg Ala
625                 630                 635                 640

Pro Gln Gln Asp Phe Thr Glu Ser Ile Tyr Leu Asp Tyr Arg His Phe
                645                 650                 655

Asp Lys Ala Gly Ile Glu Pro Ile Tyr Glu Phe Gly Phe Gly Leu Ser
            660                 665                 670

Tyr Thr Thr Phe Glu Tyr Ser Asp Leu Arg Val Val Lys Lys Tyr Val
        675                 680                 685

Gln Pro Tyr Ser Pro Thr Thr Gly Thr Gly Ala Gln Ala Pro Ser Ile
    690                 695                 700
```

Gly Gln Pro Pro Ser Gln Asn Leu Asp Thr Tyr Lys Phe Pro Ala Thr
705                 710                 715                 720

Tyr Lys Tyr Ile Lys Thr Phe Ile Tyr Pro Tyr Leu Asn Ser Thr Val
            725                 730                 735

Ser Leu Arg Ala Ala Ser Lys Asp Pro Glu Tyr Gly Arg Thr Asp Phe
            740                 745                 750

Ile Pro Pro His Ala Arg Asp Gly Ser Pro Gln Pro Leu Asn Pro Ala
            755                 760                 765

Gly Asp Pro Val Ala Ser Gly Asn Asn Met Leu Tyr Asp Glu Leu
    770                 775                 780

Tyr Glu Val Thr Ala Gln Ile Lys Asn Thr Gly Asp Val Ala Gly Asp
785                 790                 795                 800

Glu Val Val Gln Leu Tyr Val Asp Leu Gly Gly Asp Asn Pro Pro Arg
            805                 810                 815

Gln Leu Arg Asn Phe Asp Arg Phe Tyr Leu Leu Pro Gly Gln Ser Ser
            820                 825                 830

Thr Phe Arg Ala Thr Leu Thr Arg Arg Asp Leu Ser Asn Trp Asp Ile
            835                 840                 845

Glu Ala Gln Asn Trp Arg Val Thr Glu Ser Pro Lys Arg Val Tyr Val
850                 855                 860

Gly Arg Ser Ser Arg Asp Leu Pro Leu Ser Ser Gln Leu Glu
865                 870                 875

<210> SEQ ID NO 31
<211> LENGTH: 19
<212> TYPE: PRT
<213> ORGANISM: Thielavia terrestris
<220> FEATURE:
<221> NAME/KEY: MISC_FEATURE
<222> LOCATION: (1)..(1)
<223> OTHER INFORMATION: X=I,L,M, OR V
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: X=I,L,M, OR V
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: MISC_FEATURE
<222> LOCATION: (14)..(14)
<223> OTHER INFORMATION: X=E OR Q
<220> FEATURE:
<221> NAME/KEY: misc_feature
<222> LOCATION: (15)..(18)
<223> OTHER INFORMATION: Xaa can be any naturally occurring amino acid
<220> FEATURE:
<221> NAME/KEY: MISC_FEATURE
<222> LOCATION: (19)..(19)
<223> OTHER INFORMATION: X=H,N, OR Q

<400> SEQUENCE: 31

Xaa Pro Xaa Xaa Xaa Xaa Gly Xaa Tyr Xaa Xaa Arg Xaa Xaa Xaa Xaa
1               5                   10                  15

```
-continued

Xaa Xaa Xaa

<210> SEQ ID NO 32
<211> LENGTH: 20
<212> TYPE: PRT
<213> ORGANISM: Thielavia terrestris
<220> FEATURE:
<221> NAME/KEY: MISC_FEATURE
<222> LOCATION: (1)..(1)
<223> OTHER INFORMATION: X=I,L,M, OR V
<220> FEATURE:
<221> NAME/KEY: misc_feature
<222> LOCATION: (3)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: X=I,L,M, OR V
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: MISC_FEATURE
<222> LOCATION: (15)..(15)
<223> OTHER INFORMATION: X=E OR Q
<220> FEATURE:
<221> NAME/KEY: misc_feature
<222> LOCATION: (16)..(19)
<223> OTHER INFORMATION: Xaa can be any naturally occurring amino acid
<220> FEATURE:
<221> NAME/KEY: MISC_FEATURE
<222> LOCATION: (20)..(20)
<223> OTHER INFORMATION: X=H,N, OR Q

<400> SEQUENCE: 32

Xaa Pro Xaa Xaa Xaa Xaa Xaa Gly Xaa Tyr Xaa Xaa Arg Xaa Xaa Xaa
1               5                   10                  15

Xaa Xaa Xaa Xaa
            20

<210> SEQ ID NO 33
<211> LENGTH: 9
<212> TYPE: PRT
<213> ORGANISM: Thielavia terrestris
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: X= Y OR W
<220> FEATURE:
<221> NAME/KEY: MISC_FEATURE
<222> LOCATION: (9)..(9)
<223> OTHER INFORMATION: X= A,I,L,M OR V

<400> SEQUENCE: 33

His Xaa Gly Pro Xaa Xaa Xaa Xaa Xaa
1               5
```

```
<210> SEQ ID NO 34
<211> LENGTH: 10
<212> TYPE: PRT
<213> ORGANISM: Thielavia terrestris
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: X= Y OR W
<220> FEATURE:
<221> NAME/KEY: MISC_FEATURE
<222> LOCATION: (10)..(10)
<223> OTHER INFORMATION: X= A,I,L,M OR V

<400> SEQUENCE: 34

His Xaa Xaa Gly Pro Xaa Xaa Xaa Xaa Xaa
1               5                   10

<210> SEQ ID NO 35
<211> LENGTH: 11
<212> TYPE: PRT
<213> ORGANISM: Thielavia terrestris
<220> FEATURE:
<221> NAME/KEY: MISC_FEATURE
<222> LOCATION: (1)..(1)
<223> OTHER INFORMATION: X= E OR Q
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: X= E,H,Q OR N
<220> FEATURE:
<221> NAME/KEY: MISC_FEATURE
<222> LOCATION: (9)..(9)
<223> OTHER INFORMATION: X=F,I,L, OR V
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: X=I,L,OR V

<400> SEQUENCE: 35

Xaa Xaa Tyr Xaa Xaa Cys Xaa Xaa Xaa Xaa Xaa
1               5                   10

<210> SEQ ID NO 36
<211> LENGTH: 9
<212> TYPE: PRT
<213> ORGANISM: Thielavia terrestris
<220> FEATURE:
<221> NAME/KEY: misc_feature
<222> LOCATION: (2)..(2)
```

```
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: X= Y OR W
<220> FEATURE:
<221> NAME/KEY: MISC_FEATURE
<222> LOCATION: (9)..(9)
<223> OTHER INFORMATION: X= A,I,L,M OR V

<400> SEQUENCE: 36

His Xaa Gly Pro Xaa Xaa Xaa Xaa Xaa
1               5

<210> SEQ ID NO 37
<211> LENGTH: 10
<212> TYPE: PRT
<213> ORGANISM: Thielavia terrestris
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: X= Y OR W
<220> FEATURE:
<221> NAME/KEY: MISC_FEATURE
<222> LOCATION: (10)..(10)
<223> OTHER INFORMATION: X= A,I,L,M OR V

<400> SEQUENCE: 37

His Xaa Xaa Gly Pro Xaa Xaa Xaa Xaa Xaa
1               5                   10

<210> SEQ ID NO 38
<211> LENGTH: 11
<212> TYPE: PRT
<213> ORGANISM: Thielavia terrestris
<220> FEATURE:
<221> NAME/KEY: MISC_FEATURE
<222> LOCATION: (1)..(1)
<223> OTHER INFORMATION: X= E OR Q
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: X= E,H,Q OR N
<220> FEATURE:
<221> NAME/KEY: MISC_FEATURE
<222> LOCATION: (9)..(9)
<223> OTHER INFORMATION: X=F,I,L, OR V
<220> FEATURE:
<221> NAME/KEY: misc_feature
<222> LOCATION: (10)..(10)
<223> OTHER INFORMATION: Xaa can be any naturally occurring amino acid
```

```
<220> FEATURE:
<221> NAME/KEY: MISC_FEATURE
<222> LOCATION: (11)..(11)
<223> OTHER INFORMATION: X=I,L,OR V

<400> SEQUENCE: 38

Xaa Xaa Tyr Xaa Xaa Cys Xaa Xaa Xaa Xaa Xaa
1               5                   10

<210> SEQ ID NO 39
<211> LENGTH: 19
<212> TYPE: PRT
<213> ORGANISM: Thielavia terrestris
<220> FEATURE:
<221> NAME/KEY: MISC_FEATURE
<222> LOCATION: (1)..(1)
<223> OTHER INFORMATION: X=I,L,M OR V
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: X=I,L,M OR V
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: MISC_FEATURE
<222> LOCATION: (14)..(14)
<223> OTHER INFORMATION: X= E OR Q
<220> FEATURE:
<221> NAME/KEY: misc_feature
<222> LOCATION: (15)..(17)
<223> OTHER INFORMATION: Xaa can be any naturally occurring amino acid
<220> FEATURE:
<221> NAME/KEY: MISC_FEATURE
<222> LOCATION: (19)..(19)
<223> OTHER INFORMATION: X= H,N, OR Q

<400> SEQUENCE: 39

Xaa Pro Xaa Xaa Xaa Xaa Gly Xaa Tyr Xaa Xaa Arg Xaa Xaa Xaa Xaa
1               5                   10                  15

Xaa Ala Xaa

<210> SEQ ID NO 40
<211> LENGTH: 20
<212> TYPE: PRT
<213> ORGANISM: Thielavia terrestris
<220> FEATURE:
<221> NAME/KEY: MISC_FEATURE
<222> LOCATION: (1)..(1)
<223> OTHER INFORMATION: X=I,L,M OR V
<220> FEATURE:
<221> NAME/KEY: misc_feature
<222> LOCATION: (3)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (11)..(11)
```

```
<223> OTHER INFORMATION: X=I,L,M OR V
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: MISC_FEATURE
<222> LOCATION: (15)..(15)
<223> OTHER INFORMATION: X=E OR Q
<220> FEATURE:
<221> NAME/KEY: misc_feature
<222> LOCATION: (16)..(18)
<223> OTHER INFORMATION: Xaa can be any naturally occurring amino acid
<220> FEATURE:
<221> NAME/KEY: MISC_FEATURE
<222> LOCATION: (20)..(20)
<223> OTHER INFORMATION: X= H,N, OR Q

<400> SEQUENCE: 40

Xaa Pro Xaa Xaa Xaa Xaa Xaa Gly Xaa Tyr Xaa Xaa Arg Xaa Xaa Xaa
1               5                   10                  15

Xaa Xaa Ala Xaa
            20

<210> SEQ ID NO 41
<211> LENGTH: 4
<212> TYPE: PRT
<213> ORGANISM: Thielavia terrestris
<220> FEATURE:
<221> NAME/KEY: MISC_FEATURE
<222> LOCATION: (1)..(1)
<223> OTHER INFORMATION: XAA = F or W
<220> FEATURE:
<221> NAME/KEY: MISC_FEATURE
<222> LOCATION: (2)..(2)
<223> OTHER INFORMATION: XAA = T or F
<220> FEATURE:
<221> NAME/KEY: MISC_FEATURE
<222> LOCATION: (4)..(4)
<223> OTHER INFORMATION: XAA = A, I or V

<400> SEQUENCE: 41

Xaa Xaa Leu Xaa
1
```